United States Patent
Roscigno et al.

(10) Patent No.: US 11,660,304 B2
(45) Date of Patent: *May 30, 2023

(54) DRY POWDER TREPROSTINIL FOR THE TREATMENT OF PULMONARY HYPERTENSION

(71) Applicant: LIQUIDIA TECHNOLOGIES, INC., Morrisville, NC (US)

(72) Inventors: Robert Frank Roscigno, Melbourne Beach, FL (US); Brian T. Farrer, Apex, NC (US); Jacob J. Sprague, Cary, NC (US); Benjamin Maynor, Durham, NC (US)

(73) Assignee: LIQUIDIA TECHNOLOGIES, INC., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/719,439

(22) Filed: Apr. 13, 2022

(65) Prior Publication Data

US 2022/0257608 A1   Aug. 18, 2022

Related U.S. Application Data

(63) Continuation of application No. 17/104,348, filed on Nov. 25, 2020, which is a continuation of application No. 16/099,135, filed as application No. PCT/US2017/031301 on May 5, 2017, now Pat. No. 10,898,494.

(60) Provisional application No. 62/472,204, filed on Mar. 16, 2017, provisional application No. 62/440,078, filed on Dec. 29, 2016, provisional application No. 62/404,960, filed on Oct. 6, 2016, provisional application No. 62/332,013, filed on May 5, 2016.

(51) Int. Cl.
| | | |
|---|---|---|
| A61K 9/00 | (2006.01) | |
| A61P 9/12 | (2006.01) | |
| A61K 31/557 | (2006.01) | |
| A61K 9/48 | (2006.01) | |
| A61K 31/5575 | (2006.01) | |
| A61K 47/02 | (2006.01) | |
| A61K 47/18 | (2017.01) | |
| A61K 47/26 | (2006.01) | |

(52) U.S. Cl.
CPC .......... *A61K 31/557* (2013.01); *A61K 9/0075* (2013.01); *A61K 9/4858* (2013.01); *A61K 31/5575* (2013.01); *A61P 9/12* (2018.01); *A61K 47/02* (2013.01); *A61K 47/183* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 5,153,222 A | 10/1992 | Tadepalli et al. | |
| 5,441,060 A | 8/1995 | Rose et al. | |
| 5,874,064 A | 2/1999 | Edwards et al. | |
| 6,503,480 B1 | 1/2003 | Edwards et al. | |
| 6,521,212 B1 | 2/2003 | Cloutier et al. | |
| 6,756,033 B2 | 6/2004 | Cloutier et al. | |
| 6,858,199 B1 | 2/2005 | Edwards et al. | |
| 6,921,528 B2 | 7/2005 | Edwards et al. | |
| 7,199,157 B2 | 4/2007 | Wade et al. | |
| 7,879,909 B2 | 2/2011 | Wade et al. | |
| 7,976,759 B2 | 7/2011 | Henn et al. | |
| 8,128,393 B2 * | 3/2012 | Rolland | B32B 38/0012 |
| | | | 425/363 |
| 8,158,728 B2 | 4/2012 | DeSimone et al. | |
| 8,263,129 B2 | 9/2012 | DeSimone et al. | |
| 8,268,446 B2 | 9/2012 | DeSimone et al. | |
| 8,350,079 B2 | 1/2013 | Walsh | |
| 8,420,124 B2 | 4/2013 | DeSimone et al. | |
| 8,444,907 B2 | 5/2013 | Ermochkine et al. | |
| 8,454,939 B2 | 6/2013 | Hrkach | |
| 8,518,316 B2 | 8/2013 | Henn et al. | |
| 8,765,813 B2 | 7/2014 | Wade et al. | |
| 8,887,715 B2 | 11/2014 | Hrkach | |
| 9,161,986 B2 | 10/2015 | Mizushima et al. | |
| 9,339,507 B2 | 5/2016 | Olschewski et al. | |
| 9,358,240 B2 | 6/2016 | Olschewski et al. | |

(Continued)

FOREIGN PATENT DOCUMENTS

| | | |
|---|---|---|
| EP | 1161234 B1 | 7/2003 |
| JP | 2009-537246 A | 10/2009 |

(Continued)

OTHER PUBLICATIONS

Notice of Reasons for Rejection, dated Mar. 2, 2022, for Japanese Patent Application No. 2018-558275 (w/ English translation).
Examination Report No. 1 dated Mar. 3, 2022 for Australian Patent Application No. 2017261317.
Official Action dated May 3, 2022 for Israel Patent Application No. 262720 (English translation / summary).
Walpole et al. "The weight of nations: an estimation of adult human biomass," BMC Public Health, 2012, 12:439.
International Search Report and Written Opinion of the International Searching Authority for International Application No. PCT/US2017/031301, dated Jul. 19, 2017.

(Continued)

*Primary Examiner* — Celeste A Roney
(74) *Attorney, Agent, or Firm* — Morgan, Lewis & Bockius LLP

(57) ABSTRACT

A dry powder inhalation treatment for pulmonary arterial hypertension includes a dose of dry particles comprising greater than 25 micrograms of treprostinil enclosed in a capsule. The dry particles can include treprostinil, a wetting agent, a hydrophobicity modifying agent, a pH modifying agent and a buffer. A method of treating a patient having pulmonary arterial hypertension includes providing a patient a dry powder inhaler, providing the patient at least one capsule for use in the dry powder inhaler, the capsule including at least 25 micrograms of treprostinil.

19 Claims, 22 Drawing Sheets

(56) References Cited

U.S. PATENT DOCUMENTS

| | | | |
|---|---|---|---|
| 9,872,864 | B2 | 1/2018 | Sprogoe et al. |
| 9,957,220 | B2 | 5/2018 | Zhang et al. |
| 9,988,644 | B2 | 6/2018 | Heffner et al. |
| 10,016,338 | B2 | 7/2018 | Weikart et al. |
| 10,053,414 | B2 | 8/2018 | Zhang et al. |
| 10,071,123 | B2 | 9/2018 | Jeffs et al. |
| 10,071,209 | B2 | 9/2018 | Shlomo et al. |
| 10,080,804 | B2 | 9/2018 | Rudolph et al. |
| 10,086,001 | B2 | 10/2018 | Freissmuth et al. |
| 10,166,183 | B2 | 1/2019 | Sommer et al. |
| 10,167,247 | B2 | 1/2019 | Phares et al. |
| 10,245,244 | B2 | 4/2019 | Yacoub et al. |
| 10,246,403 | B2 | 4/2019 | Zhang et al. |
| 10,376,525 | B2 | 8/2019 | Olschewski et al. |
| 10,494,327 | B2 | 12/2019 | Laing |
| 10,716,793 | B2 | 7/2020 | Olschewski et al. |
| 10,898,494 | B2 | 1/2021 | Roscigno et al. |
| 10,912,778 | B2 | 2/2021 | Weers et al. |
| 10,995,055 | B2 | 5/2021 | Malinin et al. |
| 2003/0118567 | A1 | 6/2003 | Stewart |
| 2006/0073105 | A1 | 4/2006 | Yamashita et al. |
| 2006/0147520 | A1 | 7/2006 | Ruegg |
| 2008/0131692 | A1 | 6/2008 | Rolland et al. |
| 2008/0200449 | A1 | 8/2008 | Olschewski et al. |
| 2009/0036465 | A1 | 2/2009 | Roscigno et al. |
| 2009/0165320 | A1 | 7/2009 | DeSimone et al. |
| 2009/0264389 | A1 | 10/2009 | Zeng |
| 2010/0003291 | A1 | 1/2010 | Rothrock |
| 2011/0311630 | A1 | 12/2011 | Krueger et al. |
| 2012/0114554 | A1 | 5/2012 | DeSimone et al. |
| 2012/0177693 | A1 | 7/2012 | Cipolla et al. |
| 2012/0189728 | A1 | 7/2012 | Rolland et al. |
| 2012/0256354 | A1 | 10/2012 | DeSimone et al. |
| 2013/0011618 | A1 | 1/2013 | DeSimone et al. |
| 2013/0202729 | A1 | 8/2013 | Rolland et al. |
| 2013/0209564 | A1 | 8/2013 | Rele et al. |
| 2013/0228950 | A1 | 9/2013 | DeSimone et al. |
| 2013/0241107 | A1 | 9/2013 | Ermochkine et al. |
| 2013/0249138 | A1 | 9/2013 | DeSimone et al. |
| 2014/0027948 | A1 | 1/2014 | Henn et al. |
| 2014/0065219 | A1* | 3/2014 | Bosch .............. A61J 3/02 514/304 |
| 2014/0072632 | A1 | 3/2014 | DeSimone et al. |
| 2014/0127227 | A1 | 5/2014 | Chang |
| 2014/0127311 | A1 | 5/2014 | Beck-Broichsitter et al. |
| 2015/0136130 | A1 | 5/2015 | DeHaan et al. |
| 2015/0166503 | A1* | 6/2015 | Becker .............. C07D 263/24 549/267 |
| 2015/0196516 | A1 | 7/2015 | Yacoub et al. |
| 2015/0021690 | A1 | 8/2015 | Jeffs et al. |
| 2015/0246188 | A1 | 9/2015 | Steiner et al. |
| 2015/0273079 | A1 | 10/2015 | Hubby et al. |
| 2015/0328232 | A1 | 11/2015 | Malinin et al. |
| 2016/0045434 | A1 | 2/2016 | Caponetti et al. |
| 2017/0216538 | A1* | 8/2017 | Kinsey .............. A61M 15/0045 |
| 2017/0304276 | A1 | 10/2017 | Armer et al. |
| 2019/0151332 | A1 | 5/2019 | Roscigno et al. |
| 2019/0321290 | A1 | 10/2019 | Guamer et al. |
| 2020/0046917 | A1 | 2/2020 | Kinsey et al. |
| 2021/0022994 | A1 | 1/2021 | Franssen et al. |
| 2021/0077504 | A1 | 3/2021 | Roscigno et al. |
| 2021/0353640 | A1 | 11/2021 | Roscigno et al. |
| 2021/0353641 | A1 | 11/2021 | Roscigno et al. |

FOREIGN PATENT DOCUMENTS

| | | |
|---|---|---|
| JP | 4819224 B2 | 11/2011 |
| JP | 2016-501233 A | 1/2016 |
| WO | 00/54758 A2 | 9/2000 |
| WO | 2005/058303 A1 | 6/2005 |
| WO | 2006/014930 A2 | 2/2006 |
| WO | 2007/134292 A2 | 11/2007 |
| WO | 2009152160 A1 | 12/2009 |
| WO | 2012/095511 A1 | 7/2012 |
| WO | 2014/085813 A1 | 6/2014 |
| WO | 2014/167023 A1 | 10/2014 |
| WO | 2015061720 A2 | 4/2015 |
| WO | 2016/057712 A1 | 4/2016 |
| WO | 2017/132601 A1 | 8/2017 |
| WO | 2019/237028 A1 | 12/2019 |

OTHER PUBLICATIONS

Channick, Richard N. et al. "Inhaled treprostinil: a therapeutic review," Drug Design, Development and Therapy, vol. 6 (2012): 19-28.

Voswinckel, Robert et al. "Favorable Effects of Inhaled Treprostinil in Severe Pulmonary Hypertension: Results From Randomized Controlled Pilot Studies," Journal of the American College of Cardiology, vol. 48, Issue 8 (2006): 1672-1681.

Michael Castagna, PharmD; "TECHNOSPHERE Drug Delivery Platform"; United Therapeutics Corporation UTHR Science Day 2018 (16 pages).

Vijaya Iyer, Phd "Treprostinil Delivered Using Technosphere Portable Inhaler Seen as Safe in Early Clinical Trial"; Pulmonary Hypertension News; Jun. 11, 2018 (10 pages).

"MannKind Successfully Completes Phase 1 Trial of Treprostinil Technosphere for Pulmonary Arterial Hypertension Advancing Development to Next Phase"; Press Release Jun. 7, 2018; MannKind Corporation (2 pages).

Extended European Search Report, dated Feb. 27, 2020, for European Patent Application No. 17793448.6.

Framen, CA, et al., Synthesis and Characterization of Monodisperse Uniformly Shaped Respirable Aerosols, AI Example NGI distribution for active particles (PAH-1R-0943-010) made. The NGI shows beginning of run (A1-red, left bar), middle of run (B1-blue, center bar), end of run (C1-green, right bar). Data obtained using Monodose Model 8 device (95L/min, 2sec).

FIGURE 3A

| Cohort | Subject Alias | Time (h) Treprostinil (ng/mL) | | | | | | | | | | | | | | |
|---|---|---|---|---|---|---|---|---|---|---|---|---|---|---|---|---|
| | | 0.00 | 0.08 | 0.17 | 0.25 | 0.33 | 0.42 | 0.50 | 0.75 | 1.00 | 1.50 | 2.00 | 2.50 | 3.00 | 3.50 | 4.00 | 6.00 | 8.00 |
| Cohort 1 | 1-A | 0.00 | 0.164 | NR | 0.166 | 0.197 | 0.150 | 0.146 | 0.0992 | 0.0553 | 0.0314 | 0.00 | 0.00 | 0.00 | 0.00 | 0.00 | 0.00 | 0.00 |
| | 1-B | 0.00 | 0.243 | 0.251 | 0.266 | 0.326 | 0.268 | 0.278 | 0.136 | 0.124 | 0.0688 | 0.0573 | 0.0292 | 0.0328 | 0.00 | 0.00 | 0.00 | 0.00 |
| | 1-C | 0.00 | 0.200 | 0.272 | 0.412 | 0.414 | 0.251 | 0.176 | 0.139 | 0.108 | 0.0460 | 0.00 | 0.00 | 0.00 | 0.00 | 0.00 | 0.00 | 0.00 |
| | 1-D | 0.00 | 0.474 | 0.493 | 0.458 | 0.443 | 0.511 | 0.383 | 0.258 | 0.138 | 0.0629 | 0.00 | 0.00 | 0.00 | 0.00 | 0.00 | 0.00 | 0.00 |
| | 1-E | 0.00 | 0.200 | 0.28 | 0.224 | 0.255 | 0.172 | 0.148 | 0.114 | 0.105 | 0.0519 | 0.0308 | 0.00 | 0.00 | 0.00 | 0.00 | 0.00 | 0.00 |
| | 1-F | 0.00 | 0.402 | NR | 0.456 | 0.427 | 0.313 | 0.265 | 0.188 | 0.106 | 0.0483 | 0.00 | 0.00 | 0.00 | 0.00 | 0.00 | 0.00 | 0.00 |
| | N | 6 | 6 | 4 | 6 | 6 | 6 | 6 | 6 | 6 | 6 | 6 | 6 | 6 | 6 | 6 | 6 | 6 |
| | Mean | 0.00 | 0.281 | 0.324 | 0.330 | 0.344 | 0.278 | 0.233 | 0.156 | 0.106 | 0.0516 | 0.0147 | 0.00487 | 0.00547 | 0.00 | 0.00 | 0.00 | 0.00 |
| | SD | 0.00 | 0.127 | 0.113 | 0.127 | 0.101 | 0.130 | 0.0934 | 0.0585 | 0.028 | 0.0132 | 0.0242 | 0.0119 | 0.0134 | 0.00 | 0.00 | 0.00 | 0.00 |
| | Min | 0.00 | 0.164 | 0.251 | 0.166 | 0.197 | 0.150 | 0.146 | 0.0992 | 0.0553 | 0.0314 | 0.00 | 0.00 | 0.00 | 0.00 | 0.00 | 0.00 | 0.00 |
| | Median | 0.00 | 0.222 | 0.276 | 0.339 | 0.370 | 0.260 | 0.221 | 0.138 | 0.107 | 0.0501 | 0.00 | 0.00 | 0.00 | 0.00 | 0.00 | 0.00 | 0.00 |
| | Max | 0.00 | 0.474 | 0.493 | 0.458 | 0.443 | 0.511 | 0.383 | 0.258 | 0.138 | 0.0688 | 0.0573 | 0.0292 | 0.0328 | 0.00 | 0.00 | 0.00 | 0.00 |
| | CV% | NC | 45.1 | 35.0 | 38.6 | 29.5 | 46.7 | 40.1 | 37.6 | 26.4 | 25.6 | 165.1 | 244.9 | 244.9 | NC | NC | NC | NC |

NC = Not calculated; NR = Not Reported

FIGURE 3B

| Cohort | Subject Alias | Cmax (ng/mL) | Tmax (h) | t½ (h) | AUClast (h*ng/mL) | AUCinf (h*ng/mL) | CL/F (L/h) | Vz/F (L) |
|---|---|---|---|---|---|---|---|---|
| Cohort 1 | 1-A | 0.197 | 0.33 | 0.454 | 0.146 | 0.167 | 150 | 98.2 |
| | 1-B | 0.326 | 0.33 | 0.795 | 0.321 | 0.359 | 69.7 | 80.0 |
| | 1-C | 0.414 | 0.33 | 0.460 | 0.242 | 0.272 | 91.8 | 60.9 |
| | 1-D | 0.511 | 0.42 | 0.377 | 0.389 | 0.423 | 59.1 | 32.1 |
| | 1-E | 0.280 | 0.17 | 0.648 | 0.218 | 0.247 | 101 | 94.7 |
| | 1-F | 0.456 | 0.25 | 0.399 | 0.308 | 0.336 | 74.4 | 42.8 |
| | N | 6 | 6 | 6 | 6 | 6 | 6 | 6 |
| | Mean | 0.364 | 0.306 | 0.522 | 0.271 | 0.301 | 91.0 | 68.1 |
| | SD | 0.117 | 0.086 | 0.164 | 0.086 | 0.091 | 32.6 | 27.4 |
| | Min | 0.20 | 0.17 | 0.38 | 0.15 | 0.17 | 59.1 | 32.1 |
| | Median | 0.37 | 0.33 | 0.46 | 0.28 | 0.30 | 83.1 | 70.4 |
| | Max | 0.51 | 0.42 | 0.80 | 0.39 | 0.42 | 150 | 98.2 |
| | CV% | 32.3 | 28.2 | 31.5 | 31.8 | 30.2 | 35.8 | 40.2 |
| | Geometric Mean | 0.347 | 0.294 | 0.503 | 0.258 | 0.288 | 86.8 | 63.0 |
| | CV% Geometric Mean | 36.52 | 33.02 | 29.96 | 35.77 | 33.91 | 33.9 | 47.67 |

FIGURE 4A

| Cohort | Subject Alias | Time (h) Treprostinil (ng/mL) | | | | | | | | | | | | | | | |
|---|---|---|---|---|---|---|---|---|---|---|---|---|---|---|---|---|---|
| | | 0.00 | 0.08 | 0.17 | 0.25 | 0.33 | 0.42 | 0.50 | 0.75 | 1.00 | 1.50 | 2.00 | 2.50 | 3.00 | 3.50 | 4.00 | 6.00 | 8.00 |
| Cohort 2 | 2-A | 0.00 | NR | 0.99 | 0.93 | 0.77 | 0.70 | 0.58 | 0.37 | 0.30 | 0.12 | 0.08 | 0.03 | 0.00 | 0.00 | 0.00 | 0.00 | 0.00 |
| | 2-B | 0.00 | 0.94 | 1.03 | 0.95 | 0.83 | 0.64 | 0.41 | 0.30 | 0.18 | 0.09 | 0.05 | 0.03 | 0.03 | 0.00 | 0.00 | 0.00 | 0.00 |
| | 2-C | 0.00 | 0.48 | 0.41 | 0.32 | 0.31 | 0.26 | 0.22 | 0.13 | 0.08 | 0.04 | 0.00 | 0.00 | 0.00 | 0.00 | 0.00 | 0.00 | 0.00 |
| | 2-D | 0.00 | 0.45 | 0.53 | 0.50 | 0.46 | 0.45 | 0.44 | 0.30 | 0.22 | 0.08 | 0.04 | 0.00 | 0.00 | 0.00 | 0.00 | 0.00 | 0.00 |
| | 2-E | 0.00 | 0.28 | 0.29 | 0.26 | 0.23 | 0.21 | 0.20 | 0.13 | 0.08 | 0.04 | 0.00 | 0.00 | 0.00 | 0.00 | 0.00 | 0.00 | 0.00 |
| | 2-F | 0.00 | 0.00 | 0.09 | 0.11 | 0.11 | 0.12 | 0.11 | 0.06 | 0.03 | 0.00 | 0.00 | 0.00 | 0.00 | 0.00 | 0.00 | 0.00 | 0.00 |
| | N | 6 | 5 | 6 | 6 | 6 | 6 | 6 | 6 | 6 | 6 | 6 | 6 | 6 | 6 | 6 | 6 | 6 |
| | Mean | 0.00 | 0.429 | 0.556 | 0.511 | 0.452 | 0.395 | 0.326 | 0.214 | 0.149 | 0.0624 | 0.0277 | 0.0108 | 0.00507 | 0.00 | 0.00 | 0.00 | 0.00 |
| | SD | 0.00 | 0.342 | 0.382 | 0.355 | 0.295 | 0.240 | 0.180 | 0.123 | 0.101 | 0.0433 | 0.0333 | 0.0168 | 0.0124 | 0.00 | 0.00 | 0.00 | 0.00 |
| | Min | 0.00 | 0.00 | 0.0853 | 0.111 | 0.108 | 0.116 | 0.110 | 0.0600 | 0.0270 | 0.00 | 0.00 | 0.00 | 0.00 | 0.00 | 0.00 | 0.00 | 0.00 |
| | Median | 0.00 | 0.453 | 0.470 | 0.410 | 0.385 | 0.351 | 0.313 | 0.216 | 0.134 | 0.0603 | 0.0186 | 0.00 | 0.00 | 0.00 | 0.00 | 0.00 | 0.00 |
| | Max | 0.00 | 0.937 | 1.03 | 0.948 | 0.833 | 0.703 | 0.583 | 0.367 | 0.298 | 0.124 | 0.0794 | 0.0332 | 0.0304 | 0.00 | 0.00 | 0.00 | 0.00 |
| | CV% | NC | 79.7 | 68.8 | 69.4 | 65.1 | 60.8 | 55.2 | 57.6 | 68.1 | 69.3 | 120.3 | 155.0 | 244.9 | NC | NC | NC | NC |

NC= Not calculated; NR = Not Reported

FIGURE 4B

| Cohort | Subject | Cmax (ng/mL) | Tmax (h) | t½ (h) | AUClast (h*ng/mL) | AUCinf (h*ng/mL) | CL/F (L/h) | Vz/F (L) |
|---|---|---|---|---|---|---|---|---|
| Cohort 2 | 2-A | 0.991 | 0.17 | 0.482 | 0.723 | 0.746 | 67.0 | 46.6 |
| | 2-B | 1.03 | 0.17 | 0.624 | 0.663 | 0.690 | 72.5 | 65.2 |
| | 2-C | 0.477 | 0.08 | 0.474 | 0.254 | 0.282 | 177 | 121 |
| | 2-D | 0.530 | 0.17 | 0.410 | 0.466 | 0.488 | 102 | 60.5 |
| | 2-E | 0.288 | 0.17 | 0.478 | 0.212 | 0.242 | 206 | 142 |
| | 2-F | 0.116 | 0.42 | 0.247 | 0.0706 | 0.0802 | 624 | 222 |
| | N | 6 | 6 | 6 | 6 | 6 | 6 | 6 |
| | Mean | 0.572 | 0.195 | 0.452 | 0.398 | 0.422 | 208 | 110 |
| | SD | 0.370 | 0.114 | 0.123 | 0.262 | 0.265 | 211 | 66.6 |
| | Min | 0.116 | 0.0830 | 0.247 | 0.0706 | 0.0802 | 67.0 | 46.6 |
| | Median | 0.504 | 0.167 | 0.476 | 0.360 | 0.385 | 140 | 93.3 |
| | Max | 1.03 | 0.417 | 0.624 | 0.723 | 0.746 | 624 | 222 |
| | CV% | 64.7 | 58.6 | 27.2 | 65.8 | 62.8 | 101.5 | 60.7 |
| | Geometric Mean | 0.453 | 0.173 | 0.436 | 0.308 | 0.334 | 150 | 94.3 |
| | CV% Geometric Mean | 98.2 | 54.9 | 31.8 | 107.4 | 100.4 | 100.4 | 65.7 |

FIGURE 5A

| Cohort | Subject Alias | NTime (h) | | | | | | | | | | | | | | |
|---|---|---|---|---|---|---|---|---|---|---|---|---|---|---|---|---|
| | | 0.00 | 0.08 | 0.17 | 0.25 | 0.33 | 0.42 | 0.50 | 0.75 | 1.00 | 1.50 | 2.00 | 2.50 | 3.00 | 3.50 | 4.00 | 6.00 | 8.00 |
| | | | | | | | | Treprostinil (ng/mL) | | | | | | | | |
| Cohort 3 | 3-A | 0.00 | 0.63 | 0.62 | 0.55 | 0.47 | 0.43 | 0.42 | 0.32 | 0.21 | 0.11 | 0.06 | 0.03 | 0.00 | 0.00 | 0.00 | 0.00 | 0.00 |
| | 3-B | 0.00 | 0.44 | 0.52 | 0.51 | 0.51 | 0.53 | 0.47 | 0.39 | 0.26 | 0.13 | 0.12 | 0.03 | 0.00 | 0.00 | 0.00 | 0.00 | 0.00 |
| | 3-C | 0.00 | 0.75 | 1.07 | 1.11 | 1.01 | NR | 0.80 | 0.47 | 0.35 | 0.14 | 0.07 | 0.05 | 0.03 | 0.00 | 0.00 | 0.00 | 0.00 |
| | 3-D | 0.00 | NR | 0.40 | 0.43 | 0.40 | 0.37 | 0.34 | 0.29 | 0.20 | 0.10 | 0.05 | 0.00 | 0.00 | 0.00 | 0.00 | 0.00 | 0.00 |
| | 3-E | 0.00 | 0.45 | 0.52 | 0.54 | 0.57 | 0.54 | 0.48 | 0.36 | 0.28 | 0.15 | 0.11 | 0.03 | 0.00 | 0.00 | 0.00 | 0.00 | 0.00 |
| | 3-F | 0.00 | 0.94 | 1.05 | 1.10 | 1.10 | 1.07 | 1.03 | 0.80 | 0.53 | 0.30 | 0.15 | 0.07 | 0.04 | 0.00 | 0.00 | 0.00 | 0.00 |
| | N | 6 | 5 | 6 | 6 | 6 | 5 | 6 | 6 | 6 | 6 | 6 | 6 | 6 | 6 | 6 | 6 | 6 |
| | Mean | 0.00 | 0.641 | 0.697 | 0.706 | 0.677 | 0.587 | 0.591 | 0.437 | 0.304 | 0.155 | 0.0951 | 0.0349 | 0.0124 | 0.00 | 0.00 | 0.00 | 0.00 |
| | SD | 0.00 | 0.209 | 0.290 | 0.312 | 0.299 | 0.279 | 0.267 | 0.187 | 0.123 | 0.0755 | 0.0389 | 0.0225 | 0.0192 | 0.00 | 0.00 | 0.00 | 0.00 |
| | Min | 0.00 | 0.437 | 0.399 | 0.428 | 0.400 | 0.371 | 0.344 | 0.285 | 0.199 | 0.0976 | 0.0547 | 0.00 | 0.00 | 0.00 | 0.00 | 0.00 | 0.00 |
| | Median | 0.00 | 0.630 | 0.571 | 0.545 | 0.540 | 0.532 | 0.474 | 0.379 | 0.269 | 0.136 | 0.0916 | 0.0342 | 0.00 | 0.00 | 0.00 | 0.00 | 0.00 |
| | Max | 0.00 | 0.936 | 1.07 | 1.11 | 1.10 | 1.07 | 1.03 | 0.796 | 0.529 | 0.304 | 0.149 | 0.0682 | 0.0395 | 0.00 | 0.00 | 0.00 | 0.00 |
| | CV% | NC | 32.6 | 41.7 | 44.2 | 44.2 | 47.5 | 45.2 | 42.8 | 40.5 | 48.8 | 40.9 | 64.6 | 155.4 | NC | NC | NC | NC |

NC = Not calculated; NR = Not Reported

FIGURE 5B

| Cohort | Subject Alias | Cmax (ng/mL) | Tmax (h) | t½ (h) | AUClast (h*ng/mL) | AUCinf (h*ng/mL) | CL/F (L/h) | Vz/F (L) |
|---|---|---|---|---|---|---|---|---|
| Cohort 3 | 3-A | 0.630 | 0.08 | 0.609 | 0.538 | 0.568 | 132 | 116 |
| | 3-B | 0.532 | 0.42 | 0.568 | 0.611 | 0.638 | 118 | 96.3 |
| | 3-C | 1.11 | 0.25 | 0.980 | 0.906 | 0.955 | 78.5 | 111 |
| | 3-D | 0.428 | 0.25 | 0.522 | 0.411 | 0.452 | 166 | 125 |
| | 3-E | 0.567 | 0.33 | 0.531 | 0.619 | 0.639 | 117 | 89.9 |
| | 3-F | 1.10 | 0.25 | 0.520 | 1.26 | 1.29 | 58.1 | 43.6 |
| | N | 6 | 6 | 6 | 6 | 6 | 6 | 6 |
| | Mean | 0.728 | 0.264 | 0.622 | 0.724 | 0.757 | 112 | 97.0 |
| | SD | 0.299 | 0.111 | 0.179 | 0.309 | 0.310 | 38.5 | 29.1 |
| | Min | 0.428 | 0.0833 | 0.520 | 0.411 | 0.452 | 58.1 | 43.6 |
| | Median | 0.599 | 0.250 | 0.550 | 0.615 | 0.639 | 117 | 104 |
| | Max | 1.11 | 0.417 | 0.980 | 1.26 | 1.29 | 166 | 125 |
| | CV% | 41.1 | 42.0 | 28.7 | 42.7 | 41.0 | 34.5 | 30.0 |
| | Geometric Mean | 0.681 | 0.238 | 0.605 | 0.676 | 0.711 | 106 | 92.1 |
| | CV% Geometric Mean | 41.2 | 60.0 | 24.8 | 41.5 | 39.4 | 39.4 | 40.0 |

FIGURE 6A

| Cohort | Subject | NTime (h) Treprostinil (ng/mL) | | | | | | | | | | | | | | | |
|---|---|---|---|---|---|---|---|---|---|---|---|---|---|---|---|---|---|
| | | 0.00 | 0.08 | 0.17 | 0.25 | 0.33 | 0.42 | 0.50 | 0.75 | 1.00 | 1.50 | 2.00 | 2.50 | 3.00 | 3.50 | 4.00 | 6.00 | 8.00 |
| Cohort 4 | 4-A | 0.00 | 0.294 | 0.534 | 0.648 | 0.684 | 0.722 | 0.763 | 0.575 | 0.358 | 0.150 | 0.0789 | 0.0523 | 0.0332 | 0.00 | 0.00 | 0.00 | 0.00 |
| | 4-B | 0.00 | 0.629 | 0.872 | 0.959 | 1.04 | 1.02 | 0.924 | 0.622 | 0.495 | 0.273 | 0.144 | 0.0710 | 0.0449 | 0.0300 | 0.00 | 0.00 | 0.00 |
| | 4-C | 0.00 | 0.552 | 0.725 | 0.704 | 0.718 | 0.688 | 0.729 | 0.625 | 0.557 | 0.346 | 0.205 | 0.143 | 0.0908 | 0.0445 | 0.0286 | 0.00 | 0.00 |
| | 4-D | 0.00 | 1.30 | 1.54 | 1.44 | 1.35 | 1.29 | 1.08 | 0.790 | 0.559 | 0.290 | 0.134 | 0.0709 | 0.0728 | 0.0333 | 0.00 | 0.00 | 0.00 |
| | 4-E | 0.00 | 0.877 | 1.14 | 1.16 | 1.14 | 0.969 | 0.970 | 0.657 | 0.513 | 0.270 | 0.166 | 0.0968 | 0.0524 | 0.0367 | 0.0256 | 0.00 | 0.00 |
| | 4-F | 0.00 | 1.13 | 1.21 | 1.23 | 1.09 | 0.915 | 0.826 | 0.662 | 0.521 | 0.253 | 0.125 | 0.140 | 0.0698 | 0.0324 | 0.0837 | 0.00 | 0.00 |
| | N | 6 | 6 | 6 | 6 | 6 | 6 | 6 | 6 | 6 | 6 | 6 | 6 | 6 | 6 | 6 | 6 | 6 |
| | Mean | 0.00 | 0.797 | 1.00 | 1.02 | 1.00 | 0.934 | 0.882 | 0.655 | 0.501 | 0.264 | 0.142 | 0.0957 | 0.0607 | 0.0295 | 0.0230 | 0.00 | 0.00 |
| | SD | 0.00 | 0.377 | 0.365 | 0.310 | 0.257 | 0.220 | 0.134 | 0.0730 | 0.0742 | 0.0642 | 0.0422 | 0.0382 | 0.0210 | 0.0153 | 0.0326 | 0.00 | 0.00 |
| | Min | 0.00 | 0.294 | 0.534 | 0.648 | 0.684 | 0.688 | 0.729 | 0.575 | 0.358 | 0.150 | 0.0789 | 0.0523 | 0.0332 | 0.00 | 0.00 | 0.00 | 0.00 |
| | Median | 0.00 | 0.753 | 1.01 | 1.06 | 1.07 | 0.942 | 0.875 | 0.641 | 0.517 | 0.272 | 0.139 | 0.0839 | 0.0611 | 0.0329 | 0.0128 | 0.00 | 0.00 |
| | Max | 0.00 | 1.30 | 1.54 | 1.44 | 1.35 | 1.29 | 1.08 | 0.790 | 0.559 | 0.346 | 0.205 | 0.143 | 0.0908 | 0.0445 | 0.0837 | 0.00 | 0.00 |
| | CV% | NC | 47.3 | 36.3 | 30.3 | 25.6 | 23.5 | 15.2 | 11.1 | 14.8 | 24.4 | 29.7 | 40.0 | 34.7 | 51.9 | 141.8 | NC | NC |

NC = Not calculated

FIGURE 6B

| Cohort | Subject | Cmax (ng/mL) | Tmax (h) | t½ (h) | AUClast (h*ng/mL) | AUCinf (h*ng/mL) | CL/F (L/h) | Vz/F (L) |
|---|---|---|---|---|---|---|---|---|
| Cohort 4 | 4-A | 0.763 | 0.50 | 0.801 | 0.781 | 0.819 | 122 | 141 |
| | 4-B | 1.04 | 0.33 | 0.805 | 1.13 | 1.17 | 85.8 | 99.6 |
| | 4-C | 0.729 | 0.50 | 0.702 | 1.18 | 1.21 | 82.8 | 83.8 |
| | 4-D | 1.54 | 0.17 | 0.583 | 1.44 | 1.46 | 68.3 | 57.4 |
| | 4-E | 1.16 | 0.25 | 0.968 | 1.26 | 1.30 | 77.1 | 108 |
| | 4-F | 1.23 | 0.25 | 0.794 | 1.28 | 1.37 | 72.8 | 83.4 |
| | N | 6 | 6 | 6 | 6 | 6 | 6 | 6 |
| | Mean | 1.08 | 0.333 | 0.775 | 1.18 | 1.22 | 84.8 | 95.5 |
| | SD | 0.305 | 0.139 | 0.127 | 0.221 | 0.225 | 19.3 | 28.2 |
| | Min | 0.729 | 0.167 | 0.583 | 0.781 | 0.819 | 68.3 | 57.4 |
| | Median | 1.10 | 0.292 | 0.798 | 1.22 | 1.25 | 79.9 | 91.7 |
| | Max | 1.54 | 0.500 | 0.968 | 1.44 | 1.46 | 122 | 141 |
| | CV% | 28.3 | 41.8 | 16.4 | 18.7 | 18.4 | 22.8 | 29.5 |
| | Geometric Mean | 1.04 | 0.309 | 0.766 | 1.16 | 1.20 | 83.2 | 92.0 |
| | CV% Geometric Mean | 29.5 | 45.5 | 17.0 | 21.2 | 20.7 | 20.7 | 30.8 |

FIGURE 7A

| Cohort | Subject | NTime (h) | | | | | | | | | | | | | | |
|---|---|---|---|---|---|---|---|---|---|---|---|---|---|---|---|---|
| | | 0.00 | 0.08 | 0.17 | 0.25 | 0.33 | 0.42 | 0.50 | 0.75 | 1.00 | 1.50 | 2.00 | 2.50 | 3.00 | 3.50 | 4.00 | 6.00 | 8.00 |
| | | | | | | | | | | Treprostinil (ng/mL) | | | | | | | | |
| Cohort 5 | 5-A | 0.00 | 1.13 | 1.96 | 1.80 | 1.64 | 1.54 | 1.38 | 0.971 | 0.752 | 0.394 | 0.238 | 0.136 | 0.0833 | 0.0583 | 0.0345 | 0.00 | 0.00 |
| | 5-B | 0.00 | 0.562 | 1.26 | 1.26 | 1.45 | 1.40 | 1.24 | 0.876 | 0.605 | 0.312 | 0.195 | 0.0732 | 0.0351 | 0.00 | 0.00 | 0.00 | 0.00 |
| | 5-C | 0.00 | 0.478 | 0.763 | 0.979 | 1.02 | 0.976 | 0.909 | NR | 0.409 | 0.294 | 0.128 | 0.0658 | 0.0433 | 0.00 | 0.00 | 0.00 | 0.00 |
| | 5-D | 0.00 | 1.04 | 1.42 | 1.26 | 1.08 | 1.02 | 0.824 | 0.635 | 0.467 | 0.252 | 0.146 | 0.0615 | 0.0304 | 0.00 | 0.00 | 0.00 | 0.00 |
| | 5-E | 0.00 | 0.543 | 0.728 | 0.730 | 0.743 | 0.754 | 0.699 | 0.502 | 0.397 | 0.230 | 0.113 | 0.0500 | 0.0262 | 0.00 | 0.00 | 0.00 | 0.00 |
| | 5-F | 0.00 | 0.502 | 0.510 | 0.427 | 0.399 | 0.333 | 0.265 | 0.201 | 0.120 | 0.0565 | 0.0306 | 0.00 | 0.00 | 0.00 | 0.00 | 0.00 | 0.00 |
| | N | 6 | 6 | 6 | 6 | 6 | 6 | 6 | 5 | 6 | 6 | 6 | 6 | 6 | 6 | 6 | 6 | 6 |
| | Mean | 0.00 | 0.709 | 1.11 | 1.08 | 1.06 | 1.00 | 0.886 | 0.637 | 0.458 | 0.256 | 0.142 | 0.0644 | 0.0364 | 0.00972 | 0.00575 | 0.00 | 0.00 |
| | SD | 0.00 | 0.294 | 0.542 | 0.478 | 0.453 | 0.438 | 0.399 | 0.307 | 0.214 | 0.113 | 0.0714 | 0.0437 | 0.0273 | 0.0238 | 0.0141 | 0.00 | 0.00 |
| | Min | 0.00 | 0.478 | 0.510 | 0.427 | 0.399 | 0.333 | 0.265 | 0.201 | 0.120 | 0.0565 | 0.0306 | 0.00 | 0.00 | 0.00 | 0.00 | 0.00 | 0.00 |
| | Median | 0.00 | 0.553 | 1.01 | 1.12 | 1.05 | 0.998 | 0.867 | 0.635 | 0.438 | 0.273 | 0.137 | 0.0637 | 0.0328 | 0.00 | 0.00 | 0.00 | 0.00 |
| | Max | 0.00 | 1.13 | 1.96 | 1.80 | 1.64 | 1.54 | 1.38 | 0.971 | 0.752 | 0.394 | 0.238 | 0.136 | 0.0833 | 0.0583 | 0.0345 | 0.00 | 0.00 |
| | CV% | NC | 41.5 | 48.9 | 44.4 | 43.0 | 43.6 | 45.0 | 48.2 | 46.6 | 44.2 | 50.4 | 67.9 | 74.9 | 244.9 | 244.9 | NC | NC |

NC = Not calculated; NR = Not Reported

FIGURE 7B

| Cohort | Subject | Cmax (ng/mL) | Tmax (h) | t½ (h) | AUClast (h*ng/mL) | AUCinf (h*ng/mL) | CL/F (L/h) | Vz/F (L) |
|---|---|---|---|---|---|---|---|---|
| Cohort 5 | 5-A | 1.96 | 0.17 | 0.647 | 1.87 | 1.90 | 65.7 | 61.3 |
| | 5-B | 1.45 | 0.33 | 0.495 | 1.42 | 1.45 | 86.2 | 61.6 |
| | 5-C | 1.02 | 0.33 | 0.561 | 1.05 | 1.08 | 115 | 93.3 |
| | 5-D | 1.42 | 0.17 | 0.526 | 1.18 | 1.20 | 104 | 78.9 |
| | 5-E | 0.754 | 0.42 | 0.473 | 0.874 | 0.891 | 140 | 95.6 |
| | 5-F | 0.510 | 0.17 | 0.448 | 0.352 | 0.372 | 336 | 217 |
| | N | 6 | 6 | 6 | 6 | 6 | 6 | 6 |
| | Mean | 1.19 | 0.264 | 0.525 | 1.12 | 1.15 | 141 | 101 |
| | SD | 0.528 | 0.111 | 0.0716 | 0.512 | 0.516 | 98.8 | 58.7 |
| | Min | 0.510 | 0.167 | 0.448 | 0.352 | 0.372 | 65.7 | 61.3 |
| | Median | 1.22 | 0.250 | 0.511 | 1.11 | 1.14 | 110 | 86.1 |
| | Max | 1.96 | 0.417 | 0.647 | 1.87 | 1.90 | 336 | 217 |
| | CV% | 44.5 | 42.0 | 13.6 | 45.6 | 44.9 | 69.9 | 57.9 |
| | Geometric Mean | 1.08 | 0.245 | 0.521 | 1.00 | 1.03 | 121 | 91.3 |
| | CV% Geometric Mean | 52.4 | 44.9 | 13.2 | 62.6 | 60.9 | 60.9 | 49.3 |

FIGURE 8A

| Cohort | Subject | NTime (h) | | | | | | | | | | | | | | |
|---|---|---|---|---|---|---|---|---|---|---|---|---|---|---|---|---|
| | | 0.00 | 0.08 | 0.17 | 0.25 | 0.33 | 0.42 | 0.50 | 0.75 | 1.00 | 1.50 | 2.00 | 2.50 | 3.00 | 3.50 | 4.00 | 6.00 | 8.00 |
| | | Treprostinil (ng/mL) | | | | | | | | | | | | | | | | |
| Cohort 6-R | 6-A | 0.00 | 0.244 | 0.474 | 0.596 | 0.622 | 0.704 | 0.61 | 0.459 | 0.345 | 0.177 | 0.085 | 0.0387 | 0.00 | 0.00 | 0.00 | 0.00 | 0.00 |
| | 6-B | 0.00 | 0.877 | 0.907 | 0.75 | 0.657 | 0.538 | 0.459 | 0.287 | 0.166 | 0.0915 | 0.0488 | 0.00 | 0.00 | 0.00 | 0.00 | 0.00 | 0.00 |
| | 6-C | 0.00 | 0.547 | 1.47 | 1.68 | 1.67 | 1.59 | 1.41 | 1.00 | 0.762 | 0.406 | 0.232 | 0.144 | 0.0885 | 0.0603 | 0.0376 | 0.00 | 0.00 |
| | 6-D | 0.00 | 1.41 | 1.7 | 1.89 | 1.86 | 1.75 | 1.69 | 1.24 | 0.9 | 0.463 | 0.22 | 0.116 | 0.0673 | 0.0758 | 0.0404 | 0.00 | 0.00 |
| | 6-E | 0.00 | 1.21 | 1.83 | 2.12 | 2.34 | 2.06 | 1.9 | 1.65 | 1.25 | 0.699 | 0.431 | 0.244 | 0.14 | 0.106 | 0.093 | 0.00 | 0.00 |
| | 6-F | 0.00 | 0.615 | 0.938 | 1.09 | 1.19 | 1.12 | 1.11 | 0.912 | 0.682 | 0.412 | 0.207 | 0.122 | 0.0677 | 0.0502 | 0.0325 | 0.00 | 0.00 |
| | N | 6 | 6 | 6 | 6 | 6 | 6 | 6 | 6 | 6 | 6 | 6 | 6 | 6 | 6 | 6 | 6 | 6 |
| | Mean | 0.00 | 0.817 | 1.22 | 1.35 | 1.39 | 1.29 | 1.2 | 0.925 | 0.684 | 0.375 | 0.204 | 0.111 | 0.0606 | 0.0487 | 0.0339 | 0.00 | 0.00 |
| | SD | 0.00 | 0.436 | 0.529 | 0.631 | 0.688 | 0.605 | 0.58 | 0.501 | 0.389 | 0.217 | 0.135 | 0.0854 | 0.0539 | 0.0422 | 0.0342 | 0.00 | 0.00 |
| | Min | 0.00 | 0.244 | 0.474 | 0.596 | 0.622 | 0.538 | 0.459 | 0.287 | 0.166 | 0.0915 | 0.0488 | 0.00 | 0.00 | 0.00 | 0.00 | 0.00 | 0.00 |
| | Median | 0.00 | 0.746 | 1.20 | 1.39 | 1.43 | 1.36 | 1.26 | 0.956 | 0.722 | 0.409 | 0.214 | 0.119 | 0.0675 | 0.0553 | 0.0351 | 0.00 | 0.00 |
| | Max | 0.00 | 1.41 | 1.83 | 2.12 | 2.34 | 2.06 | 1.90 | 1.65 | 1.25 | 0.699 | 0.431 | 0.244 | 0.14 | 0.106 | 0.093 | 0.00 | 0.00 |
| | CV% | NC | 53.4 | 43.4 | 46.6 | 49.5 | 46.8 | 48.4 | 54.2 | 56.8 | 57.8 | 66.1 | 77.1 | 89 | 86.6 | 100.8 | NC | NC |

NC= Not calculated; NR = Not Reported

FIGURE 8B

| Cohort | Subject | Cmax (ng/mL) | Tmax (h) | t½ (h) | AUClast (h*ng/mL) | AUCinf (h*ng/mL) | CL/F (L/h) | Vz/F (L) |
|---|---|---|---|---|---|---|---|---|
| Cohort 6-R | 6-A | 0.704 | 0.42 | 0.456 | 0.696 | 0.721 | 208 | 137 |
| | 6-B | 0.907 | 0.17 | 0.566 | 0.573 | 0.613 | 245 | 200 |
| | 6-C | 1.68 | 0.25 | 0.768 | 1.80 | 1.85 | 81.3 | 90.1 |
| | 6-E | 1.89 | 0.25 | 0.628 | 2.10 | 2.13 | 70.3 | 63.6 |
| | 6-F | 2.34 | 0.33 | 0.734 | 2.80 | 2.90 | 51.8 | 54.9 |
| | 6-G | 1.19 | 0.33 | 0.665 | 1.50 | 1.53 | 97.9 | 93.8 |
| | N | 6 | 6 | 6 | 6 | 6 | 6 | 6 |
| | Mean | 1.45 | 0.292 | 0.636 | 1.58 | 1.62 | 126 | 107 |
| | SD | 0.626 | 0.087 | 0.114 | 0.849 | 0.869 | 80.3 | 54.0 |
| | Min | 0.704 | 0.167 | 0.456 | 0.573 | 0.613 | 51.8 | 54.9 |
| | Median | 1.44 | 0.292 | 0.646 | 1.65 | 1.69 | 89.6 | 92.0 |
| | Max | 2.34 | 0.417 | 0.768 | 2.8 | 2.90 | 245 | 200 |
| | CV% | 43.1 | 30.0 | 18.0 | 53.8 | 53.5 | 63.9 | 50.7 |
| | Geometric Mean | 1.33 | 0.28 | 0.627 | 1.36 | 1.41 | 107 | 96.5 |
| | CV% Geometric Mean | 48.6 | 32.9 | 19.2 | 70 | 68.3 | 68.3 | 50.9 |

FIGURE 8C

| Cohort | Subject | Cmax (ng/mL) | Tmax (h) | t½ (h) | AUClast (h*ng/mL) | AUCinf (h*ng/mL) | CL/F (L/h) | Vz/F (L) |
|---|---|---|---|---|---|---|---|---|
| Cohort 6 - Original | 6-A (ORIGINAL) | 1.55 | 0.33 | 0.607 | 1.96 | 1.99 | 75.6 | 66.2 |
| | 6-B (ORIGINAL) | 1.16 | 0.08 | 0.946 | 0.868 | 0.987 | 152 | 208 |
| | 6-C (ORIGINAL) | 1.17 | 0.42 | 0.534 | 1.28 | 1.30 | 115 | 88.9 |
| | 6-D (ORIGINAL) | 0.968 | 0.42 | 0.649 | 1.30 | 1.33 | 113 | 105 |
| | 6-E (ORIGINAL) | 1.55 | 0.17 | 0.658 | 1.68 | 1.71 | 87.9 | 83.5 |
| | 6-F (ORIGINAL) | 0.835 | 0.25 | 0.565 | 0.871 | 0.891 | 168 | 137 |
| | N | 6 | 6 | 6 | 6 | 6 | 6 | 6 |
| | Mean | 1.21 | 0.278 | 0.660 | 1.33 | 1.37 | 119 | 115 |
| | SD | 0.295 | 0.136 | 0.148 | 0.435 | 0.418 | 35.8 | 51.4 |
| | Min | 0.835 | 0.0833 | 0.534 | 0.868 | 0.891 | 75.6 | 66.2 |
| | Median | 1.17 | 0.292 | 0.628 | 1.29 | 1.32 | 114 | 97.2 |
| | Max | 1.55 | 0.417 | 0.946 | 1.96 | 1.99 | 168 | 208 |
| | CV% | 24.4 | 49.0 | 22.5 | 32.8 | 30.6 | 30.2 | 44.8 |
| | Geometric Mean | 1.18 | 0.242 | 0.648 | 1.27 | 1.31 | 114 | 107 |
| | Geometric CV% | 25.2 | 69.5 | 20.4 | 34.2 | 31.4 | 31.4 | 42.4 |

RS00 Model 8 Dry Powder Inhalation Device

DRY POWDER TREPROSTINIL FOR THE TREATMENT OF PULMONARY HYPERTENSION

CROSS-REFERENCE TO RELATED APPLICATIONS

This application is continuation of U.S. patent application Ser. No. 17/104,348, filed Nov. 25, 2020, which is a continuation of U.S. patent application Ser. No. 16/099,135 (now U.S. Pat. No. 10,898,494), filed May 5, 2017, which is a U.S. national stage of International Application No. PCT/US2017/031301, filed May 5, 2017, which claims priority to and the benefit of U.S. Provisional Patent Application No. 62/332,013, filed May 5, 2016, U.S. Provisional Patent Application No. 62/404,960, filed Oct. 6, 2016, U.S. Provisional Patent Application No. 62/440,078, filed Dec. 29, 2016, and U.S. Provisional Patent Application No. 62/472,204, filed Mar. 16, 2017, all of which are incorporated herein by reference in their entireties.

TECHNICAL FIELD

The present invention provides an improvement to the treatment of pulmonary hypertension, a condition that deteriorates the lives of many thousands of patients toward an untimely death. The present invention provides, for the first time, a stable, user friendly, uniform dry powder inhaled treprostinil formulation, methods of making, and use thereof in humans.

BACKGROUND

Pulmonary arterial hypertension (PAH) is a complex, multifactorial, progressive, and life-threatening disease characterized by proliferative and obstructive changes in the pulmonary vasculature and involving numerous biochemical pathways and cell types. The disease is characterized by elevated pulmonary arterial pressure caused by narrowing of the blood vessels in the lungs and, ultimately, right ventricular failure. The disease carries a poor prognosis associated with significant morbidity and mortality, having a historical survival rate less than five years. PAH is a subgroup of pulmonary hypertension (PH), which is elevation of blood pressure in lungs. Endothelial dysfunction is thought to occur early on, leading to cell proliferation and structural changes in the pulmonary vasculature that lead to increased pulmonary arterial pressure (PAP) and resultant right ventricular enlargement and dysfunction. In addition, endothelial dysfunction results in chronically impaired production of vasoactive mediators, such as nitric oxide (NO) and prostacyclin, along with prolonged overexpression of vasoconstrictors, such as endothelin-1.

PAH affects approximately 15 out of every one million individuals. There are approximately 1,000 new cases of PAH diagnosed in the United States each year. The mean age at diagnosis is between 50 and 65 years of age, although the disorder may present much earlier in childhood or even infancy. While gender-based prevalence estimates for PAH are variable, estimates for the overall prevalence of pulmonary hypertension (PH) in females is approximately twice that of males.

PAH is part of a larger classification for pulmonary hypertension which is divided into five groups based on World Health Organization (WHO) criteria (designated as WHO Groups 1 through 5). PAH is used to describe exclusively WHO Group 1. Pulmonary hypertension is used to describe the remaining four groups (WHO Groups 2-5) and also when referring to all 5 groups collectively.

- WHO Group 1—PAH: Pulmonary arterial hypertension.
- WHO Group 2—PH: Pulmonary hypertension secondary to left heart disease.
- WHO Group 3—PH: Pulmonary hypertension secondary to lung diseases or hypoxemia.
- WHO Group 4—PH: Chronic thromboembolic pulmonary hypertension.
- WHO Group 5—PH: Pulmonary hypertension with unknown mechanisms.

PAH initially presents as exertional dyspnea, lethargy, and fatigue and is often confused for other disease states. As PAH progresses and right ventricular failure develops, exertional chest pain (i.e., angina), exertional syncope, and peripheral edema may develop. Following confirmation of diagnosis based on hemodynamic parameters, treatment is recommended to lower pulmonary pressures and treat the symptoms of PAH. Although no cure exists for PAH, treatment of PAH is directed at improving hemodynamic measures, New York Heart Association (NYHA) functional class, the 6 minute walk distance (6 MWD), quality of life, and, in some studies, survival.

The severity of PAH may be classified according to the NYHA heart failure guidelines as follows:

- NYHA Class I: Patients with no limitation of activities; they suffer no symptoms from ordinary activities.
- NYHA Class II: Patients with slight, mild limitation of activity; they are comfortable with rest or with mild exertion.
- NYHA Class III: Patients with marked limitation of activity; they are only comfortable at rest.
- NYHA Class IV: Patients who should be at complete rest, confined to bed or chair; any physical activity brings on discomfort and symptoms occur at rest.

While the exact underlying cause of PAH is unclear, mutations in the bone morphogenic protein receptor type II (BMPR2) gene account for approximately 75% of familial PAH and up to 25% of apparently sporadic PAH cases. These mutations may promote cell division or prevent cell death, resulting in an overgrowth of cells in smaller pulmonary arteries. This overgrowth increases resistance to blood flow, triggering hypertension. Additional genetic abnormalities may also contribute to PAH.

Currently Available Treatments

There are five classes of drugs that have been approved to treat PAH, including endothelin receptor antagonists (ERAs), phosphodiesterase type 5 (PDE5) inhibitors, soluble guanylate cyclase stimulators, prostacyclin receptor agonists, and prostacyclin analogs. Approved PAH therapies and their route of administration include:

- ERA: bosentan (oral) and ambrisentan (oral)
- PDE5: sildenafil (oral, intravenous (IV) and tadalafil (oral)
- Soluble Guanylate Cyclase (sGC) Stimulator: riociguat (oral)
- Prostacyclin Receptor Agonist: selexipag (oral)
- Prostacyclin Analog: epoprostenol (IV) iloprost (inhaled), and treprostinil (oral), (subcutaneous and IV), and (inhaled)

Treprostinil is a chemically stable tricyclic benzidine prostanoid with vasodilator properties that is capable of reducing pulmonary vasoconstriction with minimal effects on systemic blood pressure. Treprostinil has been approved for the treatment of PAH under the trade names REMODULIN® (United Therapeutics Corporation; subcutaneous or IV infusion) and TYVASO® (United Therapeutics Corporation; inhaled via ultrasonic, pulsed nebulization delivery device). While both have proven effective for PAH, one advantage of TYVASO's inhaled route of administration is that it brings the drug very near the desired site of action (pulmonary arteries in the lungs).

Despite the current treatment options for PAH patients, each option includes drawbacks, most notably for the inhaled route of administration Tyvaso requires use of a large, cumbersome nebulization device that requires power, water and user manipulation for cleaning and operating. Moreover, the nebulization device by its nature is not convenient to the patient as compared to carrying a small, concealable dry powder inhalation device such as those used for treating asthma and many other chronic and acute issues. Furthermore, nebulized treprostinil has shown clinical limitations on treprostinil dosing, which may limit the applicability of the inhaled route of administration to a smaller subsector of PAH patients than necessarily treatable via the inhaled route from a dry powder inhaled treprostinil product of the present invention.

SUMMARY OF THE INVENTION

The present inventors have developed and reduced to practice an inhalation dry powder formulation of treprostinil that is produced using Liquidia's PRINT® Technology (Particle Replication in Nonwetting Templates), LIQUIDIA TECHNOLOGIES, INC. This PRINT particle formulation for dry powder delivery of treprostinil (otherwise referred to as LIQ861) is under clinical evaluation. The present applicants intend to use the same indication (i.e., treatment of pulmonary arterial hypertension [WHO Group 1] in patients with NYHA Class III symptoms, to improve exercise ability) dose and dose regimen (4x/day) as defined in the approved nebulized treatment label (TYVASO® UNITED THERAPEUTICS). In particular, the present invention provides for dosing levels that exceed the maximum tolerated dose delivered through a nebulizer. In some cases the present invention may also treat other indications under the pulmonary hypertension disease states.

In some embodiments, a dry powder inhalation treatment for pulmonary arterial hypertension according to the present invention includes a dose of dry particles comprising greater than 25 micrograms of treprostinil enclosed in a capsule. In some embodiments, the dose of dry particles comprises from about 25 micrograms to about 400 micrograms of treprostinil. In some embodiments, the dose of dry particles comprises from about 50 micrograms to about 350 micrograms of treprostinil. In some embodiments, the dose of dry particles comprises from about 75 micrograms to about 300 micrograms of treprostinil. In some embodiments, the dose of dry particles comprises from about 100 micrograms to about 300 micrograms of treprostinil. In some embodiments, the dose of dry particles includes greater than or equal to 100 micrograms of treprostinil. In some embodiments, the dose of dry particles comprises greater than or equal to 150 micrograms of treprostinil. In some embodiments, the dose of dry particles comprises greater than or equal to 200 micrograms of treprostinil. In some embodiments, the dose of dry particles comprises greater than or equal to 250 micrograms of treprostinil. In some embodiments, the dose of dry particles comprises greater than or equal to 300 micrograms of treprostinil. In some embodiments, the dose of dry particles includes greater than or equal to 5 mg of the dry particles. In some embodiments, the dose of dry particles includes greater than or equal to 10 mg of the dry particles. In yet other embodiments, the dose of dry particles includes greater than or equal to 15 mg of the dry particles. In further embodiments, a dry powder treatment for pulmonary arterial hypertension, includes a single capsule enclosing 5 mg or more dry particles comprising 25 micrograms of treprostinil per each 5 mg of the dry particles.

In some embodiments, a method of treating a patient having pulmonary arterial hypertension includes providing a patient a dry powder inhaler, providing the patient at least one capsule for use in the dry powder inhaler, wherein the capsule comprises at least 25 micrograms of treprostinil, and instructing the patient to utilize the dry powder inhaler to inhale the treprostinil. In some such embodiments, the capsule includes at least 50 micrograms of treprostinil. In some embodiments, the capsule includes at least 100 micrograms of treprostinil. In some embodiments, the capsule comprises at least 150 micrograms of treprostinil. In some embodiments, the capsule comprises greater than or equal to 200 micrograms of treprostinil. In some embodiments, the capsule comprises greater than or equal to 250 micrograms of treprostinil. In some embodiments, the capsule comprises greater than or equal to 300 micrograms of treprostinil. In some embodiments, the capsule comprises from about 25 micrograms to about 400 micrograms of treprostinil. In some embodiments, the capsule comprises from about 50 micrograms to about 350 micrograms of treprostinil. In some embodiments, the capsule comprises from about 75 micrograms to about 300 micrograms of treprostinil. In some embodiments, the capsule comprises from about 100 micrograms to about 300 micrograms of treprostinil. In further embodiments, the patient may be prescribed to use two capsules per dose cycle per day, generally with PAH requiring 4 times per day dosing. In some embodiments, the patient may be prescribed to use three capsules per day. In some embodiments, the patient may be prescribed to use four capsules per day. In some embodiments, a method of treating a patient having pulmonary arterial hypertension includes dosing the patient having pulmonary arterial hypertension with a dry powder dose of treprostinil, wherein the dose of treprostinil is greater than 85 micrograms (e.g., about 100 micrograms to about 350 micrograms). In some embodiments, the patient may be dosed one, two, three, four, or more times per day. A further method of treating a patient having pulmonary arterial hypertension includes delivering, in dry powder, greater than 12.5 micrograms of treprostinil to a patient per breath. In another embodiment, a method of treating a patient having pulmonary arterial hypertension includes delivering, in dry powder, greater than 25 micrograms of treprostinil to a patient per breath. In another embodiment, a method of treating a patient having pulmonary arterial hypertension includes delivering, in dry powder, from about 12.5 to about 50 micrograms of treprostinil to a patient per breath. In yet another embodiment, a method of treating a patient having pulmonary arterial hypertension includes delivering, in dry powder, about 25 to about 50 micrograms of treprostinil to a patient per breath. In a further embodiment, a method of treating a patient having pulmonary arterial hypertension includes delivering, in dry powder, greater than 50 micrograms of treprostinil to a patient per breath. In a further embodiment, a method of treating a patient having pulmonary arterial hypertension includes delivering, in dry powder, greater than or equal to 100 micrograms of treprostinil to a patient per breath. In a further embodiment, a method of treating a patient having pulmonary arterial hypertension includes delivering, in dry powder, greater than or equal to 150 micrograms of treprostinil to a patient per breath. In a further embodiment, a method of treating a patient having pulmonary arterial hypertension includes delivering, in dry powder, greater than or equal to 200 micrograms of treprostinil to a patient per breath.

A dry powder inhalation composition for treating pulmonary arterial hypertension according to a further embodiment includes a plurality of dry powder particles comprising treprostinil, a non-reducing sugar, a wetting agent, a hydrophobicity modifying agent, a pH modifying agent and a buffer. In some such embodiments, the bulking agent comprises trehalose dihydrate. In some embodiments, the wetting agent comprises polysorbate 80. In some embodiments, the hydrophobicity modifying agent comprises L-leucine. In some embodiments, the pH modifying agent comprises sodium citrate dihydrate. In some embodiments, the buffer comprises sodium chloride. In certain embodiments, the composition comprises less than about 4 percent by weight water. In some embodiments, the composition comprises less than about 2 percent by weight water. In some embodiments, the composition comprises less than about 1 percent by weight water.

In yet further embodiments, the dry powder particles include particles having a three dimensional shape including a width and length not less than 1 micrometer and not more than 2 micrometers and a depth not less than 0.3 micrometers and not more than 0.8 micrometers. In some embodiments, the dry powder particles comprise a dried solution comprising trehalose dihydrate, L-leucine, treprostinil sodium, polysorbate 80, sodium citrate dihydrate, sodium chloride and water. In some embodiments, the dry powder particles comprise by percent solids about 0.581 percent treprostinil sodium, about 92.32 percent trehalose, about 2.19 percent polysorbate 80, about 4.39 percent L-leucine, about 0.26 percent sodium citrate, and about 0.25 percent sodium chloride.

A method of making a particle for dry powder delivery to the lung of a patient in need thereof, in some embodiments, includes molding a composition comprising about 12.30 weight percent trehalose dihydrate, about 0.53 weight percent L-leucine, about 0.07 weight percent treprostinil sodium, about 0.26 weight percent polysorbate 80, about 0.04 weight percent sodium citrate dihydrate, about 0.03 weight percent sodium chloride and about 86.78 weight percent water into a particle. In some embodiments, the method of making the particle further includes drying the composition such that the particle comprises less than 4 percent by weight water.

BRIEF DESCRIPTION OF THE FIGURES

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the illustrated embodiments set forth herein.

FIGS. 3A and 3B are tables including data for Cohort 1 of a clinical trial. The table shown in FIG. 3A contains a summary of the treprostinil concentration-time data for individual subjects with descriptive statistics for the six active subjects in Cohort 1. Preliminary non-compartmental PK parameters for treprostinil are summarized in the table shown in FIG. 3B.

FIGS. 4A and 4B are tables including data for Cohort 2 of a clinical trial. The table shown in FIG. 4A contains a summary of the treprostinil concentration-time data for individual subjects with descriptive statistics for the six active subjects in Cohort 2. Preliminary non-compartmental PK parameters for treprostinil for Cohort 2 are summarized in the table shown in FIG. 4B.

FIGS. 5A and 5B are tables including data for Cohort 3 of a clinical trial. The table shown in FIG. 5A contains a summary of the treprostinil concentration-time data for individual subjects with descriptive statistics for the six active subjects in Cohort 3. Preliminary non-compartmental PK parameters for treprostinil for Cohort 3 are summarized in the table shown in FIG. 5B.

FIGS. 6A and 6B are tables including data for Cohort 4 of a clinical trial. The table shown in FIG. 6A contains a summary of the treprostinil concentration-time data for individual subjects with descriptive statistics for the six active subjects in Cohort 4. Preliminary non-compartmental PK parameters for treprostinil for Cohort 4 are summarized in FIG. 6B.

FIGS. 7A and 7B are tables including data for Cohort 5 for a clinical trial. The table shown in FIG. 7A contains a summary of the treprostinil concentration-time data for individual subjects with descriptive statistics for the six active subjects in Cohort 5. Preliminary non-compartmental PK parameters for treprostinil for Cohort 5 are summarized in FIG. 7B.

FIGS. 8A, 8B, and 8C are tables including data for Cohort 6 for a clinical trial. The table shown in FIG. 8A contains a summary of the treprostinil concentration-time data for individual subjects with descriptive statistics for the six active subjects in Cohort 6-R. Preliminary non-compartmental PK parameters for treprostinil for Cohort 6-R are summarized in FIG. 8B. Preliminary non-compartmental PK parameters for treprostinil for Cohort 6-Original are summarized in FIG. 8C.

DETAILED DESCRIPTION OF EMBODIMENTS

Drug Substance

The drug substance (DS) according to embodiments of the present invention is treprostinil, which is a synthetic analog of prostacyclin ($PGI_2$). The IUPAC name for treprostinil is (2-[[(1R,2R,3aS,9aS)-2-hydroxy-1-[(3S)-3-hydroxyoctyl]-2,3,3a,4,9,9a-hexahydro-1H-cyclopenta[g]naphthalen-5-yl]oxy]acetic acid).

Inhalation Powder Drug Product

Figure 1:
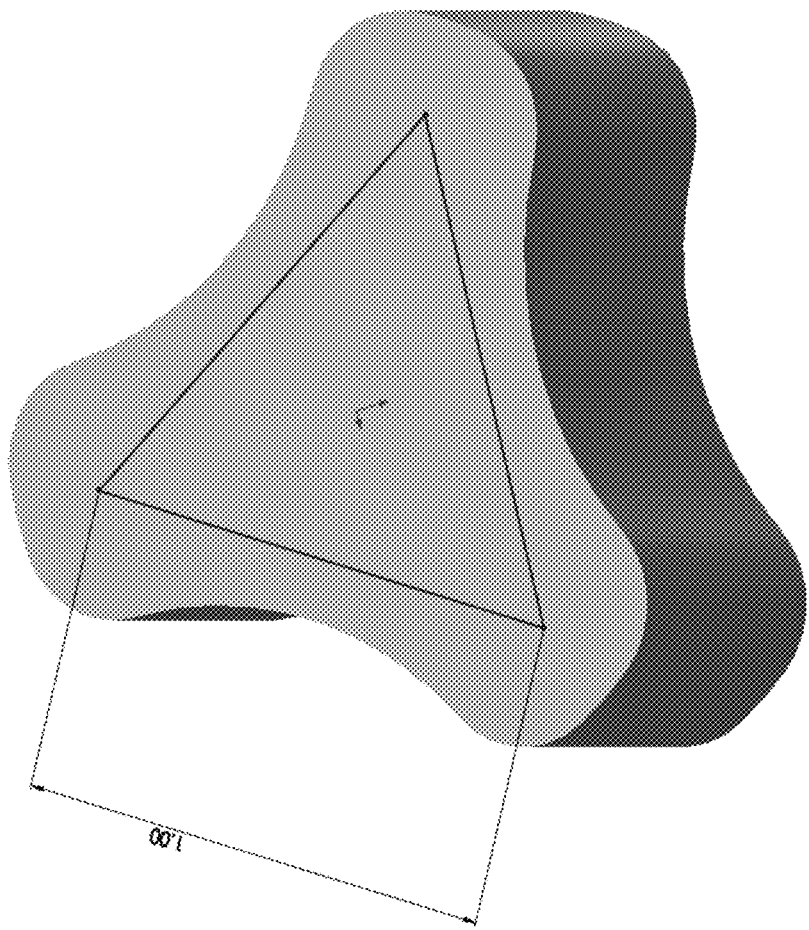
FIG. 1 shows a three-dimension rendering of a pollen particle according to an embodiment of the present invention.

The inhalation powder drug product according to certain aspects of the present invention provides a dry powder dosage form of treprostinil and excipients formed into a particle (drug product intermediate, or DP-intermediate) that is, in some embodiments, filled into a capsule, for example, a hydroxypropyl methylcellulose (HPMC) capsule (size 3) (LIQ861). In some embodiments, the DP-intermediate is a treprostinil/excipient matrix from which particles of precise size and shape are formed according to the methods herein. In one example, the particles of the DP-intermediate comprise a shape corresponding generally to a rounded triangular shape having a volume, where the inner portion of the rounded triangular shape, in size, fits a 1 micrometer equilateral triangle (otherwise referred to as being pollen-shaped). A three-dimensional rendering of such a particle shape is depicted in FIG. 1. In another embodiment, the pollen-shape may be trefoil-shaped with an inscribed circle diameter of 1 micrometer, and a prescribed thickness of a value or range between 0.5 and 1 micrometer, or more preferred 0.7 micrometer. In addition, certain embodiments of the present drug product includes particles having 0.5% treprostinil used in a first clinical study to investigate dose levels of 25 mcg, 50 mcg, 75 mcg, 100 mcg, 125 mcg and 150 mcg treprostinil in LIQ861. In further embodiments, a drug product according to the present invention may provide dose levels of 175 mcg, 200 mcg, 225 mcg, 250 mcg, 275 mcg, 300 mcg, 325 mcg, or 350 mcg treprostinil. In further embodiments, a drug product according to the present invention may provide dose levels of 50 mcg treprostinil plus or minus 10 mcg, 9 mcg, 8 mcg, 7 mcg, 6 mcg, 5 mcg, 4 mcg, 3 mcg, 2 mcg or 1 mcg treprostinil loaded into capsules for delivery to a patient in a dry powder. In further embodiments, a drug product according to the present invention may provide dose levels of 75 mcg treprostinil plus or minus 10 mcg, 9 mcg, 8 mcg, 7 mcg, 6 mcg, 5 mcg, 4 mcg, 3 mcg, 2 mcg or 1 mcg treprostinil loaded into capsules for delivery to a patient in a dry powder. In further embodiments, a drug product according to the present invention may provide dose levels of 100 mcg treprostinil plus or minus 10 mcg, 9 mcg, 8 mcg, 7 mcg, 6 mcg, 5 mcg, 4 mcg, 3 mcg, 2 mcg or 1 mcg treprostinil loaded into capsules for delivery to a patient in a dry powder. In further embodiments, a drug product according to the present invention may provide dose levels of 150 mcg treprostinil plus or minus 10%, 9%, 8%, 7%, 6%, 5%, 4%, 3%, 2% or 1% treprostinil loaded into capsules for delivery to a patient in a dry powder. In further embodiments, a drug product according to the present invention may provide dose levels of 200 mcg treprostinil plus or minus 10%, 9%, 8%, 7%, 6%, 5%, 4%, 3%, 2% or 1% mcg treprostinil loaded into capsules for delivery to a patient in a dry powder. In further embodiments, a drug product according to the present invention may provide dose levels of 300 mcg treprostinil plus or minus 10%, 9%, 8%, 7%, 6%, 5%, 4%, 3%, 2% or 1% treprostinil loaded into capsules for delivery to a patient in a dry powder.

According to the present invention, due to the formulation of the present dry powder particles, the particles remain stable for long periods of time at relatively low humidity conditions. In some embodiments, the present invention provides dry powder particles packaged under sealed conditions that remain stable for more than 3 months at 40 degrees Celsius at 75 percent relative humidity. Therefore, the particles can be utilized to provide a patient with a dry powder inhaled drug form of treprostinil, not previously available until the present invention. This invention, in some embodiments, provides a user with a reduction in interaction with drug product by removing the requirements on the patient to reconstitute their drug product for use in a nebulizer device. The patient is also enabled to receive equal dosing with more than 50 percent reduction in breath treatments on a device, and in some embodiments more than 65 percent reduction in breath treatments.

The present invention, in some embodiments, also provides a dry formulation of treprostinil, which upon delivery to a patient via the inhaled route, becomes soluble and pharmaceutically available in less than 10 seconds. In some embodiments, the dry formulation composition becomes soluble and pharmaceutically available in less than 5 seconds. In some embodiments, the dry formulation composition becomes soluble and pharmaceutically available in less than 2 seconds. In some embodiments, the dry formulation composition becomes soluble and pharmaceutically available in about 1 second. In some embodiments, the dry formulation composition becomes soluble and pharmaceutically available in less than 1 second. In some embodiments, the dry formulation composition becomes soluble and pharmaceutically available in less than about 0.5 seconds. Furthermore, the excipients in the dry particle formulation of the present invention maintain pH and salt gradient during processing such that the active agent remains in a state to become soluble in the lung conditions of a user.

A detailed description of the LIQ861 formulation, particle composition, particle geometry, packaging, device, delivery, stability, dose, and a description of the use follows.

In some embodiments, a formulation according to the present invention includes a drug substance (e.g., Treprostinil, Treprostinil Sodium) together with one or more excipients. In some embodiments, the one or more excipients may include a bulking agent, a wetting agent, a hydrophobicity modifier, a pH modifier, a buffer component, or combinations thereof. Examples of such formulations according to certain specific embodiments are provided in the tables below.

LIQ861 Drug Product-Intermediate Description for Active (LIQ861) and Placebo Formulations (Dihydrate Form Calculations)

| Component | Function | Quantity (mg/g) (Active) | Percent Solids |
|---|---|---|---|
| Treprostinil Sodium | Drug Substance | 5.3 (5.0 as treprostinil) | 0.53 |
| Trehalose Dihydrate | Bulking Agent | 930 | 92.97 |
| Polysorbate 80 | Wetting Agent | 20 | 2.00 |
| L-Leucine | Hydrophobicity Modifier | 40 | 4.00 |
| Sodium Citrate Dihydrate | pH Modifier | 2.7 | 0.27 |
| Sodium Chloride | Buffer Component | 2.3 | 0.23 |

LIQ861 Drug Product-Intermediate Description for Active (LIQ861) and Placebo Formulations (Anhydrous Form Calculations)

| Component | Function | Quantity (mg/g) (Active) | Percent Solids | Normalized mg/g |
|---|---|---|---|---|
| Treprostinil Sodium | Drug Substance | 5.3 (5.0 as treprostinil) | 0.581 | 5.81 |
| Trehalose | Bulking Agent | 841 | 92.32 | 923.23 |
| Polysorbate 80 | Wetting Agent | 20 | 2.19 | 21.94 |
| L-Leucine | Hydrophobicity Modifier | 40 | 4.39 | 43.89 |
| Sodium Citrate | pH Modifier | 2.4 | 0.26 | 2.60 |
| Sodium Chloride | Buffer Component | 2.3 | 0.25 | 2.52 |

Inhalation Device

According to an embodiment of administering the present invention drug particle, LIQ861 is administered using an RS00 Model 8 dry powder inhalation device (Plastiape S.p.A.). The present invention provides for multi-day administration of LIQ861 according to some embodiments.

Indication

The present invention, according to an embodiment, is useful for the treatment of pulmonary arterial hypertension (WHO Group 1) in patients with NYHA Class III symptoms, to improve exercise ability.

Chemistry, Manufacturing, and Controls (CMC)

Drug Substance (DS)

The drug substance according to embodiments of the present invention is treprostinil and the salt form used for LIQ861 is treprostinil sodium. Detailed information about treprostinil sodium, including physical and chemical properties, characterization, manufacturing and controls, container closure system, and stability attributes may be found in the Drug Master File (DMF) lodged with the FDA for treprostinil. General information on the DS is provided herein.

Nomenclature

The international non-proprietary name (INN) for LIQ861 is treprostinil sodium. The chemical name is 2-((1R, 2R,2R,3aS,9aS)-2-hydroxy-1-((S)-3-hydroxyoctyl)-2,3,3a, 4,9,9a-hexahydro-1H-cyclopenta[b]naphthalen-5-yloxy) acetic acid, sodium salt. The chemical abstracts service registration number is [289480-64-4].

Structure

The structure of treprostinil sodium is depicted herein below. The molecular formula is $C_{23}H_{33}NaO_5$ and it has a molecular weight of 412.49 daltons.

Chemical Structure of Treprostinil Sodium

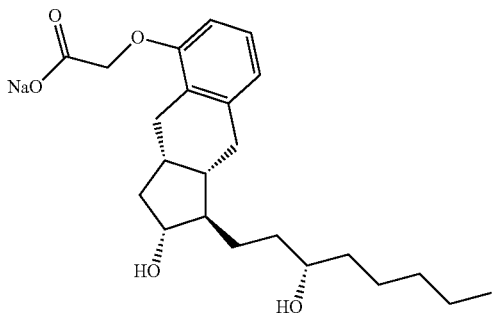

General Properties

Treprostinil sodium appears as a white or pale yellowish powder. It is very soluble in water and ethanol, very slightly soluble in acetone, and practically insoluble in acetonitrile, n-hexane, and ethyl acetate. The specific optical rotation calculated with reference to the anhydrous and solvent free basis is $[\alpha]_D^{20}=+38.0°\sim+44.0°$. It is hygroscopic. The pKa of treprostinil is 4.5, using aqueous titration with 20% ethanol as a co-solvent. The distribution coefficient of treprostinil in various buffer solutions at various pH levels indicates distribution into octanol layers at all pH levels.

Inhalation Particle Drug Product—LIQ861

Description and Composition of the Drug Product Particle

The inhalation drug particle product, in some embodiments, includes or consists of a dry powder dosage form of treprostinil and excipients (drug product-intermediate; DP-intermediate; or drug particle) that may be filled into, for example, a HPMC capsule (size 3). The DP-intermediate, in some embodiments, is a treprostinil/excipient matrix from which particles of precise size (e.g., 1 μm) and shape (e.g., "pollen-shaped") are created using Liquidia's PRINT Technology. The "pollen-shaped" particles may also be described as trefoil-shaped, with an inscribed circle diameter of 1 μm, and a thickness of 0.7 μm. A three-dimensional rendering of such a particle shape is depicted in FIG. 1. LIQ861 comprised drug product capsule strengths of 25 mcg, 50 mcg, and 75 mcg treprostinil used in the first clinical study to investigate planned dose levels of 25 mcg, 50 mcg, 75 mcg, 100 mcg, 125 mcg and 150 mcg treprostinil. The 100 mcg, 125 mcg and 150 mcg doses may be made up of a combination of lower dose capsules. In further embodiments, a drug product according to the present invention may provide capsules with dose levels of 175 mcg, 200 mcg, 225 mcg, 250 mcg, 275 mcg, 300 mcg, 325 mcg, or 350 mcg treprostinil. In further embodiments, a drug product according to the present invention may provide capsules with dose levels of 50 mcg treprostinil plus or minus 10 mcg, 9 mcg, 8 mcg, 7 mcg, 6 mcg, 5 mcg, 4 mcg, 3 mcg, 2 mcg or 1 mcg treprostinil for delivery to a patient in a dry powder. In further embodiments, a drug product according to the present invention may provide capsules with dose levels of 75 mcg treprostinil plus or minus 10 mcg, 9 mcg, 8 mcg, 7 mcg, 6 mcg, 5 mcg, 4 mcg, 3 mcg, 2 mcg or 1 mcg treprostinil for delivery to a patient in a dry powder. In further embodiments, a drug product according to the present invention may provide capsules with dose levels of 100 mcg treprostinil plus or minus 10 mcg, 9 mcg, 8 mcg, 7 mcg, 6 mcg, 5 mcg, 4 mcg, 3 mcg, 2 mcg or 1 mcg treprostinil for delivery to a patient in a dry powder. In further embodiments, a drug product according to the present invention may provide capsules with dose levels of 150 mcg treprostinil plus or minus 10%, 9%, 8%, 7%, 6%, 5%, 4%, 3%, 2% or 1% treprostinil for delivery to a patient in a dry powder. In further embodiments, a drug product according to the present invention may provide capsules with dose levels of 200 mcg treprostinil plus or minus 10%, 9%, 8%, 7%, 6%, 5%, 4%, 3%, 2% or 1% mcg treprostinil for delivery to a patient in a dry powder. In further embodiments, a drug product according to the present invention may provide capsules with dose levels of 300 mcg treprostinil plus or minus 10%, 9%, 8%, 7%, 6%, 5%, 4%, 3%, 2% or 1% treprostinil for delivery to a patient in a dry powder. A summary of the LIQ861 formulation, including powder composition, particle geometry, and a description of the dosing unit according to certain exemplary embodiments follows.

LIQ861 Drug Product-Intermediate Description for Active (LIQ861) and Placebo Formulations (Dihydrate)

| Component | Function | Quantity (mg/g) (Active) | Percent Solids |
|---|---|---|---|
| Treprostinil Sodium | Drug Substance | 5.3 (5.0 as treprostinil) | 0.53 |
| Trehalose Dihydrate | Bulking Agent | 930 | 92.97 |
| Polysorbate 80 | Wetting Agent/Process Aide | 20 | 20 |
| L-Leucine | Hydrophobicity Modifier | 40 | 40 |
| Sodium Citrate Dihydrate | pH Modifier | 2.7 | 0.27 |
| Sodium Chloride | Buffer Component | 2.3 | 0.23 |

Inhalation Drug Product Dosing Unit Description

| Capsule | Size 3 Opaque White HPMC Capsule | | | |
|---|---|---|---|---|
| Fill Description | White to Off-White Powder | | | |
| Fill Particle Shape | "pollen-shaped" | | | |
| Active Strength (μg) | 0 (placebo)* | 25 | 50 | 75 |
| Formulation Powder per Capsule (mg) | 15 | 5 | 10 | 15 |

*Excipients only (no treprostinil).
Abbreviations: HPMC, hydroxypropyl methylcellulose According to some embodiments of the present invention, drug particles are provided that include a composition having a target dose of 15-90 μg of delivered treprostinil to the patient (current TYVASO® label is 18-54 μg). In some embodiments of the present invention the dose of treprostinil provided to the patient can be, for example, 100 micrograms, 125 micrograms or 150 micrograms. In some embodiments of the present invention the dose of treprostinil provided to the patient, for example, can contain about 100 micrograms, about 125 micrograms or about 150 micrograms. In some embodiments, each dose contains greater than or equal to 200 micrograms of treprostinil. In some embodiments, each dose contains greater than or equal to 225 micrograms of treprostinil. In some embodiments, each dose contains greater than or equal to 250 micrograms of treprostinil. In some embodiments, each dose contains greater than or equal to 275 micrograms of treprostinil. In some embodiments, each dose contains greater than or equal to 300 micrograms of treprostinil. In some embodiments, each dose contains from about 10 micrograms to about 15 micrograms, 15 micrograms to about 20 micrograms, 20 micrograms to about 25 micrograms, 25 micrograms to about 30 micrograms, about 30 micrograms to about 35 micrograms, about 35 micrograms to about 40 micrograms, about 40 micrograms to about 45 micrograms, about 45 micrograms to about 50 micrograms, about 50 micrograms to about 55 micrograms, about 55 micrograms to about 60 micrograms, about 60 micrograms to about 65 micrograms, about 65 micrograms to about 70 micrograms, about 70 micrograms to about 75 micrograms, about 75 micrograms to about 80 micrograms, about 80 micrograms to about 85 micrograms, about 85 micrograms to about 90 micrograms, about 90 micrograms to about 95 micrograms, about 95 micrograms to about 100 micrograms, or about 100 micrograms to about 105 micrograms of treprostinil. In some embodiments, each dose contains from about 100 micrograms to about 110 micrograms, 110 micrograms to about 120 micrograms, 120 micrograms to about 130 micrograms, 130 micrograms to about 140 micrograms, about 140 micrograms to about 150 micrograms, about 150 micrograms to about 160 micrograms, about 160 micrograms to about 170 micrograms, about 170 micrograms to about 180 micrograms, about 180 micrograms to about 190 micrograms, about 190 micrograms to about 200 micrograms, about 200 micrograms to about 210 micrograms, about 210 micrograms to about 220 micrograms, about 220 micrograms to about 230 micrograms, about 230 micrograms to about 240 micrograms, about 240 micrograms to about 250 micrograms, about 250 micrograms to about 260 micrograms, about 260 micrograms to about 270 micrograms, about 270 micrograms to about 280 micrograms, about 280 micrograms to about 290 micrograms, about 290 micrograms to about 300 micrograms, about 300 micrograms to about 310 micrograms, about 310 micrograms to about 320 micrograms, about 320 micrograms to about 330 micrograms, about 330 micrograms to about 340 micrograms, or about 340 micrograms to about 350 micrograms of treprostinil. In some embodiments, each dose contains from about 25 micrograms to about 400 micrograms of treprostinil. In some embodiments, each dose contains from about 25 micrograms to about 350 micrograms of treprostinil. In some embodiments, each dose contains from about 25 micrograms to about 300 micrograms of treprostinil. In some embodiments, each dose contains from about 50 micrograms to about 300 micrograms of treprostinil. In some embodiments, each dose contains from about 75 micrograms to about 300 micrograms of treprostinil. In some embodiments, each dose contains from about 100 micrograms to about 300 micrograms of treprostinil. In some embodiments, each dose contains from about 125 micrograms to about 300 micrograms of treprostinil. In some embodiments, each dose contains from about 150 micrograms to about 300 micrograms of treprostinil. In some embodiments, each dose contains from about 175 micrograms to about 300 micrograms of treprostinil. In some embodiments, each dose contains from about 200 micrograms to about 300 micrograms of treprostinil. In some embodiments, each dose contains from about 225 micrograms to about 300 micrograms of treprostinil. In some embodiments, each dose contains from about 250 micrograms to about 300 micrograms of treprostinil. In some embodiments, each dose contains from about 275 micrograms to about 300 micrograms of treprostinil. In some embodiments, each dose contains from about 50 micrograms to about 75 micrograms of treprostinil. In some embodiments, each dose contains from about 50 micrograms to about 100 micrograms of treprostinil. In some embodiments, each dose contains from about 50 micrograms to about 150 micrograms of treprostinil. In some embodiments, each dose contains from about 75 micrograms to about 100 micrograms of treprostinil. In some embodiments, each dose contains from about 75 micrograms to about 125 micrograms of treprostinil. In some embodiments, each dose contains from about 75 micrograms to about 150 micrograms of treprostinil. In some embodiments, each dose contains from about 75 micrograms to about 175 micrograms of treprostinil. In some embodiments, each dose contains from about 75 micrograms to about 200 micrograms of treprostinil. In some embodiments, each dose contains from about 75 micrograms to about 225 micrograms of treprostinil. In some embodiments, each dose contains from about 75 micrograms to about 250 micrograms of treprostinil. In some embodiments, each dose contains from about 75 micrograms to about 275 micrograms of treprostinil. In some embodiments, each dose contains from about 75 micrograms to about 300 micrograms of treprostinil. In some embodiments, each dose contains from about 75 micrograms to about 325 micrograms of treprostinil. In some embodiments, each dose contains from about 75 micrograms to about 350 micrograms of treprostinil. In some embodiments, each dose contains from about 100 micrograms to about 125 micrograms of treprostinil. In some embodiments, each dose contains from about 100 micrograms to about 150 micrograms of treprostinil. In some embodiments, each dose contains from about 100 micrograms to about 175 micrograms of treprostinil. In some embodiments, each dose contains from about 100 micrograms to about 200 micrograms of treprostinil. In some embodiments, each dose contains from about 100 micrograms to about 225 micrograms of treprostinil. In some embodiments, each dose contains from about 100 micrograms to about 250 micrograms of treprostinil. In some embodiments, each dose contains from about 100 micrograms to about 275 micrograms of treprostinil. In some embodiments, each dose contains from about 100 micrograms to about 300 micrograms of treprostinil. In some embodiments, each dose contains from about 100 micrograms to about 325 micrograms of treprostinil. In some embodiments, each dose contains from about 100 micrograms to about 350 micrograms of treprostinil. In some embodiments, each dose contains from about 125 micrograms to about 150 micrograms of treprostinil. In some embodiments, each dose contains from about 125 micrograms to about 175 micrograms of treprostinil. In some embodiments, each dose contains from about 125 micrograms to about 200 micrograms of treprostinil. In some embodiments, each dose contains from about 125 micrograms to about 225 micrograms of treprostinil. In some embodiments, each dose contains from about 125 micrograms to about 250 micrograms of treprostinil. In some embodiments, each dose contains from about 125 micrograms to about 275 micrograms of treprostinil. In some embodiments, each dose contains from about 125 micrograms to about 300 micrograms of treprostinil. In some embodiments, each dose contains from about 125 micrograms to about 325 micrograms of treprostinil. In some embodiments, each dose contains from about 125 micrograms to about 350 micrograms of treprostinil. In some embodiments, each dose contains from about 150 micrograms to about 175 micrograms of treprostinil. In some embodiments, each dose contains from about 150 micrograms to about 200 micrograms of treprostinil. In some embodiments, each dose contains from about 150 micrograms to about 225 micrograms of treprostinil. In some embodiments, each dose contains from about 150 micrograms to about 250 micrograms of treprostinil. In some embodiments, each dose contains from about 150 micrograms to about 275 micrograms of treprostinil. In some embodiments, each dose contains from about 150 micrograms to about 300 micrograms of treprostinil. In some embodiments, each dose contains from about 150 micrograms to about 325 micrograms of treprostinil. In some embodiments, each dose contains from about 150 micrograms to about 350 micrograms of treprostinil. In some embodiments, each dose contains from about 175 micrograms to about 200 micrograms of treprostinil. In some embodiments, each dose contains from about 175 micrograms to about 225 micrograms of treprostinil. In some embodiments, each dose contains from about 175 micrograms to about 250 micrograms of treprostinil. In some embodiments, each dose contains from about 175 micrograms to about 275 micrograms of treprostinil. In some embodiments, each dose contains from about 175 micrograms to about 300 micrograms of treprostinil. In some embodiments, each dose contains from about 175 micrograms to about 325 micrograms of treprostinil. In some embodiments, each dose contains from about 175 micrograms to about 350 micrograms of treprostinil. In some embodiments, each dose contains from about 200 micrograms to about 225 micrograms of treprostinil. In some embodiments, each dose contains from about 200 micrograms to about 250 micrograms of treprostinil. In some embodiments, each dose contains from about 200 micrograms to about 275 micrograms of treprostinil. In some embodiments, each dose contains from about 200 micrograms to about 300 micrograms of treprostinil. In some embodiments, each dose contains from about 200 micrograms to about 325 micrograms of treprostinil. In some embodiments, each dose contains from about 200 micrograms to about 350 micrograms of treprostinil. In some embodiments, each dose contains from about 225 micrograms to about 250 micrograms of treprostinil. In some embodiments, each dose contains from about 225 micrograms to about 275 micrograms of treprostinil. In some embodiments, each dose contains from about 225 micrograms to about 300 micrograms of treprostinil. In some embodiments, each dose contains from about 225 micrograms to about 325 micrograms of treprostinil. In some embodiments, each dose contains from about 225 micrograms to about 350 micrograms of treprostinil. In some embodiments, each dose contains from about 250 micrograms to about 275 micrograms of treprostinil. In some embodiments, each dose contains from about 250 micrograms to about 300 micrograms of treprostinil. In some embodiments, each dose contains from about 250 micrograms to about 325 micrograms of treprostinil. In some embodiments, each dose contains from about 250 micrograms to about 350 micrograms of treprostinil. In some embodiments, each dose contains from about 275 micrograms to about 300 micrograms of treprostinil. In some embodiments, each dose contains from about 275 micrograms to about 325 micrograms of treprostinil. In some embodiments, each dose contains from about 275 micrograms to about 350 micrograms of treprostinil. In some embodiments, each dose contains from about 300 micrograms to about 325 micrograms of treprostinil. In some embodiments, each dose contains from about 300 micrograms to about 350 micrograms of treprostinil. In some embodiments, each dose contains from about 325 micrograms to about 350 micrograms of treprostinil. In some embodiments, each dose contains from about 350 micrograms to about 375 micrograms of treprostinil. In some embodiments, each dose contains from about 375 micrograms to about 400 micrograms of treprostinil. In some embodiments, a patient may be provided with one, two, three, four, or more doses per day. In some embodiments, a patient may be provided up to one, two, three, or four doses per day. Each dose may be contained in a single capsule according to some embodiments, for example, a HPMC capsule (size 3). In other embodiments, a dose may be made up of a combination of lower dose capsules. In some embodiments, a patient may be provided with four doses per day to match the current treatment cycle (nebulized treprostinil) however the drug dose per treatment cycle under the present invention dry powder provides significantly higher dose levels to be safely administered, such as for example, up to 100 mcg of treprostinil per dosing, up to 125 mcg of treprostinil and up to 150 mcg of treprostinil per dosing as each were surprisingly demonstrated in the first clinical trial of LIQ861. In alternative embodiments, a patient may be provided with four doses per day to match the current treatment cycle (nebulized treprostinil) however the drug dose per treatment cycle under the present invention dry powder provides significantly higher dose levels to be achieved, such as for example, up to 200 mcg of treprostinil per dosing and up to 300 mcg of treprostinil per dosing as surprisingly demonstrated in pre-clinical toxicology studies using LIQ861.

Treprostinil itself is poorly soluble in unbuffered water and low pH buffers. However, the solubility improves with increasing pH as the carboxylic acid is deprotonated. The sodium salt was selected for use in this product since it enhances dissolution in aqueous media and facilitates processing.

Excipients

According to some embodiments of the present invention, the DP-intermediate (anhydrous) is comprised of particles that include, for example, the following excipients: trehalose, polysorbate 80, L-leucine, sodium citrate, and sodium chloride. In some embodiments, the ratio of treprostinil sodium and excipients is 0.581:92.32:2.19:4.39:0.26:0.25 (wt:wt solids) treprostinil sodium:trehalose:polysorbate 80:leucine:sodium citrate:sodium chloride. A summary of the function, quantity, and compendial status of these excipients is provided herein.

The excipients were selected based upon the following functional requirements for the formulation:

Trehalose Dihydrate: Trehalose comprises the bulk of the particle and was selected because it is a non-reducing sugar with a high glass transition temperature. Trehalose is an example of a non-reducing sugar (as opposed to lactose, which is a reducing sugar) that can be used in the present invention. Trehalose is more chemically compatible with compounds containing primary amines, such as leucine.

Ultra-Pure Polysorbate 80 (Ultra-Pure Tween 80): Polysorbate 80 is added as a processing aide/wetting agent to facilitate particle manufacturing. In some embodiments, Polysorbate 80 is a particle processing aide and enables film generation during particle manufacture by decreasing dewetting, leading to uniform particle morphology.

L-leucine: Leucine is added as a hydrophobicity and surface modifier to reduce the hygroscopicity of the particle and improve aerosol efficiency. L-leucine is an example of a formulation additive to reduce hygroscopicity to improve stability of the final drug product powder.

Sodium chloride and sodium citrate: Sodium citrate and sodium chloride are used to buffer the stock solution used in the PRINT Technology manufacturing process and to help control acidity in the particle. Sodium chloride and sodium citrate are examples of buffers that help maintain pH and control ionization/acidity of the formulation. In some embodiments of the present invention, pH is maintained between about pH 6.0 and 7.2.

In addition to the active pharmaceutical ingredient the present drug particle comprises a bulking agent, wetting agent, hydrophobicity modifier, pH modifier and buffer. In some embodiments, the present drug particle comprises, along with the active ingredients, a bulking agent, hydrophobicity controlling agent, and a pH controlling agent.

According to another embodiment of the present invention, LIQ861 contains five excipients as follows: treprostinil sodium:trehalose dihydrate:leucine:polysorbate 80:sodium citrate dihydrate:sodium chloride at ratios of 0.53:92.97:4:2:0.27:0.23. At an example treprostinil dose level of 100 μg/day of the present invention drug particles, a patient would receive the following daily excipient doses:

18.6 mg of trehalose dihydrate. Assuming a patient weighs 60 kg and has a lung mass of 1000 g, this is equivalent to 310 μg/kg and 18.6 μg/g of lung.

0.4 mg of polysorbate 80. Assuming a patient weighs 60 kg and has a lung mass of 1000 g, this is equivalent to 6.7 μg/kg and 0.4 μg/g of lung.

0.8 mg of leucine. Assuming a patient weighs 60 kg and has a lung mass of 1000 g, this is equivalent to 13.3 μg/kg and 0.8 μg/g of lung.

0.05 mg of sodium citrate and 0.05 mg of sodium chloride. Assuming a patient weighs 60 kg and has a lung mass of 1000 g, this is equivalent to 0.83 μg/kg for each compound and 0.05 μg/g of lung for each compound.

Formulation Development

According to embodiments of the present invention, LIQ861 has been developed as a novel formulation of treprostinil for the treatment of PAH. Treprostinil is currently approved for use in the treatment of PAH by subcutaneous, IV, oral, and inhalation routes of administration. TYVASO is currently the only marketed inhaled formulation of treprostinil and is formulated as a liquid solution for administration using a nebulizer. The nebulized treprostinil is dosed, at maintenance dose, of 6 mcg drug per breath over 9 breaths for a dose of 54 mcg per dosing session. The nebulized treprostinil also has a maximum tolerated dose of 84 mcg over a dosing session with 14 breaths.

LIQ861 is suitable for inhaled administration using a dry powder inhalation device. The physicochemical properties and performance characteristics, manufacturing process and packaging, and stability characteristics of the DP have been studied, and a suitable formulation has been identified for progression into human studies.

Physiochemical and Biological Properties

Figure 9:
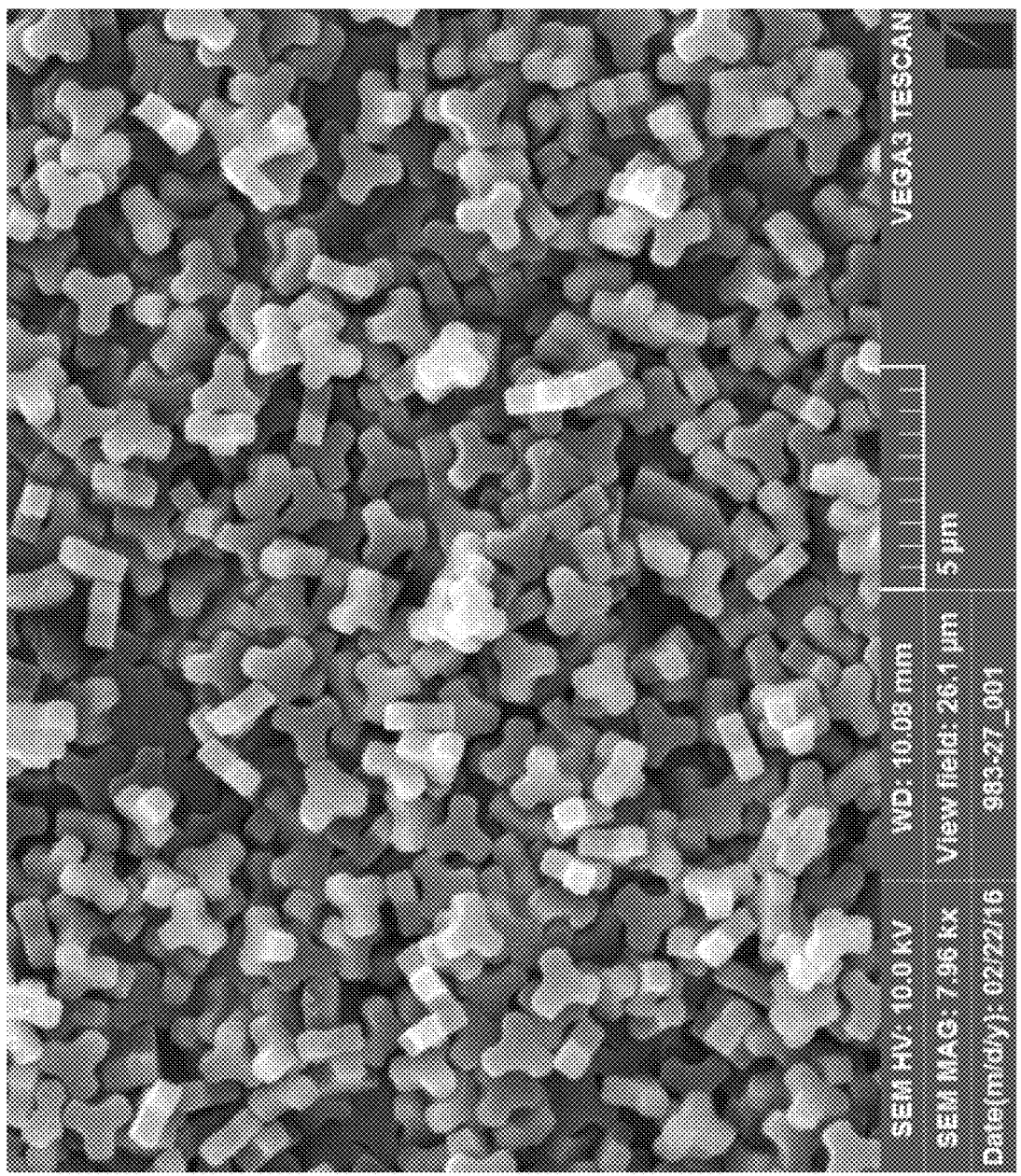
FIG. 9 is an SEM image showing pollen-shaped particles according to an embodiment of the present invention.
Figure 10:
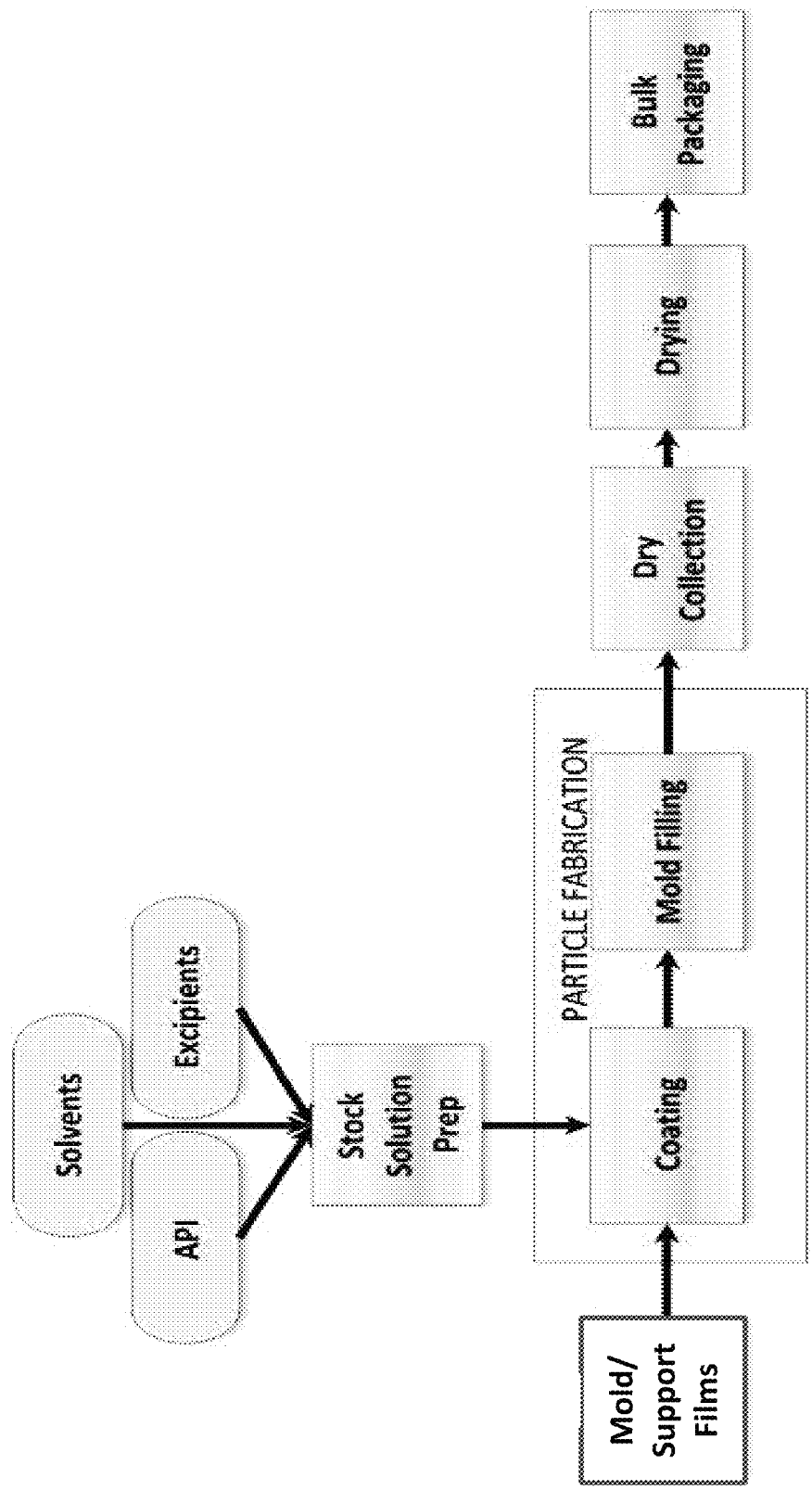
FIG. 10 is a flow diagram showing a process of manufacturing particles according to an embodiment of the present invention.

The "pollen-shaped" LIQ861 particles according to certain embodiments have an aerodynamic size to enable efficient delivery to the pulmonary arterioles (1≤MMAD≤5 μm) with a high FPF to limit oropharyngeal deposition. A scanning electron microscopy (SEM) image of the "pollen-shaped" feature is provided in FIG. 9. The formulation of example particles shown in FIG. 9 is: treprostinil:trehalose:leucine:polysorbate 80:sodium citrate:sodium chloride (Batch LKI-1R-983-27). Example aerosol data for the active particles are also provided in the table below.

During the development of the LIQ861 formulation, the applicants tested other possible particle shapes and sizes (e.g., 1.5 μm donut, 3.0 μm donut). Based upon these studies, the applicants observed that the "pollen-shaped" feature resulted in a greater FPF, reduced MMAD, acceptable ED, and dose uniformity characteristics when compared to other features both with and without treprostinil.

Representative Aerosol Data (NGI) for Active Particles

| Sample | MMAD (μm) | GSD | ED (% nominal) | FPF (% ED) |
|---|---|---|---|---|
| Treprostinil Sodium: Trehalose:Leucine:Polysorbate 80:Sodium Citrate:Sodium Chloride ("pollen-shaped") | 1.88 | 1.99 | 64 | 83 |

Abbreviations: NGI, Next Generation Impactor ™, MSP Corp.; MMAD, mass median aerodynamic diameter; GSD, geometric standard deviation; ED, emitted dose; FPF, fine particle fraction; wt, weight. Batch LKI-1R-0983-21.

Manufacture

The manufacturing of LIQ861 particles according to some embodiments of the present invention is described below. A process flow diagram for the particles (also referred to as DP-intermediate) according to some embodiments is shown in FIG. 10.

In particular embodiments, the particles of the present disclosure are fabricated using PRINT® Technology (Liquidia Technologies, Inc., Morrisville, N.C.) particle fabrication. In particular, the particles are made by molding the materials intended to make up the particles in mold cavities.

In some embodiments, the molds can be polymer-based molds and the mold cavities can be formed into any desired shape and dimension. Uniquely, as the particles are formed in the cavities of the mold, the particles are highly uniform with respect to shape, size, and composition. Due to the consistency among the physical and compositional makeup of the particles of the present compositions, the compositions of the present disclosure provide highly uniform release rates and dosing ranges. Methods and materials that may be used for fabricating the particles according to embodiments of the present disclosure are further described and disclosed in issued patents and patent applications, each of which are incorporated herein by reference in its entirety: U.S. Pat. Nos. 8,518,316; 8,444,907; 8,420,124; 8,268,446; 8,263,129; 8,158,728; 8,128,393; 7,976,759; U.S. patent application publications Nos. 2013-0249138, 2013-0241107, 2013-0228950, 2013-0202729, 2013-0011618, 2013-0256354, 2012-0189728, 2010-0003291, 2009-0165320, 2008-0131692; and pending U.S. application Ser. No. 13/852,683 filed Mar. 28, 2013 and Ser. No. 13/950,447 filed Jul. 25, 2013.

Particle Fabrication

An aqueous stock solution is prepared at the desired total solids concentration. All other excipients are combined with treprostinil and then filtered prior to particle fabrication.

The stock solution is applied in a thin layer to a continuous polyethylene terephthalate (PET) substrate backing layer. Forced air heat is used to drive off the water resulting in a dry film of treprostinil and excipients. The dried film is then brought into contact with a mold film, having cavities of the desired shape and size which the drug product particles will mimic, at an elevated temperature. The drug/excipient blend flows into the cavities of the mold, conforming to the shape defined by the cavity. The result is a uniform array of particles adhered to a PET backing layer. The particles are then allowed to cool to room temperature as the roll is wound up for later collection.

In one example of the present drug particles, the following stock solution is used:

Stock Solution Components Used for Manufacture of Treprostinil Particles, According to an Embodiment:

| Stock component | Target Solution Concentration (Active) | Target Solution Concentration (Placebo) | Target |
|---|---|---|---|
| Trehalose | 12% | 12.7% | Adjusted based on mass balance of other formulation components |
| Leucine | 0.52% | 0.54% | 0.52-0.54% (4% solids) |
| Treprostinil Sodium | 0.069% | 0% | 0.069% (0.53% solids) |
| Polysorbate 80 | 0.26% | 0.27% | 0.26-0.28% (2% solids) |
| Sodium Citrate | 0.035% | 0.037% | Maintain pH stock solution for stability of treprostinil |
| NaCl | 0.030% | 0.031% | Maintain tonicity of stock solution |
| Diluent (water) | 87.0% | 86.4% | 86-91% evaluated; to coat appropriate formulation mass for processing and solubility of excipient component(s) |

Dry Collection and Drying

Next, the particles are dry collected, the process of removing the molded particles from the PET backing layer and thereby creating a bulk powder. The mold is first separated from the PET backing layer, exposing the particle array attached to the PET backing layer. The particle array is then passed across a blade, in some embodiments a plastic blade, to dislodge the particles from the backing layer. The particles can then be collected into a bulk powder for further processing.

Humidity is controlled to less than 15% RH during collection, in some embodiments due to the hygroscopicity of the powder. Temperature is maintained at ambient, typically between 15 and 25° C.

Drying and Bulk Packaging

The drug particles are dried at less than or equal to 150 mTorr of nitrogen or dry air for at least 2 days in a benchtop lyophilizer at room temperature, according to some embodiments.

In some embodiments, the particles of the present invention are dried to less than about 10 percent water content. In some embodiments, the particles of the present invention are dried to less than about 5 percent water content. In further embodiments, the particles of the present invention are dried to less than about 4 percent water content. In still further embodiments, the particles of the present invention are dried to less than about 2 percent water content. In a preferred embodiment, the product is dried to less than about 1 percent water content by Karl Fisher titration.

Batch-to-Batch Uniformity of Drug Particles

Figure 2:
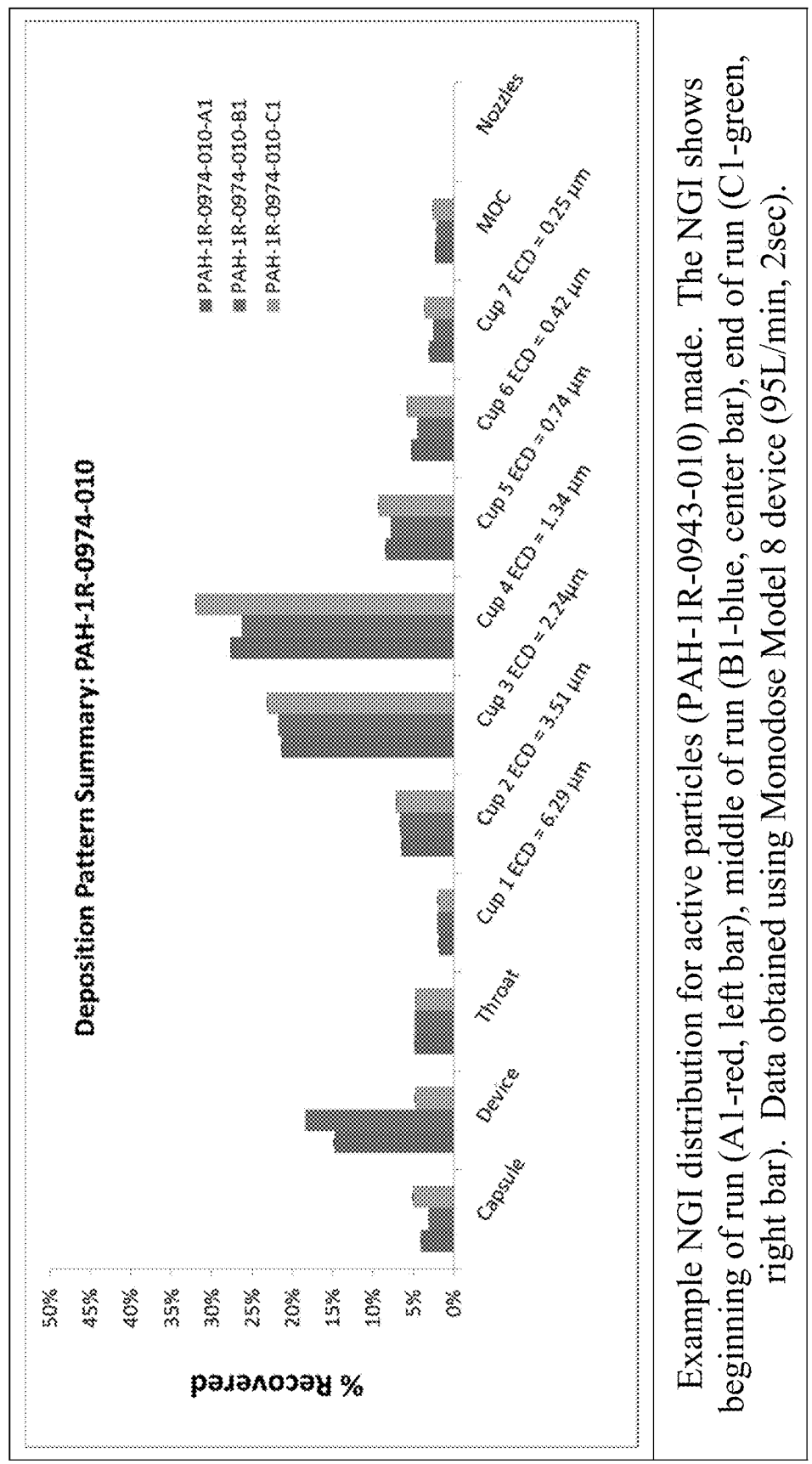
FIG. 2 shows an example NGI distribution for active particles (PAH-1R-0943-010). For each of the three data sets represented for each collection cup, the beginning of the run is the left hand bar (A1), the middle of the run is the center bar (B1), and the end of the run is the right hand bar (C1). Data was obtained using the Monodose Model 8 device (95 L/min, 2 sec).

In some embodiments, the particle uniformity from batch-to-batch provides the present invention with an unexpected and exceptional advantage over the prior art. In certain embodiments, the uniformity within any given batch is unexpected and exceptionally advantageous over the prior art. The present invention includes highly conserved batch uniformity as shown in the following data. See the table below and also FIG. 2.

Uniformity: Sample aerosol data (NGI) for active particles (PAH-1R-0974-010)

| Sample | MMAD | GSD | ED (% rec) | FPF (% ED) | F345 (fill) |
|---|---|---|---|---|---|
| PAH-1R-0974-010-A1 First | 1.74 | 1.88 | 81% | 88% | 42% |
| PAH-1R-0974-010-B1 Middle | 1.80 | 1.87 | 78% | 87% | 44% |
| PAH-1R-0974-010-C1 Last | 1.72 | 1.87 | 90% | 89% | 40% |

In the example shown, fine particle fraction remained within plus/minus 1 percent within a single batch run.

Capsule Filling and Packaging

In some embodiments, HPMC capsules are filled with the DP-intermediate in a humidity controlled ISO 8 environment using an XCELODOSE® (Capsugel) instrument. The filled HPMC capsules are packaged in a low humidity environment. Ten capsules are placed in a DESICAP® Vial and closed with a DESICAP® Cap. The closed vial is then placed into a foil bag with a desiccant canister prior to heat sealing the foil bag to form the packaged drug product.

Stability Studies

According to the formulation of the present drug particle, it was desired to minimize uncontrolled exposure to ambient humidity. The drug particles according to embodiments of the present invention are shown to be stable for at least 9 months when stored under controlled humidity conditions at 25° C./60% RH. In some embodiments, the drug particles are shown to be stable for at least 6 months when stored under controlled humidity conditions at 40° C./75% RH. In some embodiments, the drug particles are shown to be stable for at least 9 months when stored under desiccated conditions at 25° C./60% RH. In some embodiments, the drug particles are shown to be stable for at least 6 months when stored under desiccated conditions at 40° C./75% RH. Studies were conducted to determine the stability of the drug particles at 25° C./60% RH and 40° C./75% RH.

Prototype Stability Study

The purpose of the Prototype Stability Study was to evaluate the stability of drug particles in capsules. Both the 25 and 75 µg strengths were evaluated when stored at 25° C./60% RH and 40° C./75% RH. For the study, drug particles were placed into size 3 HPMC opaque capsules (Capsugel Vcaps). Ten filled capsules were placed into HDPE vials (Desicap) which were sealed with a stopper. The stoppered vial was placed into a foil overwrap with desiccant sachets.

Data for the 25 µg dose drug particles stored at 25° C./60% RH is shown in the table below.

| | | | Time Points | | | | |
|---|---|---|---|---|---|---|---|
| Test | Specifications | | Initial | 1 Month | 3 Months | 6 Months | 9 Months |
| Assay | 0.450-0.550% w/w Treprostinil as free acid (%) | | 0.489 | 0.520 | 0.493 | 0.494 | 0.486 |
| Aerodynamic Particle Size Distribution | Report Results | MMAD (µm) | 1.92 | 2.11 | 2.2 | 2.1 | 2.1 |
| | | GSD (µm) | 1.72 | 1.67 | 1.6 | 1.6 | 1.7 |
| | | FPF (%) | 87 | 84 | 82.9 | 83.6 | 83.6 |
| Delivered Dose Uniformity | Report Results | Average (µg) | 19.9 | 21.6 | 19.65 | 19.47 | 18.86 |

Data for the 25 µg dose drug particles stored at 40° C./75% RH is shown in the table below.

| | | | Time Points | | | |
|---|---|---|---|---|---|---|
| Test | Specifications | | Initial | 1 Month | 3 Months | 6 Months |
| Assay | 0.450-0.550% w/w Treprostinil as free acid (%) | | 0.489 | 0.512 | 0.502 | 0.492 |
| Aerodynamic Particle Size Distribution | Report Results | MMAD (µm) | 1.92 | 2.09 | 2.1 | 2.1 |
| | | GSD (µm) | 1.72 | 1.65 | 1.6 | 1.6 |
| | | FPF (%) | 87 | 85 | 84.8 | 84.7 |
| Delivered Dose Uniformity | Report Results | Average (µg) | 19.9 | 21.2 | 18.86 | 19.28 |

Data for the 75 µg dose drug particles stored at 25° C./60% RH is shown in the table below.

| Test | Specifications | | Initial | 1 Month | 3 Months | 6 Months | 9 Months |
|---|---|---|---|---|---|---|---|
| Assay | 0.450-0.550% w/w Treprostinil as free acid (%) | | 0.489 | 0.500 | 0.496 | 0.494 | 0.487 |
| Aerodynamic Particle Size Distribution | Report Results | MMAD (µm) | 2.13 | 2.17 | 2.2 | 2.2 | 2.2 |
| | | GSD (µm) | 1.60 | 1.61 | 1.6 | 1.6 | 1.6 |
| | | FPF (%) | 85 | 84 | 84.2 | 83.7 | 82.3 |
| Delivered Dose Uniformity | Report Results | Average (µg) | 63.6 | 63.0 | 60.76 | 59.62 | 60.01 |

Data for the 75 µg dose drug particles stored at 40° C./75% RH is shown in the table below.

| Test | Specifications | | Initial | 1 Month | 3 Months | 6 Months |
|---|---|---|---|---|---|---|
| Assay | 0.450-0.550% w/w Treprostinil as free acid (%) | | 0.489 | 0.509 | 0.506 | 0.491 |
| Aerodynamic Particle Size Distribution | Report Results | MMAD (µm) | 2.13 | 2.14 | 2.2 | 2.1 |
| | | GSD (µm) | 1.60 | 1.61 | 1.6 | 1.6 |
| | | FPF (%) | 85 | 85 | 84.8 | 85.3 |
| Delivered Dose Uniformity | Report Results | Average (µg) | 63.6 | 61.0 | 59.86 | 59.42 |

Clinical Trial Material Stability Study

The purpose of the Clinical Trial Material Stability Study was to evaluate the stability of drug particles in capsules. Three strengths were evaluated: 25, 50, and 75 µg active agent doses within capsules. As in the previous study, two storage conditions were evaluated: 25° C./60% RH and 40° C./75% RH. For the study, drug particles were placed into size 3 HPMC opaque capsules (Capsugel Vcaps). Ten filled capsules were placed into HDPE vials (DESICAP) which were sealed with a stopper. The stoppered vial was placed into a foil overwrap with desiccant sachets.

Data for the 25 µg dose drug particles stored at 25° C./60% RH is shown in the table below.

| Test | Specifications | | Initial | 1 Month | 3 Months | 6 Months |
|---|---|---|---|---|---|---|
| Assay | 0.450-0.550% w/w Treprostinil as free acid (%) | | 0.520 | 0.505 | 0.504 | 0.504 |
| Aerodynamic Particle Size Distribution | Report Results | MMAD (µm) | 2.3 | 2.3 | 2.2 | 2.1 |
| | | GSD (µm) | 1.6 | 1.6 | 1.6 | 1.6 |
| | | FPF (%) | 84.1 | 82.7 | 83.6 | 85.0 |
| Delivered Dose Uniformity | Report Results (µg) | Average (µg) | 19.784 | 20.48 | 19.24 | 19.47 |

Data for the 25 µg dose drug particles stored at 40° C./75% RH is shown in the table below.

| Test | Specifications | | Initial | 1 Month | 3 Months | 6 Months |
|---|---|---|---|---|---|---|
| Assay | 0.450-0.550% w/w Treprostinil as free acid (%) | | 0.520 | 0.518 | 0.501 | 0.506 |
| Aerodynamic Particle Size Distribution | Report Results | MMAD (µm) | 2.3 | 2.2 | 2.2 | 2.2 |
| | | GSD (µm) | 1.6 | 1.6 | 1.6 | 1.6 |
| | | FPF (%) | 84.1 | 84.1 | 85.8 | 84.7 |
| Delivered Dose Uniformity | Report Results | Average (µg) | 19.784 | 20.73 | 18.89 | 18.80 |

Data for the 50 µg dose drug particles stored at 25° C./60% RH is shown in the table below.

| Test | Specifications | | Time Points | | | |
|---|---|---|---|---|---|---|
| | | | Initial | 1 Month | 3 Months | 6 Months |
| Assay | 0.450-0.550% w/w Treprostinil as free acid (%) | | 0.515 | 0.509 | 0.509 | 0.506 |
| Aerodynamic Particle Size Distribution | Report Results | MMAD (µm) | 2.2 | 2.2 | 2.2 | 2.2 |
| | | GSD (µm) | 1.6 | 1.6 | 1.6 | 1.6 |
| | | FPF (%) | 86.2 | 85.6 | 85.7 | 85.3 |
| Delivered Dose Uniformity | Report Results (µg) | Average (µg) | 40.417 | 40.75 | 39.14 | 40.05 |

Data for the 50 µg dose drug particles stored at 40° C./75% RH is shown in the table below.

| Test | Specifications | | Time Points | | | |
|---|---|---|---|---|---|---|
| | | | Initial | 1 Month | 3 Months | 6 Months |
| Assay | 0.450-0.550% w/w Treprostinil as free acid (%) | | 0.515 | 0.520 | 0.505 | 0.501 |
| Aerodynamic Particle Size Distribution | Report Results | MMAD (µm) | 2.2 | 2.2 | 2.2 | 2.2 |
| | | GSD (µm) | 1.6 | 1.6 | 1.6 | 1.6 |
| | | FPF (%) | 86.2 | 86.5 | 86.2 | 84.1 |
| Delivered Dose Uniformity | Report Results | Average (µg) | 40.417 | 39.55 | 38.96 | 37.50 |

Data for the 75 µg dose drug particles stored at 25° C./60% RH is shown in the table below.

| Test | Specifications | | Time Points | | | |
|---|---|---|---|---|---|---|
| | | | Initial | 1 Month | 3 Months | 6 Months |
| Assay | 0.450-0.550% w/w Treprostinil as free acid (%) | | 0.517 | 0.512 | 0.509 | 0.508 |
| Aerodynamic Particle Size Distribution | Report Results | MMAD (µm) | 2.3 | 2.3 | 2.3 | 2.2 |
| | | GSD (µm) | 1.6 | 1.6 | 1.6 | 1.6 |
| | | FPF (%) | 84.8 | 84.1 | 84.5 | 85.1 |
| Delivered Dose Uniformity | Report Results (µg) | Average (µg) | 61.851 | 63.91 | 59.88 | 60.25 |

Data for the 75 µg dose drug particles stored at 40° C./75% RH is shown in the table below.

| Test | Specifications | | Time Points | | | |
|---|---|---|---|---|---|---|
| | | | Initial | 1 Month | 3 Months | 6 Months |
| Assay | 0.450-0.550% w/w Treprostinil as free acid (%) | | 0.517 | 0.513 | 0.503 | 0.495 |
| Aerodynamic Particle Size Distribution | Report Results | MMAD (µm) | 2.3 | 2.3 | 2.2 | 2.2 |
| | | GSD (µm) | 1.6 | 1.6 | 1.6 | 1.6 |
| | | FPF (%) | 84.8 | 85.1 | 85.8 | 84.9 |
| Delivered Dose Uniformity | Report Results | Average (µg) | 61.851 | 61.94 | 58.61 | 58.17 |

Dry Powder Inhalation Device

Figure 11:
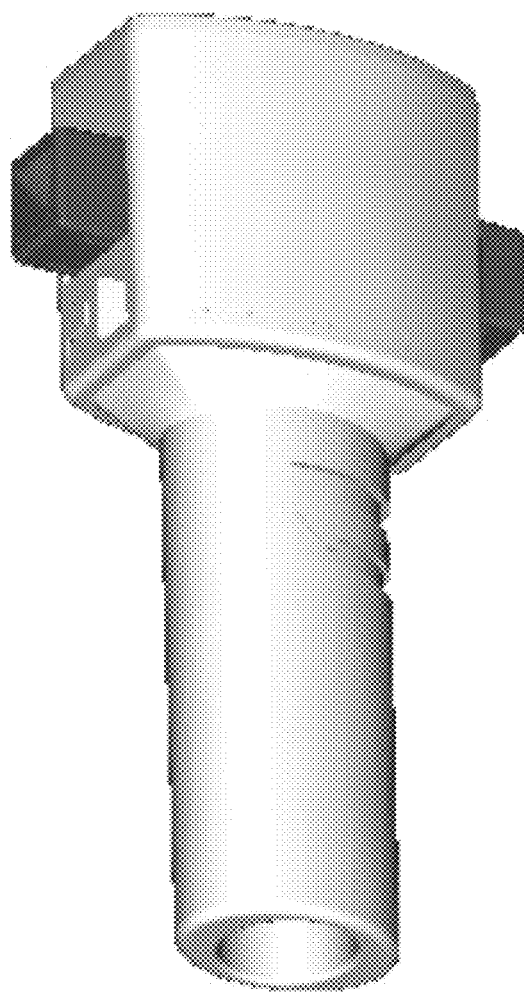
FIG. 11 shows an example dry powder inhalation device which may be used to deliver particles to a patient in accordance with embodiments of the present invention.

The RS00 Model 8 is a commercially available monodose dry powder inhalation device that is manufactured by Plastiape S.p.A (Italy) in accordance with ISO and FDA standards. The overall design of RS00 Model 8 device is shown in FIG. 11.

A cap, which is retained on the mouthpiece, is designed to prevent ingress of dirt and other foreign material into the inhaler when not in use. The plastic side portions cover the air inlet holes, but the cap does not provide a hermetic seal to the device. The cap does not form part of the actuation process.

When assembled, the mouthpiece is mounted on the inhaler body, but is removable for cleaning purposes. To assemble the mouthpiece, the off-set peg at the base of the mouthpiece is placed into the corresponding hole in the inhaler body and the mouthpiece is rotated until it snaps closed. The snap closure ensures that the mouthpiece and inhaler body are properly aligned and that no spurious airflow occurs. The mouthpiece contains a mesh that aids particle size reduction and prevent capsule ingestion during inhalation.

The inhaler body component contains two side buttons, each housing four pins for piercing a capsule. The pins are inserted in the corresponding housing of the pushbuttons and the heads of the pins are retained in their position by a back-plate that is ultrasonically welded to the pushbutton. The buttons and pins are each maintained in their outward position by four small steel springs in each button. A three-component snap-lock system on the inhaler body ensures correct alignment of the mouthpiece when closed.

A capsule piercing area is located internally, adjacent to the pins. When a capsule is inserted in this area, depressing the buttons causes the button pins to pierce the capsule ends, thereby preparing the capsule for emptying. Above the capsule piercing area, there are 2 tangential air inlets and a circular chamber. These allow the capsule to spin when the patient inhales through the device. Capsule spinning creates a centrifugal effect on the powder that promotes efficient emptying.

The performance of the premetered dry powder inhaler is a combination of the characteristics of LIQ861 (including the powder and capsule) and the inhalation device itself.

Nonclinical Studies

Treprostinil is a tricyclic benzidine analogue of endogenous $PGI_2$. The major pharmacologic actions of treprostinil are direct vasodilation of pulmonary and systemic arterial vascular beds and inhibition of platelet aggregation. It was developed for chronic administration as a continuous subcutaneous infusion as a treatment for patients with PAH. $PGI_2$, an endothelial cell derived substance, is a potent vasodilator and inhibitor of platelet aggregation. The hemodynamic properties of treprostinil are similar to those of $PGI_2$ but, unlike $PGI_2$, treprostinil is chemically stable.

A series of in vivo studies were conducted to evaluate pharmokinetics (PK) and toxicology of the present invention dry powder treprostinil formulation.

Pilot, Non-GLP, Single-Dose, Inhalation PK Study of Treprostinil in Dogs (Study 19073)

This study compared the single dose PK of LIQ861 (administered via DPI) to Tyvaso (administered via nebulizer) at a target lung deposition of 3 µg/kg in 3 beagle dogs. Results showed generally similar treprostinil PK profiles following dosing with LIQ861 compared with Tyvaso. In this pilot single administration PK study, treprostinil (dry powder formulation; estimated lung deposition of 3.0 to 3.4 µg/kg) and treprostinil (nebulized liquid; target lung deposition of 3 µg/kg) were compared in 3 beagle dogs. The results showed generally similar treprostinil PK profiles following dosing with treprostinil (dry powder formulation) compared with treprostinil (nebulized liquid). The study design and results are discussed in more detail herein.

The applicants conducted a study comparing plasma concentrations and pharmacodynamics (PD) following administration of treprostinil sodium (nebulized liquid versus a dry powder formulation similar to the LIQ861 formulation of the present invention) as a single inhalation exposure (via controlled ventilation) to anesthetized beagle dogs. Treprostinil sodium was prepared as a nebulized liquid from the same DS used to prepare the dry powder formulation. The dry powder formulation was manufactured using PRINT Technology and utilized the same drug substance, treprostinil sodium, but was different in excipient concentrations compared to LIQ861. Importantly, the excipient concentrations of the present invention provide highly consistent and reproducible batch to batch manufacturing of the LIQ861 product. The formulations used in this study will be referred to as treprostinil (nebulized liquid) and treprostinil (dry powder formulation), respectively, in description of this study. The study design, results, and conclusions are described below.

In study 19073, 3 dogs received a single inhalation administration of nebulized treprostinil (nebulized liquid; estimated lung deposition of 3.4 µg/kg). After a 2-day washout, the dogs received a single inhalation administration of treprostinil (dry powder formulation; estimated lung deposition of 3.0 to 3.4 µg/kg). Blood was collected for plasma analysis of treprostinil concentrations prior to each administration and at 2, 5, 10, 20, 30, 60, 120, and 180 minutes after the completion of each administration. In addition, 2 different dogs (one assigned to each treprostinil formulation) were used to monitor the following PD endpoints (hemodynamic changes): systemic arterial blood pressures [mean arterial pressure (MAP, mmHg), systolic arterial pressure (mmHg), diastolic arterial pressure (mmHg)], pulmonary artery pressure (PAP, mmHg), right atrial pressure (RAP, mmHg), pulmonary capillary wedge pressure (PCWP, mmHg) or left atrial pressure (mmHg), cardiac output (CO, L/min the average of 3), total peripheral resistance (TPR), pulmonary vascular resistance (PVR), and heart rate (HR). The PD effects were assessed prior to initiation of dose administration and at target times of 5, 10, 20, 30, 60, 120, and 180 minutes after the completion of the administration. In contrast to the first three dogs, the dogs assigned to monitor the PD effects were anesthetized for the duration of data collection. The dog assigned treprostinil (nebulized liquid) received an estimated lung deposition of 4.0 µg/kg and the dog assigned to treprostinil (dry powder formulation) received an estimated lung deposition of 2.5 µg/kg. Blood was collected at the same time points as first 3 dogs.

Treprostinil (nebulized liquid and dry powder formulation) had no effect on HR, PAP, RAP, PCWP, or CO, but had a slight effect on decreasing and then increasing arterial blood pressure. Treprostinil (nebulized liquid) appeared to decrease stroke volume, increase TPR, and decrease PVR. Treprostinil (dry powder formulation) appeared to increase stroke volume, decrease TPR, and decrease PVR. The Study Director concluded that the pilot data were inconclusive for comparing the potential PD effects of treprostinil (nebulized liquid) to the treprostinil (dry powder formulation) formulation; however, there appeared to be no important differences in PD effects associated with administration of treprostinil in either formulation.

Pilot, Non-GLP, Single-Dose, Inhalation PK Study of LIQ861 in Male Rats (Study 75670)

This study evaluated the PK of treprostinil in male rats following single inhalation of a range of LIQ861 doses up to a feasible dose. Systemic exposure data from this study was used to determine appropriate doses and blood sampling times for a definitive, comparative PK bridging study of LIQ861 and nebulized treprostinil. Results from this study were used to select dose levels and an optimal blood sampling paradigm for a definitive PK bridging study.

Summary: Study 75670

The objective of the study was to determine the pharmacokinetic profile of treprostinil in male Sprague Dawley rats when administered as the test item, PRINT Treprostinil dry powder (PRINT-Tre), as a single 4 hour inhalation at targeted dose levels of 0.15, 0.75, and 1.5 mg/kg. Results from this study will be used to determine appropriate dose levels and sampling time points for a definitive PK bridging study.

The test item was administered once by inhalation to 3 male rats per group as described in the table below:

| Group No. | Group Designation | Achieved Mean Total Inhaled Dose Level of Treprostinil (mg/kg/day) | Achieved Aerosol Concentration of Treprostinil (µg/L) | Achieved Aerosol Concentration of Trehalose (µg/L) |
|---|---|---|---|---|
| 1 | Low Dose | 0.158 | 1.06 | 150.46 |
| 2 | Mid Dose | 0.707 | 4.72 | 664.85 |
| 3 | High Dose | 1.409 | 9.39 | 1298.81 |

Assessments of mortality, clinical signs and body weights were performed. Blood samples were collected and analyzed for treprostinil content.

No mortality occurred. No clinical signs were observed and body weights were unaffected.

The overall achieved gravimetric and analytical aerosol concentrations for all groups were within 16% of the targeted concentrations. Corresponding average treprostinil dose levels for all groups were within 7% of the targeted dose levels and a clear dose differentiation between groups for each sex was achieved. The gravimetric particle size MMADs from all groups were between 1.2 and 1.6 µm (GSD 2.06 to 2.56). For both treprostinil and trehalose, the chemical determination of particle size distribution ranged from 1.3 to 1.8 µm with the corresponding GSDs between 1.65 and 2.15. The particle size distribution was considered respirable gravimetrically and chemically.

Mean PK parameters for PRINT-Tre treatment groups obtained by non-compartmental analysis of the mean treprostinil plasma concentration data sets are summarized as follows:

| Group | | $T_{1/2}$ (hr) | $T_{max}$ (hr) | $C_{max}$ (ng/mL) | $AUC_{0-Tlast}$ (hr*ng/mL) | $AUC_{INF}$ (hr*ng/mL) |
|---|---|---|---|---|---|---|
| 1 | Mean | 1.01 | 3.75 | 6.800 | 17.320 | 18.335 |
|   | SD | 0.521 | 0.00 | 0.951 | 2.281 | 1.806 |
|   | N | 3 | 3 | 3 | 3 | 3 |
| 2 | Mean | 1.68 | 3.75 | 31.933 | 81.289 | 93.369 |
|   | SD | 0.967 | 0.00 | 9.500 | 19.478 | 19.372 |
|   | N | 3 | 3 | 3 | 3 | 3 |
| 3 | Mean | 1.48 | 3.75 | 46.130 | 121.285 | 137.512 |
|   | SD | 0.619 | 0.00 | 20.580 | 53.331 | 53.418 |
|   | N | 3 | 3 | 3 | 3 | 3 |

In conclusion, single inhalation administration for 4 hours of PRINT-Tre at a high average treprostinil dose of 1.409 mg/kg/day by Sprague-Dawley rats was well tolerated as there were no significant test item related findings. The exposure to treprostinil generally increased in a dose proportional manner between the low dose and the mid dose. The exposure between the mid and high dose increased in a slightly less than dose proportional manner. However, animals in the high dose group were exposed to aerosol concentrations far below target for the last 16 to 26 minutes of inhalation, which may account for the less than dose proportional increase in exposure. Based on these results, similar dose levels are recommended for the following definitive PK study. Blood sampling time points during the test item inhalation period may be adjusted so as to better characterize exposure during test item administration.

Introduction

The objective of the study was to determine the pharmacokinetic profile of treprostinil in male Sprague Dawley rats when administered as the test item, PRINT Treprostinil dry powder (PRINT-Tre), as a single 4 hour inhalation at targeted dose levels of 0.15, 0.75, and 1.5 mg/kg. Results from this study will be used to determine appropriate dose levels and sampling time points for a definitive PK bridging study.

The study was not performed in compliance with GLP regulations but followed appropriate Standard Operating Procedures (SOPs).

Experimental Design

The test item was administered to groups of rats by inhalation administration for one day as described in the table below:

| Group No. | Group Designation | Targeted Total Inhaled Dose Level of Treprostinil (mg/kg/day)[a] | Targeted Aerosol Concentration of Treprostinil (µg/L) | Targeted Aerosol Concentration of Trehalose (µg/L) | No. of Animals Males |
|---|---|---|---|---|---|
| 1 | Low Dose | 0.15 | 1 | 130.7 | 3 |
| 2 | Mid Dose | 0.75 | 5 | 653.5 | 3 |
| 3 | High Dose | 1.5 | 10 | 1306.9 | 3 |

[a] = Targeted aerosol concentrations were calculated based on an estimated body weight of 0.250 kg Following dosing, a series of 6 blood samples for pharmacokinetic evaluation were taken.

Characterization of Test Item

| Test item*: | Identity: | PRINT Treprostinil |
|---|---|---|
| | Content: | 92.75% of Trehalose, 4% of Leucine, 2% of Tween80, 0.26% of NA Citrate Dihydrate, 0.25% of NaCl: 0.74% of Treprostinil sodium (0.67% treprostinil) |
| | Storage Conditions: | Cool (2 to 8° C.), protect from moisture (e.g., dessicant) |
| | Handling Precautions: | Standard laboratory precautions. Handle under dry conditions (Relative Humidity ≤23%) |
| | Supplier: | Liquidia Technologies Inc. |

Treatment

Acclimatization to Exposure System

Before the animals were exposed to the aerosol of the test item, rats were accustomed to the restraint procedure over a period of 3 days. The animals were gradually accustomed to restraint in the dosing tubes used during the exposures up to the duration that was used for aerosol administrations.

Animal Exposure

Exposure system used: Flow-past rodent inhalation exposure system

Exposure method: Inhalation by nose-only exposure

Test Item type: Dry-Powder formulation

Generation method: Piston feed/rotating brush generator

Duration of exposure: 240 minutes

The target aerosol concentrations and dose levels were as follows:

| Group No. | Group Designation | Targeted Dose Level of Treprostinil (mg/kg/day)$^a$ | Targeted Aerosol Concentration of Treprostinil (μg/L) | Targeted Aerosol Concentration of Trehalose (μg/L) |
|---|---|---|---|---|
| 1 | Low Dose | 0.15 | 1 | 130.7 |
| 2 | Mid Dose | 0.75 | 5 | 653.5 |
| 3 | High Dose | 1.5 | 10 | 1306.9 |

$^a$= Target aerosol concentrations were calculated based on an estimated body weight of 0.250 kg.

Estimation of Achieved Dose Levels

The target dose levels were estimated using the following formula:

$$D_L = \frac{E_c \times RMV \times T}{BW}$$

$D_L$=Achieved dose levels (mg/kg/day)

$E_c$=Actual concentration delivered to the animals (mg/L air)

RMV=Respiratory Minute Volume (L/min) according to the method of Bide, Armour and Yee J. App. Toxicol., Vol. 20, 2000: RMV(L/min)=0.499× BW (kg)$^{0.809}$ T=Time, duration of daily exposure (min.)

BW=Mean body weight (kg) during exposure period.

This estimation of total inhaled dose assumed 100% deposition within the respiratory tract.

Inhalation Exposure System

The powder aerosol was produced using a piston feed/rotating brush generator. The aerosol produced was diluted as necessary to achieve the target aerosol concentration and discharged through a 40-mm diameter tube into a flow-past inhalation exposure system. The airflow rate through the exposure system was monitored and recorded manually during each aerosol generation period. Airflow to the exposure system was controlled by the absolute volume of air supplying the generation apparatus using variable area flowmeters. Control of the aerosol exhaust flow from the animal exposure system was achieved using an exhaust valve, and the overall balance of airflows in the exposure system was monitored using pressure gauges. The system provided a minimum of 1.0 L/min to each animal exposure port and was balanced to ensure a slight positive pressure at the site of the proposed animal exposure. This ensured that there was no dilution of the generated aerosol. An equal delivery of aerosol to each proposed exposure position was achieved by employing a distribution network that was identical for each individual exposure position attached to the system.

Inhalation System Monitoring

Determinations of aerosol concentration, particle size distribution, oxygen concentration, relative humidity and temperature were measured on samples collected from a representative port of the exposure chamber. The sample flow rates were precisely controlled using variable area flow meters that were calibrated before use using a primary airflow calibrator. The absolute volume of each aerosol concentration sample was measured with a wet type gas meter.

Oxygen Concentration

The oxygen concentration of the generated atmosphere was measured once during each aerosol exposure. Oxygen concentrations of the exposure atmospheres were maintained between 19-23%.

Relative Humidity/Temperature

The temperature and relative humidity of the generated atmosphere were measured once during each aerosol exposure. Temperatures of the exposure atmospheres were maintained between 19-24° C.

Determination of Aerosol Concentration

At least one aerosol concentration filter sample was collected on glass fiber filter and weighed on each day in order to measure the gravimetric concentration of the test item in the generated aerosol. The filter samples were transferred to the analytical chemistry laboratory for chemical determination of Treprostinil and Trehalose concentrations using an analytical method (Study No. 41609 and Study No. 41635).

Determination of the Particle Size Distribution and Mass Median Aerodynamic Diameter (MMAD)

The distribution of particle size in the generated aerosols was measured once during each exposure by collecting samples into a 7-Stage Mercer Cascade Impactor. The MMAD and the Geometric Standard Deviation (GSD) were calculated based on the results obtained from the impactor using a log-probit transformation.

In-Life Observations

Mortality

Mortality checks were performed at least once a day during all phases of the study.

Clinical Observations

Cage-side clinical signs (ill health, behavioral changes etc.) were recorded at least once daily during all phases of the study, except on detailed clinical examination days, where the cage-side clinical signs were replaced by a DCE.

A detailed clinical examination of each rat was performed on arrival as part of the health status, as well as on Day 1, prior to dosing.

Animal whose health status was judged to warrant additional evaluation was examined by a Clinical Veterinarian.

Body Weights

Body weights were recorded for all animals once at arrival as per health status, once prior to group assignment and on Day 1 (prior to dosing).

Pharmacokinetics

A series of 6 blood samples (approximately 0.3 mL each) was collected from each rat on Day 1 at −15, 5, 15, 30, 75 and 105 minutes after treatment. Thus a total blood volume of 1.8 mL was taken from each rat during the course of the study. For this purpose, each rat (unanesthetized) was bled by jugular venipuncture and the samples were collected into tubes containing the anticoagulant, $K_2EDTA$. Tubes were placed on wet ice pending processing.

Following collection, the samples were centrifuged (2500 rpm for 10 minutes at approximately 4° C.) and the resulting plasma was recovered and stored frozen (≤−60° C.) in labeled tubes.

Deviations to the pharmacokinetic time points were noted in the raw data and were made available with the samples. The location of blood withdrawal was noted in the raw data.

Non-compartmental analysis of treprostinil concentrations in plasma were performed by using the Phoenix WinNonlin 6.3 software.

The following configuration was used for the analysis:
Sampling Method: Sparse
AUC Calculation Method: Linear Trapezoidal with Linear Interpolation

Lambda Z ($\lambda_z$) Method: Best fit for λz, Log regression

Weighting ($\lambda_z$ calculation): Uniform
Pharmacokinetic parameters (including abbreviation and description for each parameter) are described in the following table:

| Parameters | Abbreviation | Unit* |
|---|---|---|
| Area under the plasma drug concentration-time curve from the time of dosing to the last quantifiable concentration | $AUC_{0-Tlast}$ | μg*hr/mL |
| Area under the plasma drug concentration-time curve from the time of dosing extrapolated to infinity | $AUC_{INF}$ | μg*hr/mL |
| Terminal elimination half-life | $T_{1/2}$ | hr |
| The maximum plasma concentration | $C_{max}$ | μg/mL |
| Time to maximum plasma concentration | $T_{max}$ | hr |

*Different units may be presented in the study report

Data Evaluation and Statistics

Numeric and non-numeric data obtained during the study were reported only as individual values.

Results

Aerosol Concentrations

Achieved gravimetric test atmosphere concentrations were as follows:

| Group No. | Targeted Aerosol Concentration (mg\L) | Achieved Mean Aerosol Concentration (mg\L) | Coefficient of Variation (%) | % of Target |
|---|---|---|---|---|
| 1 | 0.156 | 0.165 | 17.2 | 105.9 |
| 2 | 0.781 | 0.728 | 14.0 | 93.2 |
| 3 | 1.563 | 1.439 | 43.5 | 92.0 |

Achieved analytical test atmosphere concentrations for treprostinil were as follows:

| Group No. | Targeted Aerosol Concentration (μg\L) | Achieved Mean Aerosol Concentration (μg\L) | Coefficient of Variation (%) | % of Target |
|---|---|---|---|---|
| 1 | 1 | 1.06 | 17.6 | 105.9 |
| 2 | 5 | 4.72 | 13.9 | 94.4 |
| 3 | 10 | 9.39 | 43.6 | 93.9 |

Achieved analytical test atmosphere concentrations for trehalose were as follows:

| Group No. | Targeted Aerosol Concentration (μg\L) | Achieved Mean Aerosol Concentration (μg\L) | Coefficient of Variation (%) | % of Target |
|---|---|---|---|---|
| 1 | 130.7 | 150.46 | 18.8 | 115.1 |
| 2 | 653.5 | 664.85 | 15.0 | 101.7 |
| 3 | 1306.9 | 1298.81* | 44.1 | 99.4 |

*Last 2 aerosol concentrations samples for trehalose were estimated with a 92.79% difference from gravimetric data as analytical results were BLQ The overall achieved gravimetric and analytical aerosol concentrations for all groups were within 16% of the targeted concentrations. The generated atmospheres were considered stable over the treatment period as % CV were all below 20%, except for Group 3. The increased % CV for Group 3 was caused by the stoppage of the Rotating Brush Generator (RBG) due to lack of test item remaining in the canister with 26 minutes left in the generation (16 minutes of dosing left for animal 3001A, 21 minutes left for animal 3002A and 26 minutes left for animal 3003A). Though a new test item canister was installed on the RBG apparatus, the aerosol concentrations were much lower than targeted for the last 26 minutes. However, the overall aerosol concentrations were still considered acceptable for the study as there was a significant difference in aerosol concentration between groups.

Dose Levels

Overall achieved doses for treprostinil are presented below:

| Group No. | Targeted Dose Levels (mg/kg/day) | Duration of Exposure (min) | Animal | Body Weight (kg) | Estimated Achieved Doses (mg/kg/day) | % from Targeted Dose Level |
|---|---|---|---|---|---|---|
| 1 | 0.15 | 240 | 1001 A | 0.326 | 0.157 | 104.7 |
|   |   |   | 1002 A | 0.309 | 0.159 | 106.0 |
|   |   |   | 1003 A | 0.314 | 0.158 | 105.3 |
|   |   |   | Average |   | 0.158 | 105.3 |
| 2 | 0.75 | 240 | 2001 A | 0.319 | 0.703 | 93.7 |
|   |   |   | 2002 A | 0.308 | 0.708 | 94.4 |
|   |   |   | 2003 A | 0.304 | 0.709 | 94.5 |
|   |   |   | Average |   | 0.707 | 94.3 |
| 3 | 1.5 | 240 | 3001 A | 0.322 | 1.396 | 93.1 |
|   |   |   | 3002 A | 0.321 | 1.397 | 93.1 |
|   |   |   | 3003 A | 0.281 | 1.433 | 95.5 |
|   |   |   | Average |   | 1.409 | 93.9 |

Average achieved dose levels for all groups were within 7% of the targeted dose levels therefore the dose levels were considered acceptable for the study as a clear dose differentiation between groups for each sex was achieved.

Particle Size Distribution

The average gravimetric particle size distribution measurement data were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
|   | 4.60 | 3.00 | 2.10 | 1.60 | 1.10 | 0.70 | 0.33 | 0.00 |   |   |   |
| 1 | 95.8 | 92.4 | 82.4 | 45.4 | 32.4 | 21.5 | 12.3 | 0.0 | 1.2 | 2.28 | 93 |
| 2 | 86.8 | 83.3 | 76.0 | 39.4 | 28.0 | 15.4 | 8.9 | 0.0 | 1.5 | 2.56 | 85 |
| 3 | 94.0 | 90.9 | 77.3 | 30.3 | 13.4 | 8.9 | 5.3 | 0.0 | 1.6 | 2.06 | 90 |

MMAD = Mass median aerodynamic diameter

GSD = Geometric standard deviation.

The average chemical determination of particle size distribution for treprostinil were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
| | 4.60 | 3.00 | 2.10 | 1.60 | 1.10 | 0.70 | 0.33 | 0.00 | | | |
| 1 | 96.4 | 93.9 | 83.3 | 42.8 | 28.1 | 16.5 | 6.9 | 0.0 | 1.3 | 2.06 | 94 |
| 2 | 91.7 | 88.5 | 81.1 | 37.9 | 25.8 | 11.8 | 4.9 | 0.0 | 1.5 | 2.15 | 90 |
| 3 | 95.2 | 91.5 | 76.6 | 25.7 | 8.8 | 5.1 | 1.8 | 0.0 | 1.7 | 1.86 | 91 |

MMAD = Mass median aerodynamic diameter
GSD = Geometric standard deviation.

The average chemical determination of particle size distribution for trehalose were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
| | 4.60 | 3.00 | 2.10 | 1.60 | 1.10 | 0.70 | 0.33 | 0.00 | | | |
| 1 | 95.8 | 91.6 | 81.5 | 38.4 | 24.1 | 13.0 | 4.2 | 0.0 | 1.4 | 2.01 | 93 |
| 2 | 94.4 | 88.9 | 83.3 | 31.5 | 26.0 | 11.1 | 5.6 | 0.0 | 1.4 | 2.11 | 91 |
| 3 | 95.2 | 90.4 | 77.0 | 25.5 | 9.6 | 4.8 | 0.0 | 0.0 | 1.8 | 1.65 | 94 |

MMAD = Mass median aerodynamic diameter
GSD = Geometric standard deviation.

The particle size distribution was considered respirable for this study as the MMADs were below 4 μm and the GSD were within 1.5 and 3.

Exposure Chamber Conditions

Exposure chamber conditions from the reported aerosol concentration exposures are summarized below.

| Group No. | Humidity (% RH) | Temperature (° C.) | Oxygen Concentration (%) |
|---|---|---|---|
| 1 | 31.4 | 21.2 | 20.9 |
| 2 | 34.2 | 21.7 | 20.9 |
| 3 | 26.2 | 20.7 | 20.9 |

Exposure atmosphere oxygen concentrations, temperature and relative humidity ranges were considered acceptable on all occasions.

Mortality

There were no mortalities during the study.

Clinical Signs

There were no adverse clinical signs observed during the study.

Slight decreased activity, piloerection and partially closed eyes were seen in animal 3001A right before the 15 minute time point. However these were not observed afterwards and were not observed in any other animal therefore were not deemed test item related.

Body Weight

Body weights were performed for dose level calculation purposes.

Pharmacokinetics

Following the administration of PRINT-Tre at all achieved dose levels, mean $C_{max}$ ranged from 6.800 to 46.133 ng/mL. The mean maximum plasma concentration ($T_{max}$) was reached at 3.75 hour (15 minutes before end of dosing) for all groups. The mean $AUC_{0-Tlast}$ ($AUC_{INF}$) ranged from 17.320 (18.335) to 121.258 (137.512) hr*ng/mL. Following $T_{max}$, the treprostinil plasma concentrations declined gradually with an estimated mean $T_{1/2}$ ranging from 1.01 to 1.68 hours.

Over the dose range, exposure to treprostinil (based on $C_{max}$, $AUC_{0-Tlast}$ and $AUC_{INF}$) generally increased in dose proportional manner between the low dose (0.158 mg/kg) and the mid dose (0.707 mg/kg). When dose level increased 4.5-fold from low to mid dose, $C_{max}$ and $AUC_{0-Tlast}$ increased 4.7-fold. Treprostinil exposure between the mid dose (0.707 mg/kg) and high dose (1.409 mg/kg) increased in a slightly less than dose proportional manner (2-fold increase in dose with a 1.4-($C_{max}$) to 1.5-fold ($AUC_{0-Tlast}$) increase in exposure). However, because animals in the high dose group were exposed to aerosol concentrations far below target for the last 16 to 26 minutes of the exposure period, exposure levels may have been effected and could account for the less than dose proportional increase in exposure.

Conclusion

Single inhalation administration for 4 hours of PRINT-Tre at a high average treprostinil dose of 1.409 mg/kg/day to Sprague-Dawley rats was well tolerated as there were no significant test item related findings. The exposure to treprostinil generally increased in a dose proportional manner between the low dose and the mid dose. The exposure between the mid and high dose increased in a slightly less than dose proportional manner. However, animals in the high dose group were exposed to aerosol concentrations far below target for the last 16 to 26 minutes of inhalation, which may account for the less than dose proportional increase in exposure. Based on these results, similar dose levels are recommended for the following definitive PK study. Blood sampling time points during the test item inhalation period may be adjusted so as to better characterize exposure during test item administration.

Non-GLP, Single-Dose, Inhalation, Comparative PK Study of LIQ861 and Nebulized Treprostinil in Rats (Study 75658)

This study evaluated and compared the PK profile of LIQ861 to treprostinil (nebulized) to establish a bridge between the two formulations.

The non-GLP, single administration by inhalation, PK study of treprostinil in rats (Study 75658) has been completed by Liquidia (referred to as the definitive PK bridging study). This study compared the systemic exposure of LIQ861 versus nebulized liquid treprostinil sodium. The observed systemic exposures revealed no meaningful differences between formulations, providing a bridge between the LIQ861 formulation and the marketed Tyvaso formulation and thereby permitting use of Tyvaso nonclinical toxicology studies to support the LIQ861 formulation per the 505(b)(2) pathway.

In Study 75658, systemic exposure of LIQ861 versus nebulized treprostinil sodium was compared in rats. LIQ861 was delivered over a 4-hour exposure period at total delivered dose levels of 0.273, 0.762, and 1.50 mg/kg body weight. Nebulized treprostinil sodium was delivered at a single dose level (0.785 mg/kg total delivered dose) for the same exposure period (4 hours) as LIQ861. Blood was collected for plasma analysis of treprostinil concentrations at 30 and 60 minutes following the start of administration, immediately post-administration (240 min), and at 5, 15, 30, 75, and 105 minutes following the end of administration.

Pharmacokinetic parameters from Study 75658. Individual plasma concentrations of treprostinil ranged from 0.345 to 67.4 ng/mL. Maximum plasma concentration was reached 0.5 to 4 hours after the start of the 4-hour exposure period. Maximum concentration (Cmax) and area under the curve (AUC) values were similar between males and females within treatment groups. Dose-related increases in Cmax and AUC values were observed for the three LIQ861 dose groups. Relative bioavailability of LIQ861 compared to nebulized treprostinil based on dose normalized AUC-time curve extrapolated to time infinity (AUCinf) ranged from 1.2 to 2.2.

Summary of Mean Noncompartmental PK Parameters by Treatment and Sex for Study 75658

| Type of inhalation | Group | Achieved Mean Dose Level (mg/kg) | Sex | $R^2$ | $t_{1/2}$ (hr) | $T_{max}$ (hr) | $C_{max}$ (ng/mL) | $AUC_{0-Tlast}$ (hr*ng/mL) | $AUC_{INF}$ (hr*ng/mL) |
|---|---|---|---|---|---|---|---|---|---|
| Treprostinil Sodium (Nebulized) | 1 | 0.785 | Female | 0.99 | 0.59 | 4.00 | 16.2 | 62.4 | 63.5 |
|  |  |  | Male | 0.97 | 0.77 | 0.50 | 16.5 | 59.3 | 60.6 |
| Dry Powder (PRINT treprostinil) | 2 | 0.273 | Female | 0.92 | 1.77 | 4.00 | 5.38 | 22.2 | 24.2 |
|  |  |  | Male | 1.00 | 0.73 | 1.00 | 7.18 | 26.9 | 27.4 |
|  | 3 | 0.762 | Female | 0.97 | 0.66 | 4.00 | 32.8 | 107 | 110 |
|  |  |  | Male | 0.90 | 0.95 | 4.00 | 54.4 | 144 | 149 |
|  | 4 | 1.498 | Female | 0.84 | 0.67 | 0.50 | 44.5 | 174 | 182 |
|  |  |  | Male | 1.00 | 0.90 | 4.00 | 44.1 | 143 | 148 |

Abbreviations: $C_{max}$, maximal concentration;
$T_{max}$, time of maximal concentration;
$AUC_{last}$, area under the concentration-time curve to the last measured timepoint;
$t_{1/2}$, half-life;
$AUC_{inf}$, area under the concentration-time curve extrapolated to time infinity.
PRINT treprostinil = LIQ861 DP-intermediate.

Calculated Relative Bioavailability (Combined Genders) Based on AUCinf (Dose Corrected) from Study 75658

| Group | Treatment | Dose Level (mg/kg) | Mean AUCinf (hr*ng/mL) | Frel (PRINT/ Treprostinil) |
|---|---|---|---|---|
| 1 | Treprostinil | 0.785 | 62.1 | NA |
| 2 | PRINT-treprostinil Low | 0.273 | 25.8 | 1.20 |
| 3 | PRINT-treprostinil Mid | 0.762 | 129 | 2.15 |
| 4 | PRINT-treprostinil High | 1.498 | 165 | 1.39 |

Abbreviations: AUCinf, area under the concentration-time curve extrapolated to time infinity; Frel, relative bioavailability; NA, not applicable. PRINT treprostinil = LIQ861 DP-intermediate.

Summary: Study 75658

The objectives of the study were to determine the pharmacokinetic (PK) profile of Treprostinil in Sprague-Dawley rats when administered as PRINT-Treprostinil (PRINT-Tre) by 4-hour inhalation at 0.15, 0.75, and 1.5 mg/kg, to determine the PK profile of Treprostinil in Sprague-Dawley rats when administered as nebulized Treprostinil sodium in solution (Tre solution) by 4-hour inhalation at 0.75 mg/kg and to compare the PK profiles of Treprostinil when administered as PRINT-Tre and Tre solution.

The test item was administered once to 6 male and 6 female rats per group by nose-only inhalation for 4 hours as described in the table below:

| Group No. | Group Designation | Achieved Mean Total Inhaled Dose Level of Treprostinil (mg/kg/day) | Achieved Aerosol Concentration of Treprostinil (µg/L) | Achieved Aerosol Concentration of Trehalose (µg/L) |
|---|---|---|---|---|
| 1 | Tre Solution | 0.785 | 5.07 | 0 |
| 2 | PRINT-Tre (Low Dose) | 0.273 | 1.76 | 254.84 |
| 3 | PRINT-Tre (Mid Dose) | 0.762 | 4.95 | 719.53 |
| 4 | PRINT-Tre (High Dose) | 1.498 | 9.73 | 1394.33 |

Assessments of mortality, clinical signs and body weights were performed. Pharmacokinetic samples were collected and the analysis of these samples was performed.

No mortality occurred and no clinical signs were observed.

The overall achieved aerosol concentrations for all groups were within 10% of the targeted concentrations gravimetrically and for both treprostinil and trehalose, except for Group 2 which were significantly above the targeted concentrations (76 to 95%). Corresponding average achieved dose levels for all groups were within 5% of the targeted dose levels, except for Group 2 which was 82% above the targeted dose level. However, the dose levels were considered acceptable for the study as a clear dose differentiation between groups for each sex was achieved.

The particle size MMADs from Groups 2 to 4 were between 1.7 and 2.0 μm gravimetrically (GSD 1.90 to 2.67); for both treprostinil and trehalose, chemical particle size distribution ranged from 1.6 to 1.8 μm with the corresponding GSDs between 1.89 and 2.24. The particle size MMAD for Group 1 was 0.5 μm with a corresponding GSD of 2.60. The particle size distribution was considered respirable.

With administration of PRINT-Tre at an achieved dose level of 0.273 mg/kg, 0.762 mg/kg or 1.498 mg/kg, plasma exposure to treprostinil was generally similar in both sexes; however, exposure was slightly lower in females than males at the mid-dose level and slightly higher in females than males at the high-dose level.

Based on $AUC_{0\text{-}Tlast}$, $AUC_{INF}$ and $C_{max}$, values for both sexes, plasma exposure increased more than proportionally between the low- and mid-dose levels. But between the mid- and high-dose levels, plasma exposure increased less than proportionally for females and there was no increase in the exposure for males. The maximum mean treprostinil plasma concentration ($T_{max}$) was at the end of inhalation for both sexes, except for low-dose males and high-dose females, where mean $T_{max}$ was at 1 and 0.5 hours after inhalation began, respectively.

At the low-dose level, mean treprostinil plasma concentration was similar after 0.5, 1, or 4 hours of inhalation exposure to PRINT-Tre, suggesting that steady state was achieved within the first 30 minutes of exposure. The same was true for females at the high-dose level; however, for males at the high-dose level and for both sexes at the mid-dose level, mean treprostinil plasma concentration was greater at the end of inhalation than after one hour of inhalation. When inhalation ended, treprostinil plasma concentrations declined gradually. Given the degree of individual variation, the estimated mean $T_{1/2}$ values were similar at all dose levels and ranged from 0.7 to 1.8 hours in males and 0.7 to 1.0 hours in females.

For Tre solution, with an administration at 0.785 mg/kg, plasma exposure to treprostinil was generally similar in both sexes. The maximum mean treprostinil plasma concentration ($T_{max}$) was at the end of inhalation. Mean treprostinil plasma concentration was similar after 0.5, 1, or 4 hours of inhalation exposure to Tre solution, suggesting that steady state was achieved within the first 30 minutes of exposure. When inhalation ended, treprostinil plasma concentrations declined gradually, with estimated mean $T_{1/2}$ values of 0.6 hours in males and 0.8 hours in females.

Administration of PRINT-Tre and Tre solution at nearly equivalent dose levels (0.76 and 0.79 mg/kg, respectively) resulted in plasma exposures to treprostinil that were greater with PRINT-Tre than with Tre solution. Specifically, mean $AUC_{0\text{-}Tlast}$ was approximately twice as high (126 versus 61 h*ng/mL, respectively) and mean $C_{max}$ was three times as high (44 versus 16 ng/mL, respectively). As would be expected, once treprostinil entered the systemic circulation, it was cleared from plasma at a similar rate, with mean $T_{1/2}$ values of 0.7 to 1.0 hours for PRINT-Tre and 0.6 to 0.8 hours for Tre solution.

In conclusion, single inhalation administration for 4 hours of PRINT Treprostinil at a high average dose of 1.498 mg/kg/day to Sprague-Dawley rats was well tolerated as there were no test item related findings. At an equivalent dose level, plasma exposures to treprostinil was greater with PRINT-Tre than with Tre solution; specifically, mean $AUC_{0\text{-}Tlast}$ was approximately twice as great and mean $C_{max}$ was three times as great. As would be expected, once treprostinil entered the systemic circulation, it was cleared from plasma at a similar rate regardless of how it was administered.

The objectives of the study were to:

1. Determine the pharmacokinetic (PK) profile of Treprostinil in Sprague-Dawley rats when administered as PRINT-Treprostinil (PRINT-Tre) by 4-hour inhalation at 0.15, 0.75, and 1.5 mg/kg.
2. Determine the PK profile of Treprostinil in Sprague-Dawley rats when administered as nebulized Treprostinil sodium in solution (Tre solution) by 4-hour inhalation at 0.75 mg/kg.
3. Compare the PK profiles of Treprostinil when administered as PRINT-Tre and Tre solution.

Experimental Design

The test items were administered to groups of rats by a 4-hour inhalation administration as described in the table below:

| Group No. | Group Designation | Targeted Total Inhaled Dose Level of Treprostinil (mg/kg/day) | Targeted Aerosol Concentration of Treprostinil (μg/L)[a] | Targeted Aerosol Concentration of Trehalose (μg/L)[a] | No. of Animals Males | No. of Animals Females |
|---|---|---|---|---|---|---|
| 1 | Tre Solution | 0.75 | 5 | 0 | 6 | 6 |
| 2 | PRINT-Tre | 0.15 | 1 | 130.7 | 6 | 6 |
| 3 | PRINT-Tre | 0.75 | 5 | 653.5 | 6 | 6 |
| 4 | PRINT-Tre | 1.5 | 10 | 1306.9 | 6 | 6 |

[a] = Target aerosol concentrations were calculated based on an estimated body weight of 0.250 kg During and after the inhalation period, a series of 8 blood samples for pharmacokinetic evaluation were taken.

Justification for Selection of Route of Administration, Species and Dose Levels

The route of administration was chosen because it is the intended human therapeutic route.

The rat was selected because it is a rodent species recommended by various regulatory authorities. Background data are available. Also, rats were used as the test system for previous toxicity studies with Treprostinil sodium solution that supported development and approval of that product. Using rats in the current study allowed comparison with the previous studies.

The high-dose level for PRINT-Tre was the feasible dose attainable based on technical aerosol trials with the test item (Study No. 41610).

The low- and mid-dose levels for PRINT-Tre were selected on the basis of a previous pilot PK study in rats (Study No. 75670).

The dose level for Tre solution was selected to match the mid-dose level of PRINT-Tre to allow direct comparison.

Characterization of Test Items

| | Content: | 92.79% of Trehalose, 4% of Leucine, 2% of Tween80, 0.26% of NA Citrate, 0.24% of NaCl:0.71% of Treprostinil |
|---|---|---|
| | Storage Conditions: | Cool (2 to 8° C.), protected from moisture (e.g., dessicant) |
| | Handling Precautions: | Standard laboratory precautions. Handle under dry conditions (Relative Humidity ≤ 23%) |
| | Supplier: | Liquidia Technologies Inc. |
| Test item 2*: | Identity: | Treprostinil Sodium |
| | Description: | White or pale yellowish powder |
| | Batch No.: | TN115E010 |
| | Expiry Date: | May 28, 2017 |

-continued

| | |
|---|---|
| Purity: | 101.49% |
| Storage Conditions: | Cool (2 to 8° C.) |
| Handling Precautions: | Standard laboratory precautions |
| Supplier: | Yonsung Fine Chemicals Co., LTD |

Preparation of Test Item

PRINT-Tre was used as provided by the Sponsor. A glove box under nitrogen was used for handling, aliquoting or packing of the canisters. Relative humidity (RH) inside the glove box was monitored and recorded using a hygrometer and was kept below 23% RH.

For Group 1, the treprostinil sodium was dissolved in purified water to achieve the desired formulation concentration. A representative sample (0.5 mL in duplicate) was collected to verify the formulation concentration of Treprostinil in the formulation.

Treatment

Acclimatization to Exposure System

Before the animals were exposed to the aerosol of the test item, rats were accustomed to the restraint procedure over a period of 3 days. The animals were gradually accustomed to restraint in the dosing tubes used during the exposures up to the duration that was used for aerosol administrations.

Animal Exposure

Exposure system used: Flow-past rodent inhalation exposure system

Exposure method: Inhalation by nose-only exposure

Test Item type: Solution (Group 1), Dry Powder (Groups 2 to 4)

Generation method: Nebulization (Group 1) and Piston feed/rotating brush generator (Group 2 to 4)

Duration of exposure: 240 minutes

The target aerosol concentrations and dose levels were as follows:

| Group No. | Group Designation | Targeted Dose Level of Treprostinil (mg/kg/day) | Targeted Aerosol Concentration of Treprostinil (μg/L)[a] | Targeted Aerosol Concentration of Trehalose (μg/L) |
|---|---|---|---|---|
| 1 | Tre solution | 0.75 | 5 | 0 |
| 2 | PRINT-Tre (Low Dose) | 0.15 | 1 | 130.7 |
| 3 | PRINT-Tre (Mid Dose) | 0.75 | 5 | 653.5 |
| 4 | PRINT-Tre (High Dose) | 1.5 | 10 | 1306.9 |

[a] = Target aerosol concentrations were calculated based on an estimated body weight of 0.250 kg.

Estimation of Achieved Dose Levels

The target dose levels were estimated using the following formula:

$$D_L = \frac{E_c \times RMV \times T}{BW}$$

$D_L$=Achieved dose levels (mg/kg/day)
$E_c$=Actual concentration delivered to the animals (mg/L air)
RMV=Respiratory Minute Volume (L/min) according to the method of Bide, Armour and Yee 2000 J. App. Toxicol., Vol. 20: RMV (L/min)=0.499×BW (kg)° 0.809
T=Time, duration of daily exposure (min.)
BW=Mean body weight (kg) during exposure period.
This estimation of total inhaled dose assumed 100% deposition within the respiratory tract.

Inhalation Exposure System

The powder aerosol for Groups 2 to 4 was produced using a piston feed/rotating brush generator while the liquid aerosol for Group 1 was produced by metering the flow of the formulation to a clinical nebulizer (Sidestream). The aerosol produced was diluted as necessary to achieve the target aerosol concentration and discharged through a 40-mm diameter tube into a flow-past inhalation exposure system. The airflow rate through the exposure system was monitored and recorded manually during each aerosol generation period. Airflow to the exposure system was controlled by the absolute volume of air supplying the generation apparatus using variable area flowmeters. Control of the aerosol exhaust flow from the animal exposure system was achieved using an exhaust valve, and the overall balance of airflows in the exposure system was monitored using pressure gauges. The system provided a minimum of 1.0 L/min to each animal exposure port and was balanced to ensure a slight positive pressure at the site of the animal exposure. This ensured that there was no dilution of the generated aerosol. An equal delivery of aerosol to each exposure position was achieved by employing a distribution network that was identical for each individual exposure position attached to the system.

Inhalation System Monitoring

Determinations of aerosol concentration, particle size distribution, oxygen concentration, relative humidity and temperature were measured on samples collected from a representative port of the exposure chamber. The sample flow rates were precisely controlled using variable area flow meters that were calibrated before use using a primary airflow calibrator. The absolute volume of each aerosol concentration sample was measured with a wet type gas meter.

Oxygen Concentration

The oxygen concentration of the generated atmosphere was measured once during each aerosol exposure. Oxygen concentrations of the exposure atmospheres were maintained between 19-23%.

Relative Humidity/Temperature

The temperature and relative humidity of the generated atmosphere were measured once during each aerosol exposure. Temperatures of the exposure atmospheres were maintained between 19-24° C.

Determination of Aerosol Concentration

At least one aerosol concentration filter sample was collected for all groups on each aerosol generation. The filter samples from Groups 2 to 4 were weighed in order to measure the gravimetric concentration of the test item in the generated aerosol. The filter samples were transferred to the analytical chemistry laboratory for chemical determination of Treprostinil and Trehalose concentrations. The filter samples for Group 1 were not weighed gravimetrically and were only transferred to the analytical laboratory for determination of Treprostinil concentrations. The analysis in the analytical laboratory was performed using an analytical method (Study No. 41609).

Determination of the Particle Size Distribution and Mass Median Aerodynamic Diameter (MMAD)

The distribution of particle size in the generated aerosols was measured once for Groups 1 to 4 by collecting samples into a 7-Stage Mercer Cascade Impactor. All sample substrates obtained from Groups 2 to 4 were weighed gravimetrically and then transferred to the analytical chemistry laboratory for chemical determination of particle size of aerosolized Treprostinil and Trehalose. All sample substrates obtained from Group 1 were only transferred to the analytical laboratory for chemical determination of particle size of aerosolized Treprostinil. The analysis in the analytical laboratory was performed using an analytical method (Study No. 41609).

The MMAD and the Geometric Standard Deviation (GSD) were calculated based on the results obtained from the impactor using a log-probit transformation.

Reporting of Analytical Results

The analytical report containing the results from the filter and particle size distribution sample analyses were prepared. Any samples not employed in the primary analysis or any remaining sample from the primary analysis were retained until it was determined by the analyst and Study Director that it was not be required for confirmatory analysis. These samples were discarded and their disposition recorded in the raw data.

In-Life Observations

Mortality

Mortality checks were performed at least once a day during all phases of the study.

Clinical Observations

Cage-side clinical signs (ill health, behavioral changes etc.) were recorded at least once daily during all phases of the study, except on detailed clinical examination days, where the cage-side clinical signs were replaced by a DCE.

A detailed clinical examination of each rat was performed on arrival as part of the health status, as well as on Day 1, prior to dosing.

Body Weights

Body weights were recorded for all animals once at arrival as per health status, once prior to group assignment and on Day 1 (prior to dosing).

Pharmacokinetics

A series of 8 blood samples (approximately 0.3 mL each) was collected 30 minutes and 1 hour after exposure began, immediately after exposure ended (IPE), and again at 5, 15, 30, 75 and 105 minutes post-dosing as per the table below. Thus a total blood volume of 1.2 mL was taken from each rat during the course of the study. For this purpose, each rat (unanesthetized) was bled by jugular venipuncture and the samples were collected into tubes containing the anticoagulant, $K_2EDTA$. Tubes were placed on wet ice pending processing.

| | | | Toxicokinetic time point | | | | | |
|---|---|---|---|---|---|---|---|---|
| Group Number | Number of animals/sex | 30 min post start | 1 hour post start | 5 min IPE | 15 min post end | 30 min post end | 75 min post end | 105 min post end |
| 1 | 3+ | ✓ | | ✓ | | ✓ | ✓ | |
|   | 3 # |   | ✓ | ✓ | ✓ | ✓ |   | ✓ |
| 2 | 3+ | ✓ | | ✓ | ✓ | ✓ | ✓ | |
|   | 3 # |   | ✓ | ✓ | ✓ | ✓ |   | ✓ |
| 3 | 3+ | ✓ | | ✓ | ✓ | ✓ | ✓ | |
|   | 3 # |   | ✓ | ✓ | ✓ | ✓ |   | ✓ |
| 4 | 3+ | ✓ | | ✓ | ✓ | ✓ | ✓ | |
|   | 3 # |   | ✓ | ✓ | ✓ | ✓ |   | ✓ |

+ animals with the lowest identification numbers
animals with the highest identification numbers Following collection, the samples were centrifuged (2500 rpm for 10 minutes at approximately 4° C.) and the resulting plasma was recovered and stored frozen (≤−60° C.) in labeled tubes.

Deviations to the pharmacokinetic time points were noted in the raw data and were made available with the samples. The location of blood withdrawal was noted in the raw data.

The plasma analysis was performed and the bioanalytical data was prepared for inclusion in the final report.

The pharmacokinetic parameters were calculated and the non-compartmental analysis of PRINT-Tre and Tre solution treprostinil concentrations in plasma was performed by using the Phoenix WinNonlin 6.3 software.

The following configuration was used for the analysis:
Sampling Method: Sparse
AUC Calculation Method: Linear Trapezoidal with Linear Interpolation
Lambda Z ($\lambda_z$) Method: Best fit for λz, Log regression
Weighting ($\lambda_z$ calculation): Uniform Pharmacokinetic parameters (including abbreviation and description for each parameter) were described in the following table:

| Parameters | Abbreviation | Unit* |
|---|---|---|
| Area under the plasma drug concentration-time curve from the time of dosing to the last quantifiable concentration | $AUC_{0-Tlast}$ | μg*hr/mL |
| Area under the plasma drug concentration-time curve from the time of dosing extrapolated to infinity | $AUC_{INF}$ | μg*hr/mL |
| Terminal elimination half-life | $T_{1/2}$ | hr |
| The maximum plasma concentration | $C_{max}$ | μg/mL |
| Time to maximum plasma concentration | $T_{max}$ | hr |

Data Evaluation and Statistics

Numeric and non-numeric data obtained during the study were reported only as individual values.

Results

Formulation Analysis

Formulation concentration for Group 1 was as follows:

| Group No. | Average Targeted Concentration (mg/mL) | Average Measured Concentration (mg/mL) | % of Targeted Concentration |
|---|---|---|---|
| 1 | 0.50 | 0.492 | 98.4 |

The formulation concentration for Group 1 was within 2% of the targeted concentration therefore the formulation concentration was considered acceptable for the study.

Aerosol Concentrations

Achieved gravimetric test atmosphere concentrations were as follows:

| Group No. | Targeted Aerosol Concentration (mg\L) | Achieved Mean Aerosol Concentration (mg\L) | Coefficient of Variation (%) | % of Target |
|---|---|---|---|---|
| 2 | 0.156 | 0.283 | 55.5 | 181.4 |
| 3 | 0.781 | 0.814 | 16.3 | 104.2 |
| 4 | 1.563 | 1.548 | 21.9 | 99.0 |

Achieved chemical test atmosphere concentrations for treprostinil were as follows:

| Group No. | Targeted Aerosol Concentration (μg\L) | Achieved Mean Aerosol Concentration (μg\L) | Coefficient of Variation (%) | % of Target |
|---|---|---|---|---|
| 1 | 5 | 5.07 | 3.6 | 101.4 |
| 2 | 1 | 1.76 | 55.2 | 176.3 |
| 3 | 5 | 4.95 | 19.8 | 99.1 |
| 4 | 10 | 9.73 | 22.3 | 97.3 |

Achieved chemical test atmosphere concentrations for trehalose were as follows:

| Group No. | Targeted Aerosol Concentration (μg\L) | Achieved Mean Aerosol Concentration (μg\L) | Coefficient of Variation (%) | % of Target |
|---|---|---|---|---|
| 2 | 130.7 | 254.84 | 54.4 | 195.0 |
| 3 | 653.5 | 719.53 | 20.5 | 110.1 |
| 4 | 1306.9 | 1394.33 | 23.2 | 106.7 |

The overall achieved aerosol concentrations for all groups were within 10% of the targeted concentrations gravimetrically and for both treprostinil and trehalose, except for Group 2 which were significantly above the targeted concentrations (76% and 95% for treprostinil and trehalose, respectively). The generated atmospheres were considered stable over the treatment period except for Group 2 (CV %~54%). However, the overall aerosol concentrations were still considered acceptable for the study as there was a significant difference in aerosol concentration between groups.

Achieved Dose Levels

Overall achieved doses for treprostinil are presented below:

| Group No. | Targeted Dose Level (mg/kg/day) | Duration of Exposure (min) | Sex | Body Weight (kg) | Estimated Achieved Doses (mg/kg/day) | % from Targeted Dose Level |
|---|---|---|---|---|---|---|
| 1 | 0.75 | 240 | Male | 0.308 | 0.760 | 101.4 |
|   |      |     | Female | 0.212 | 0.817 | 108.9 |
|   |      |     | Combined | 0.260 | 0.785 | 104.7 |
| 2 | 0.15 | 240 | Male | 0.301 | 0.265 | 176.7 |
|   |      |     | Female | 0.211 | 0.284 | 189.1 |
|   |      |     | Combined | 0.256 | 0.273 | 182.3 |
| 3 | 0.75 | 240 | Male | 0.321 | 0.737 | 98.2 |
|   |      |     | Female | 0.215 | 0.795 | 106.0 |
|   |      |     | Combined | 0.268 | 0.762 | 101.6 |
| 4 | 1.5  | 240 | Male | 0.317 | 1.451 | 96.7 |
|   |      |     | Female | 0.219 | 1.557 | 103.8 |
|   |      |     | Combined | 0.268 | 1.498 | 99.9 |

Average achieved dose levels for all groups were within 5% of the targeted dose levels, except for Group 2 which was 82% above the targeted dose level. However, the dose levels were considered acceptable for the study as a clear dose differentiation between groups for each sex was achieved.

Particle Size Distribution

The average gravimetric particle size distribution measurement data were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
|   | 4.60 | 3.00 | 2.10 | 1.60 | 1.10 | 0.70 | 0.33 | 0.00 | | | |
| 2 | 87.9 | 80.0 | 61.0 | 31.2 | 21.8 | 16.2 | 9.1 | 0.0 | 1.7 | 2.67 | 80 |
| 3 | 90.7 | 85.0 | 66.9 | 24.9 | 14.8 | 9.0 | 3.0 | 0.0 | 1.8 | 2.12 | 85 |
| 4 | 91.7 | 84.0 | 61.6 | 23.5 | 8.1 | 4.3 | 0.8 | 0.0 | 2.0 | 1.90 | 86 |

MMAD = Mass median aerodynamic diameter
GSD = Geometric standard deviation.

The average chemical determination of particle size distribution for treprostinil were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
|   | 4.60 | 3.00 | 2.10 | 1.60 | 1.10 | 0.70 | 0.33 | 0.00 | | | |
| 1 | 95.9 | 95.7 | 95.4 | 95.1 | 85.1 | 50.1 | 22.0 | 0.0 | 0.5 | 2.60 | 98 |
| 2 | 94.0 | 86.3 | 64.4 | 29.3 | 19.8 | 14.1 | 6.1 | 0.0 | 1.6 | 2.24 | 87 |
| 3 | 95.3 | 90.3 | 71.5 | 25.9 | 15.2 | 9.3 | 2.7 | 0.0 | 1.6 | 1.97 | 90 |
| 4 | 94.1 | 88.4 | 64.3 | 23.9 | 8.2 | 4.4 | 1.5 | 0.0 | 1.8 | 1.89 | 88 |

MMAD = Mass median aerodynamic diameter
GSD = Geometric standard deviation.

The average chemical determination of particle size distribution for trehalose were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
| | 4.60 | 3.00 | 2.10 | 1.60 | 1.10 | 0.70 | 0.33 | 0.00 | | | |
| 2 | 94.3 | 86.7 | 63.8 | 26.4 | 16.8 | 14.1 | 6.1 | 0.0 | 1.6 | 2.22 | 87 |
| 3 | 96.0 | 92.0 | 72.3 | 22.2 | 12.0 | 8.0 | 4.0 | 0.0 | 1.6 | 1.97 | 90 |
| 4 | 95.7 | 91.4 | 68.0 | 27.9 | 12.8 | 8.6 | 4.3 | 0.0 | 1.6 | 2.00 | 90 |

MMAD = Mass median aerodynamic diameter
GSD = Geometric standard deviation.

The particle size distribution was considered respirable for this study as the MMADs were below 4 μm and the GSD were within 1.5 and 3.

Exposure Chamber Conditions

Exposure chamber conditions from the reported aerosol concentration exposures are summarized below.

| Group No. | Humidity (% RH) | Temperature (° C.) | Oxygen Concentration (%) |
|---|---|---|---|
| 1 | 58.5 | 21.0 | 20.9 |
| 2 | 35.1 | 21.6 | 20.9 |
| 3 | 39.0 | 21.5 | 20.9 |
| 4 | 39.4 | 21.2 | 20.9 |

Exposure atmosphere oxygen concentrations, temperature and relative humidity ranges were considered acceptable on all occasions.

Mortality

There were no mortalities during the study.

Clinical Signs

There were no clinical signs observed during the study.

Body Weight

Body weights were performed for dose level calculation purposes.

Pharmacokinetics

With administration of PRINT-Tre at an achieved dose level of 0.273 mg/kg, 0.762 mg/kg or 1.498 mg/kg, plasma exposure to treprostinil was generally similar in both sexes; however, exposure was slightly lower in females than males at the mid-dose level and slightly higher in females than males at the high-dose level.

Based on $AUC_{0\text{-}Tlast}$, $AUC_{INF}$ and $C_{max}$, values for both sexes, plasma exposure increased more than proportionally between the low- and mid-dose levels. But between the mid- and high-dose levels, plasma exposure increased less than proportionally for females and there was no increase in the exposure for males. The maximum mean treprostinil plasma concentration ($T_{max}$) was at the end of inhalation for both sexes, except for low-dose males and high-dose females, where mean $T_{max}$ was at 1 and 0.5 hours after inhalation began, respectively.

At the low-dose level, mean treprostinil plasma concentration was similar after 0.5, 1, or 4 hours of inhalation exposure to PRINT-Tre, suggesting that steady state was achieved within the first 30 minutes of exposure. The same was true for females at the high-dose level; however, for males at the high-dose level and for both sexes at the mid-dose level, mean treprostinil plasma concentration was greater at the end of inhalation than after one hour of inhalation. These data are summarized below.

| | Males Dose (mg/kg) = | | | Females Dose (mg/kg) = | | |
|---|---|---|---|---|---|---|
| | 0.273 | 0.762 | 1.498 | 0.273 | 0.762 | 1.498 |
| 0.5 hours of inhalation | 6.1 | 22 | 26 | 4.2 | 18 | 44 |
| 1 hour of inhalation | 7.2 | 21 | 27 | 5.1 | 19 | 35 |
| 4 hours of inhalation | 5.4 | 54* | 44^ | 5.4 | 33** | 44 |

*Individual values were 33, 63, and 67 ng/mL
^Individual values were 34, 48, and 50 ng/mL
**Individual values were 22, 27, and 49 ng/mL When inhalation ended, treprostinil plasma concentrations declined gradually. Given the degree of individual variation, the estimated mean $T_{1/2}$ values were similar at all dose levels and ranged from 0.7 to 1.8 hours in males and 0.7 to 1.0 hours in females.

For Tre solution, with an administration at 0.785 mg/kg, plasma exposure to treprostinil was generally similar in both sexes.

The maximum mean treprostinil plasma concentration ($T_{max}$) was at the end of inhalation. Mean treprostinil plasma concentration was similar after 0.5, 1, or 4 hours of inhalation exposure to Tre solution, suggesting that steady state was achieved within the first 30 minutes of exposure. These data are summarized below.

| | Males | Females |
|---|---|---|
| 0.5 hours of inhalation | 17 | 12 |
| 1 hour of inhalation | 11 | 14 |
| 4 hours of inhalation | 16 | 16 |

When inhalation ended, treprostinil plasma concentrations declined gradually, with estimated mean $T_{1/2}$ values of 0.6 hours in males and 0.8 hours in females.

Administration of PRINT-Tre and Tre solution at nearly equivalent dose levels (0.76 and 0.79 mg/kg, respectively) resulted in plasma exposures to treprostinil that were greater with PRINT-Tre than with Tre solution. Specifically, mean $AUC_{0\text{-}Tlast}$ was approximately twice as high (126 versus 61 h*ng/mL, respectively) and mean $C_{max}$ was three times as high (44 versus 16 ng/mL, respectively). As would be expected, once treprostinil entered the systemic circulation, it was cleared from plasma at a similar rate, with mean $T_{1/2}$ values of 0.7 to 1.0 hours for PRINT-Tre and 0.6 to 0.8 hours for Tre solution.

Conclusion

Single inhalation administration for 4 hours of PRINT Treprostinil at a high average dose of 1.498 mg/kg/day to Sprague-Dawley rats was well tolerated as there were no test item related findings. At an equivalent dose level, plasma exposures to treprostinil was greater with PRINT-Tre than with Tre solution; specifically, mean $AUC_{0\text{-}Tlast}$ was approximately twice as great and mean $C_{max}$ was three times as great. As would be expected, once treprostinil entered the systemic circulation, it was cleared from plasma at a similar rate regardless of how it was administered.

Non-GLP, 7-Day, Repeat-Dose, Range-Finding (DRF), Inhalation Study with LIQ861 in Rats (Study 75654)

Results from the completed comparative PK study will be used to select dose levels to be tested in this DRF study, which will evaluate local toxicity in the respiratory tract as well as systemic treprostinil toxicity. Results will be used to select appropriate dose levels for a 2-week GLP repeat-dose toxicology study in rats.

Summary: Study 75654

The objectives of the study were to evaluate the toxicity of the test item, PRINT Treprostinil, and the excipients that make up the control item, PRINT Placebo, when administered to Sprague-Dawley rats by nose-only inhalation for 4 hours a day for 7 days. Results were used to help select dose levels for a subsequent 14-day GLP inhalation toxicology study.

Groups of 6 rats (3/sex) were exposed by 4-hour inhalation daily for 7 days to air, PRINT Placebo, or PRINT Treprostinil at treprostinil dose levels of approximately 170, 680, or 1370 µg/kg, as described in the table below:

| | | Mean Dose Levels and Concentrations[a] | | | | |
|---|---|---|---|---|---|---|
| | | Treprostinil | | Trehalose | | Leucine |
| Group No. | Group Designation | Dose Level (ug/kg/day) | Aerosol Conc. (µg/L) | Dose Level (mg/kg/day) | Aerosol Conc. (µg/L) | Dose Level (mg/kg/day)[b] |
| 1 | Air Control | 0 | 0 | 0 | 0 | 0 |
| 2 | Placebo Control[b] | 0 | 0 | 281.2 | 1832.13 | 12.0 |
| 3 | PRINT-Tre (Low Dose) | 170 | 1.10 | 33.1 | 216.30 | 1.3 |
| 4 | PRINT-Tre (Mid Dose) | 680 | 4.44 | 133.5 | 869.99 | 5.1 |
| 5 | PRINT-Tre (High Dose) | 1370 | 8.94 | 266.6 | 1735.84 | 10.3 |

[a]= Based on the mean body weight of each group during the dosing period.
[b]= Calculated with a content of 4% of Leucine in PRINT Treprostinil and PRINT Placebo and using Trehalose percentage of 93.5% in PRINT Placebo for Group 2 and Treprostinil percentage of 0.53% in PRINT Treprostinil for Groups 3 to 5.

The particle size MMADs from Groups 2 to 5 were between 1.3 and 2.0 µm gravimetrically (GSD 1.96 to 2.46); for both treprostinil and trehalose, chemical particle size distribution ranged from 1.3 to 2.1 µm with the corresponding GSDs between 1.87 and 1.95. No mortality occurred. No clinical signs were observed while coagulation, clinical chemistry and urinalysis parameters were unaffected and no test item-related findings were seen macroscopically.

Rats tolerated daily administration of PRINT Placebo or PRINT-Tre at up to 1.37 mg/kg/day by 4-hour inhalation for 7 days.

Introduction

The objectives of the study were to:
1. Evaluate the toxicity of the test item, PRINT Treprostinil, when administered to Sprague-Dawley rats by nose-only inhalation for 4 hours a day for 7 days.
2. Evaluate the toxicity of the excipients that make up the control item, PRINT Placebo, when administered to Sprague-Dawley rats by nose-only inhalation for 4 hours a day for 7 days.
3. Determine the dose levels of PRINT Treprostinil for the following 14-day GLP inhalation toxicology study from the results of this dose range-finding study.

Experimental Design

Synopsis

The test and control items were administered to groups of 6 rats (3/sex) by 4-hour inhalation daily for 7 days, as described in the table below. The first day of dosing was designated as Day 1.

| Group No. | Test Material | Targeted Aerosol Concentration (ug/L) | | Targeted Dose Level (mg/kg/day) | | Leucine Dose Level (mg/kg/day)[c] |
|---|---|---|---|---|---|---|
| | | Treprostinil | Trehalose | Treprostinil[a] | Trehalose[b] | |
| 1 | Air Control | 0 | 0 | 0 | 0 | 0 |
| 2 | PRINT Placebo[b] | 0 | 1684.6 | 0 | 262.9 | 11.2 |

-continued

| Group No. | Test Material | Targeted Aerosol Concentration (ug/L) Treprostinil | Targeted Aerosol Concentration (ug/L) Trehalose | Targeted Dose Level (mg/kg/day) Treprostinil[a] | Targeted Dose Level (mg/kg/day) Trehalose[b] | Leucine Dose Level (mg/kg/day)[c] |
|---|---|---|---|---|---|---|
| 3 | PRINT-Tre (Low Dose) | 1 | 175.2 | 0.15 | 26.3 | 1.1 |
| 4 | PRINT-Tre (Mid Dose) | 5 | 876.2 | 0.75 | 131.4 | 5.7 |
| 5 | PRINT-Tre (High Dose) | 10 | 1752.5 | 1.5 | 262.9 | 11.3 |

[a] = Target aerosol concentrations were calculated based on an estimated body weight of 0.250 kg
[b] = The target dose level for the placebo control was the same dose level as the high dose group (Group 5)
[c] = Calculated with a content of 4% of Leucine in PRINT Treprostinil and PRINT Placebo (using Trehalose percentage of 93.5% in PRINT Placebo for Group 2 and Treprostinil percentage of 0.53% in PRINT Treprostinil for Groups 3 to 5)

The high-dose level for PRINT-Tre was the feasible dose attainable based on technical aerosol trials with the test item. (Study No. 41610).

The low- and mid-dose levels for PRINT-Tre were selected on the basis of a previous PK study in rats (Study No. 75658).

Test and Control Item Information
Test Item Action
Treprostinil, the active ingredient in PRINT-Tre, is a prostacyclin compound approved for treatment of pulmonary arterial hypertension.
Characterization of Test Item
Content: 92.97% of Trehalose, 4% of Leucine, 2% of Tween80, 0.27% of Sodium Citrate Dihydrate, 0.23% of Sodium Chloride: 0.53% of Treprostinil sodium
Storage Conditions: Cool (2 to 8° C.), protected from moisture (e.g., desiccant)
Handling Precautions: Standard laboratory precautions. Handled under dry conditions (relative humidity ≤23%)
Supplier: Liquidia Technologies Inc.
Characterization of Placebo Control Item
Content: -LKI-1R-983-3: 93.53% of Trehalose, 4% of Leucine, 2% of Tween80, 0.24% of Sodium Citrate Dihydrate, 0.23% of Sodium Chloride
-LKI-1R-983-27: 93.5% of Trehalose, 4% of Leucine, 2% of Tween80, 0.27% of Sodium Citrate Dihydrate, 0.23% of Sodium Chloride
Storage Conditions: Cool (2 to 8° C.), protected from moisture (e.g., desiccant)
Handling Precautions: Standard laboratory precautions. Handled under dry conditions (relative humidity ≤23%)
Supplier: Liquidia Technologies Inc.
Characterization of Air Control
Description: Medical Grade Air (NQ 5710-500/2000)
Supplied By: Kaeser SM-11 Air Compressor
Preparation of Test and Control Items
PRINT-Tre and PRINT Placebo were used as provided by the Sponsor. A glove box under nitrogen was used for handling, aliquoting or packing of the canisters. Relative humidity (RH) inside the glove box was monitored and recorded using a hygrometer and was kept below 23% RH.
Treatment
Acclimatization to Exposure System
Before the rats were presented to exposure atmosphere, rats were accustomed to the restraint procedure over a period of 3 days. The animals were gradually accustomed to restraint in the dosing tubes used during the exposures up to the duration that was used for aerosol administrations.
Animal Exposure
Exposure system used: Flow-past rodent inhalation exposure system
Exposure method: Inhalation by nose-only exposure
Test and Control Item type: Air (Group 1), Dry Powder (Groups 2 to 5)
Generation method: Piston feed/rotating brush generator (Groups 2 to 5)
Duration of exposure: 240 minutes
The target aerosol concentrations and dose levels were as follows:

| Group No. | Group Designation | Targeted Total Inhaled Dose Level of Treprostinil (mg/kg/day)[a] | Targeted Aerosol Concentration of Treprostinil (μg/L) | Targeted Total Inhaled Dose Level of Trehalose (mg/kg/day)[a] | Targeted Aerosol Concentration of Trehalose (μg/L) | Estimated Total Inhaled Dose Level of Leucine (mg/kg/day)[c] |
|---|---|---|---|---|---|---|
| 1 | Air Control | 0 | 0 | 0 | 0 | 0 |
| 2 | Placebo Control[b] | 0 | 0 | 262.9 | 1684.6 | 11.2 |
| 3 | PRINT-Tre (Low Dose) | 0.15 | 1 | 26.3 | 175.2 | 1.1 |
| 4 | PRINT-Tre (Mid Dose) | 0.75 | 5 | 131.4 | 876.2 | 5.7 |
| 5 | PRINT-Tre (High Dose) | 1.5 | 10 | 262.9 | 1752.5 | 11.3 |

[a] = Target aerosol concentrations were calculated based on an estimated body weight of 0.250 kg
[b] = The target dose level for the placebo control was the dose level as the high dose group (Group 5)
[c] = Calculated with a content of 4% of Leucine in PRINT Treprostinil and PRINT Placebo (using Trehalose percentage of 93.5% in PRINT Placebo for Group 2 and Treprostinil percentage of 0.53% in PRINT Treprostinil for Groups 3 to 5)

Estimation of Achieved Dose Levels

The target dose levels were estimated using the following formula:

$$D_L = \frac{E_c \times RMV \times T}{BW}$$

$D_L$=Achieved dose levels (mg/kg/day)=
$E_c$=Actual concentration delivered to the animals (mg/L air)
RMV=Respiratory Minute Volume (L/min) according to the method of Bide, Armour and Yee. J. App. Toxicol., Vol. 20, 2000: RMV (L/min)=0.499×BW $(kg)^{00.809}$
T=Time, duration of daily exposure (min.)
BW=Mean body weight (kg) during exposure period.
This estimation of total inhaled dose assumed 100% deposition within the respiratory tract.

Inhalation Exposure System

The powder aerosol for Groups 2 to 5 was produced using a piston feed/rotating brush generator. The aerosol produced was diluted as necessary to achieve the target aerosol concentration and discharged through a 40-mm diameter tube into a flow-past inhalation exposure system. The airflow rate through the exposure system was monitored and recorded manually during each aerosol generation period. Airflow to the exposure system was controlled by the absolute volume of air supplying the generation apparatus using variable area flowmeters. Control of the aerosol exhaust flow from the animal exposure system was achieved using an exhaust valve, and the overall balance of airflows in the exposure system was monitored using pressure gauges. The system provided a minimum of 1.0 L/min to each animal exposure port and was balanced to ensure a slight positive pressure at the site of the animal exposure. This ensured that there was no dilution of the generated aerosol. An equal delivery of aerosol to each exposure position was achieved by employing a distribution network that was identical for each individual exposure position attached to the system.

Inhalation System Monitoring

Determinations of aerosol concentration, particle size distribution, oxygen concentration, relative humidity and temperature were measured on samples collected from a representative port of the exposure chamber, with a collection sample flow-rate of 1 L/min. The sample flow rates were precisely controlled using variable area flow meters that were calibrated before use using a primary airflow calibrator. The absolute volume of each aerosol concentration sample was measured with a wet type gas meter.

Oxygen Concentration

The oxygen concentration of the generated atmosphere was measured once during each aerosol exposure. Oxygen concentrations of the exposure atmospheres were maintained between 19-23%.

Relative Humidity/Temperature

The temperature and relative humidity of the generated atmosphere were measured once during each aerosol exposure. Temperatures of the exposure atmospheres were maintained between 19-24° C.

Determination of Aerosol Concentration

At least one aerosol concentration filter sample was collected for all groups on each aerosol generation. The filter samples from Groups 3 to 5 were weighed in order to measure the gravimetric concentration of the test item in the generated aerosol. The filter samples were transferred to the analytical chemistry laboratory for chemical determination of Treprostinil and Trehalose concentrations. The filter samples from Group 2 were weighed in order to measure the gravimetric concentration of the control item in the generated aerosol. The filter samples were transferred to the analytical chemistry laboratory for chemical determination of Trehalose concentration and to confirm the absence of Treprostinil. The filter samples for Group 1 were not weighed gravimetrically and were only transferred to the analytical laboratory to confirm the absence of Treprostinil and Trehalose. The analysis in the analytical laboratory was performed using an analytical method (Study No. 41609 and 41635).

Determination of Aerosol Homogeneity

At least once during the study, atmosphere homogeneity in the exposure system was tested by collecting multiple aerosol samples from the top, middle and bottom tiers of the exposure system of Groups 2 to 5.

Determination of the Particle Size Distribution and Mass Median Aerodynamic Diameter (MMAD)

The distribution of particle size in the generated aerosols was measured at least once for Groups 2 to 5 by collecting samples into a 7-Stage Mercer Cascade Impactor. All sample substrates obtained from Groups 3 to 5 were weighed gravimetrically and then transferred to the analytical chemistry laboratory for chemical determination of particle size of aerosolized Treprostinil and Trehalose. All sample substrates obtained from Group 2 were weighed gravimetrically and then transferred to the analytical laboratory for determination of particle size of aerosolized Trehalose. The analysis in the analytical laboratory was performed using an analytical method (Study No. 41609 and 41635).

The MMAD and the Geometric Standard Deviation (GSD) were calculated based on the results obtained from the impactor using a log-probit transformation.

Reporting of Analytical Results

The analytical report containing the results from the filter and particle size distribution sample analyses were prepared. Any samples not employed in the primary analysis or any remaining sample from the primary analysis were retained until it was determined by the analyst and Study Director that it was not required for confirmatory analysis. These samples were then discarded and their disposition was recorded in the raw data.

Standard Operating Procedures

All procedures, were performed in accordance with the Standard Operating Procedures and these were kept on file. Deviations to the Standard Operating Procedures were documented in the raw data.

Results

Inhalation System Monitoring

Oxygen Concentration, Temperature, and Relative Humidity

Exposure chamber conditions from the reported aerosol concentration exposures are summarized below.

| Group Number | Humidity (% RH) Average | Temperature (° C.) Average | Oxygen Concentration (%) Average |
|---|---|---|---|
| 1 | 28.6 | 20.4 | 20.9 |
| 2 | 39.6 | 21.2 | 20.9 |
| 3 | 35.6 | 21.6 | 20.9 |
| 4 | 26.2 | 21.1 | 20.9 |
| 5 | 31.1 | 20.8 | 20.9 |

Exposure atmosphere oxygen concentration, temperature and relative humidity were considered acceptable throughout the study.

Aerosol Concentrations

Achieved gravimetric test atmosphere concentrations were as follows:

| Group No. | Targeted Aerosol Concentration (mg\L) | Achieved Mean Aerosol Concentration (mg\L) | Coefficient of Variation (%) | % of Target |
|---|---|---|---|---|
| 2 | 2.000* | 1.966 | 34.7 | 98.3 |
| 3 | 0.200* | 0.231 | 21.4 | 115.5 |
| 4 | 1.000* | 0.928 | 20.5 | 92.8 |
| 5 | 2.000* | 1.848 | 26.0 | 92.4 |

*Target aerosol concentrations were 0.140 mg/L for Group 3, 0.700 mg/L for Group 4 and 1.400 mg/L for Groups 2 and 5 for the first 2 days of exposure.

Achieved test atmosphere concentrations for treprostinil were as follows:

| Group No. | Targeted Aerosol Concentration (µg\L) | Achieved Mean Aerosol Concentration (µg\L) | Coefficient of Variation (%) | % of Target |
|---|---|---|---|---|
| 3 | 1.0 | 1.10 | 22.1 | 110.0 |
| 4 | 5.0 | 4.44 | 21.0 | 88.8 |
| 5 | 10.0 | 8.94 | 28.1 | 89.4 |

Achieved test atmosphere concentrations for trehalose were as follows:

| Group No. | Targeted Aerosol Concentration (µg\L) | Achieved Mean Aerosol Concentration (µg\L) | Coefficient of Variation (%) | % of Target |
|---|---|---|---|---|
| 2 | 1684.6 | 1832.13 | 36.4 | 108.8 |
| 3 | 175.2 | 216.30 | 22.1 | 123.5 |
| 4 | 876.2 | 869.99 | 21.2 | 99.3 |
| 5 | 1752.5 | 1735.84 | 29.4 | 99.0 |

The overall achieved aerosol concentrations for all groups were within 20% of the targeted concentrations gravimetrically and for both treprostinil and trehalose, except for Group 3 for trehalose which was 23.5% greater than the targeted concentration. The generated atmospheres were considered stable over the treatment period even if all % CV were all above 20% as this was due the wrong targeted gravimetric concentrations being applied for the first 2 days of dosing. The overall aerosol concentrations were still considered acceptable for the study as there was a significant difference in aerosol concentration between groups.

Aerosol Homogeneity

Achieved gravimetric test atmosphere homogeneity concentrations were as follows:

| Group No. | Aerosol Concentration of Top Tier (mg/L) | Aerosol Concentration of Middle Tier (mg/L) | Aerosol Concentration of Bottom Tier (mg/L) | CV (%) |
|---|---|---|---|---|
| 2 | 1.061 | 1.029 | 1.078 | 2.4 |
| 3 | 0.134 | 0.136 | 0.126 | 4.0 |
| 4 | 0.810 | 0.877 | 0.845 | 4.0 |
| 5 | 1.225 | 1.263 | 1.280 | 2.2 |

Achieved test atmosphere homogeneity concentrations for treprostinil were as follows:

| Group No. | Aerosol Concentration of Top Tier (µg/L) | Aerosol Concentration of Middle Tier (µg/L) | Aerosol Concentration of Bottom Tier (µg/L) | CV (%) |
|---|---|---|---|---|
| 3 | 0.63 | 0.64 | 0.59 | 4.3 |
| 4 | 3.90 | 4.16 | 4.04 | 3.2 |
| 5 | 5.73 | 6.03 | 6.12 | 3.4 |

Achieved test atmosphere homogeneity concentrations for trehalose were as follows:

| Group No. | Aerosol Concentration of Top Tier (µg/L) | Aerosol Concentration of Middle Tier (µg/L) | Aerosol Concentration of Bottom Tier (µg/L) | CV (%) |
|---|---|---|---|---|
| 2 | 916.21 | 888.61 | 919.90 | 1.9 |
| 3 | 113.82 | 111.38 | 102.88 | 5.3 |
| 4 | 774.67 | 887.67 | 780.97 | 7.8 |
| 5 | 1091.32 | 1153.45 | 1160.14 | 3.3 |

Chamber homogeneity of the aerosol concentrations were considered acceptable since the coefficient of variance of aerosol concentration between samples was not greater than 20%.

Particle Size Distribution

The average gravimetric particle size distribution measurement data were as follows:

| Group No. | Cumulative % Less Than Stated Effective Cut-Off Diameter (µm) | | | | | | | | Mean MMAD (µm) | GSD | % below 4 µm |
|---|---|---|---|---|---|---|---|---|---|---|---|
| | 4.60 | 3.00 | 2.10 | 1.60 | 1.10 | 0.70 | 0.33 | 0.00 | | | |
| 2 | 89.1 | 81.8 | 51.3 | 19.3 | 11.6 | 9.4 | 7.9 | 0.0 | 2.0 | 2.46 | 78 |
| 3 | 97.9 | 95.0 | 79.6 | 35.5 | 21.1 | 15.1 | 5.7 | 0.0 | 1.3 | 1.96 | 94 |
| 4 | 95.5 | 89.4 | 60.3 | 24.1 | 13.4 | 9.0 | 4.8 | 0.0 | 1.7 | 2.07 | 88 |
| 5 | 96.9 | 92.3 | 63.1 | 28.2 | 15.7 | 8.5 | 4.8 | 0.0 | 1.6 | 1.99 | 91 |

MMAD = Mass median aerodynamic diameter

GSD = Geometric standard deviation.

The chemical determinations of particle size distribution for treprostinil were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
| | 4.60 | 3.00 | 2.10 | 1.60 | 1.10 | 0.70 | 0.33 | 0.00 | | | |
| 3 | 98.8 | 95.7 | 80.3 | 35.2 | 20.2 | 14.2 | 5.0 | 0.0 | 1.3 | 1.88 | 96 |
| 4 | 96.3 | 90.1 | 59.9 | 22.2 | 11.1 | 6.9 | 2.9 | 0.0 | 1.7 | 1.95 | 89 |
| 5 | 97.2 | 92.8 | 63.3 | 26.7 | 13.6 | 6.4 | 2.8 | 0.0 | 1.6 | 1.89 | 92 |

MMAD = Mass median aerodynamic diameter
GSD = Geometric standard deviation.

The chemical determinations of particle size distribution for trehalose were as follows:

| Group No. | Cumulative % Less Than Stated Effective Cut-Off Diameter (μm) | | | | | | | | Mean MMAD (μm) | GSD | % below 4 μm |
|---|---|---|---|---|---|---|---|---|---|---|---|
| | 4.60 | 3.00 | 2.10 | 1.60 | 1.10 | 0.70 | 0.33 | 0.00 | | | |
| 2 | 89.3 | 85.2 | 52.1 | 17.7 | 8.1 | 4.0 | 0.0 | 0.0 | 2.1 | 1.74 | 87 |
| 3 | 96.6 | 93.3 | 77.4 | 31.0 | 15.4 | 12.0 | 3.4 | 0.0 | 1.5 | 1.94 | 93 |
| 4 | 97.3 | 90.9 | 59.3 | 19.9 | 8.0 | 5.3 | 2.7 | 0.0 | 1.8 | 1.88 | 90 |
| 5 | 97.2 | 94.4 | 62.6 | 25.0 | 12.1 | 5.6 | 2.8 | 0.0 | 1.6 | 1.87 | 92 |

MMAD = Mass median aerodynamic diameter
GSD = Geometric standard deviation.

The particle size distribution was considered respirable for this study as all MMADs were below 4 μm and the GSDs were within 1.5 and 3.

Estimation of Achieved Dose Levels

Overall achieved doses for treprostinil are presented below:

| Group No. | Targeted Dose Level (mg/kg/day) | Duration of Exposure (min) | Sex | Body Weight (kg) | Estimated Achieved Doses (mg/kg/day) | % of Targeted Dose Level |
|---|---|---|---|---|---|---|
| 3 | 0.15 | 240 | Male | 0.324 | 0.16 | 106.7 |
| | | | Female | 0.227 | 0.17 | 113.3 |
| | | | Combined | 0.276 | 0.17 | 113.3 |
| 4 | 0.75 | 240 | Male | 0.316 | 0.66 | 88.0 |
| | | | Female | 0.229 | 0.70 | 93.3 |
| | | | Combined | 0.273 | 0.68 | 90.7 |
| 5 | 1.5 | 240 | Male | 0.315 | 1.33 | 88.7 |
| | | | Female | 0.228 | 1.42 | 94.7 |
| | | | Combined | 0.272 | 1.37 | 91.3 |

Overall achieved doses for trehalose are presented below:

| Group No. | Targeted Dose Level (mg/kg/day) | Duration of Exposure (min) | Sex | Body Weight (kg) | Estimated Achieved Doses (mg/kg/day) | % of Targeted Dose Level |
|---|---|---|---|---|---|---|
| 2 | 262.9 | 240 | Male | 0.316 | 273.4 | 104.0 |
| | | | Female | 0.229 | 290.8 | 110.6 |
| | | | Combined | 0.273 | 281.2 | 107.0 |
| 3 | 26.3 | 240 | Male | 0.324 | 32.1 | 122.1 |
| | | | Female | 0.227 | 34.4 | 130.8 |
| | | | Combined | 0.276 | 33.1 | 125.9 |
| 4 | 131.4 | 240 | Male | 0.316 | 129.8 | 98.8 |
| | | | Female | 0.229 | 138.1 | 105.1 |
| | | | Combined | 0.273 | 133.5 | 101.6 |
| 5 | 262.9 | 240 | Male | 0.315 | 259.2 | 98.6 |
| | | | Female | 0.228 | 275.7 | 104.9 |
| | | | Combined | 0.272 | 266.6 | 101.4 |

Overall achieved doses for leucine are presented below:

| Group No. | Targeted Dose Level (mg/kg/day) | Duration of Exposure (min) | Sex | Body Weight (kg) | Estimated Achieved Doses[a] (mg/kg/day) | % of Targeted Dose Level |
|---|---|---|---|---|---|---|
| 2 | 11.2 | 240 | Male | 0.316 | 11.7 | 104.5 |
|   |      |     | Female | 0.229 | 12.4 | 110.7 |
|   |      |     | Combined | 0.273 | 12.0 | 107.1 |
| 3 | 1.1 | 240 | Male | 0.324 | 1.2 | 109.1 |
|   |     |     | Female | 0.227 | 1.3 | 118.2 |
|   |     |     | Combined | 0.276 | 1.3 | 118.2 |
| 4 | 5.7 | 240 | Male | 0.316 | 5.0 | 87.7 |
|   |     |     | Female | 0.229 | 5.3 | 93.0 |
|   |     |     | Combined | 0.273 | 5.1 | 89.5 |
| 5 | 11.3 | 240 | Male | 0.315 | 10.0 | 88.5 |
|   |      |     | Female | 0.228 | 10.7 | 94.7 |
|   |      |     | Combined | 0.272 | 10.3 | 91.2 |

[a]Calculated with a content of 4% of Leucine in PRINT-Tre and PRINT Placebo (using Trehalose percentage of 93.5% in PRINT Placebo for Group 2 and Treprostinil percentage of 0.53% in PRINT-Tre for Groups 3 to 5)

Average achieved dose levels for all groups were within 20% of the targeted dose levels, except for Group 3 for trehalose which was 26% above the targeted dose level; however, the dose levels were considered acceptable for the study as a clear dose differentiation between groups for each sex was achieved.

Mortality

There were no mortalities during the study.

Clinical Signs

There were no clinical signs observed during the study.

Body Weight

The only differences in body weight or weight gain potentially related to administration of the test or control item were slightly less growth (weight gain) in males given PRINT-Tre at 0.68 mg/kg/day and in both sexes given to PRINT-Tre at 1.37 mg/kg/day, relative to the air control group. The pattern of differences implicates the active ingredient treprostinil, not one of the excipients in PRINT-Tre.

These data are summarized in the table below, with differences potentially related to treprostinil in bold.

| | Test Material = | | | | |
|---|---|---|---|---|---|
| | Air | PRINT Placebo | PRINT-Tre | | |
| | Treprostinial Dose Level (mg/kg/day) = | | | | |
| | 0 | 0 | 0.17 | 0.68 | 1.37 |
| | Trehalose Dose Level (mg/kg/day) = | | | | |
| | 0 | 281 | 33 | 134 | 267 |
| Males | | | | | |
| Starting weight (Day 1) (g) | 301 | 309 | 315 | 312 | 312 |
| After 4 doses (Day 5) (g) | 324 | 326 | 337 | 324 | 322 |
| Change | | | | | |
| Absolute (g) | +23 | +17 | +22 | +12 | +10 |
| Relative to Air Control | — | −6 | −1 | −11 | −13 |
| After 7 doses (fasted Day 8) (g) | 300 | 302 | 310 | 301 | 298 |
| Change | | | | | |
| Absolute (g)* | −1 | −7 | −5 | −10 | −14 |
| Relative to Air Control | — | −6 | −4 | −9 | −13 |
| Females | | | | | |
| Starting weight (Day 1) (g) | 220 | 223 | 220 | 227 | 226 |
| After 4 doses (Day 5) (g) | 231 | 235 | 232 | 237 | 231 |
| Change | | | | | |
| Absolute (g) | +11 | +12 | +12 | +10 | +5 |
| Relative to Air Control | — | +1 | +1 | −1 | −6 |
| After 7 doses (fasted Day 8) (g) | 205 | 209 | 204 | 213 | 211 |
| Change | | | | | |
| Absolute (g)* | −15 | −14 | −16 | −14 | −15 |
| Relative to Air Control | — | +1 | −1 | −1 | 0 |

*All animals were fasted overnight prior to necropsy.

Remaining differences were considered incidental and of no biological significance.

Hematology

The only differences in mean hematology parameters potentially related to administration of the test or control item were greater mean reticulocyte counts in all groups given PRINT-Tre, relative to the air control group. The magnitude of difference was dose-related but statistically significant only in males. The pattern of differences implicates the active ingredient treprostinil, not one of the excipients in PRINT-Tre.

These data are summarized in the table below, with differences potentially related to treprostinil in bold.

| | Test Material = | | | | |
|---|---|---|---|---|---|
| | Air | PRINT Placebo | PRINT-Tre | | |
| | Treprostinial Dose Level (mg/kg/day) = | | | | |
| | 0 | 0 | 0.17 | 0.68 | 1.37 |
| | Trehalose Dose Level (mg/kg/day) = | | | | |
| Reticulocyte count | 0 | 281 | 33 | 134 | 267 |
| Males | | | | | |
| Mean (×10$^{12}$/L) | 0.226 | 0.228 | 0.309 | 0.333 | 0.337 |
| Relative to Air Control | — | +1% | +37% | +47% | +49% |

-continued

| | Test Material = | | | | |
|---|---|---|---|---|---|
| | Air | PRINT Placebo | PRINT-Tre | | |
| | Treprostinial Dose Level (mg/kg/day) = | | | | |
| | 0 | 0 | 0.17 | 0.68 | 1.37 |
| | Trehalose Dose Level (mg/kg/day) = | | | | |
| Reticulocyte count | 0 | 281 | 33 | 134 | 267 |
| Females | | | | | |
| Mean (×10$^{12}$/L) | 0.179 | 0.176 | 0.214 | 0.290 | 0.283 |
| Relative to Air Control | — | +1% | +20% | +62% | +58% |

An increase in reticulocyte count is an appropriate response to an increased demand for RBCs. In this study, greater reticulocyte counts were not associated with differences in circulating erythron mass (i.e., no differences in RBC count, haemoglobin concentration, or haematocrit). This suggests that the increased release of reticulocytes was accompanied by, and probably a response to, an increased rate of RBC loss, and that the erythropoietic response was adequate to maintain normal circulating RBC numbers.

Remaining differences among mean hematology parameters were considered incidental and of no biological significance.

Coagulation

There were no differences in mean coagulation parameters that were considered to be related to administration of the test or control item. All differences were considered incidental and of no biological significance.

Clinical Chemistry

There were no differences in mean clinical chemistry parameters that were considered to be related to administration of the test or control item. All differences were considered incidental and of no biological significance.

Urinalysis

There were no differences in the urinalysis parameters that were considered to be related to administration of the test or control item. All differences were considered incidental and of no biological significance.

Organ Weights

Differences in mean organ weight potentially related to administration of the test or control item were noted for lungs, adrenal glands, thymus, and testes.

Remaining differences in mean organ weight were considered incidental and of no biological significance.

Lungs

Mean lungs/trachea weights (absolute and relative to body weight) were greater in all groups given the test or control item, compared to the air control group. The differences were greater with PRINT-Tre than with PRINT Placebo, and the differences were dose-related for PRINT-Tre. This pattern suggests that administration of the excipients (likely trehalose) resulted in a slight (15% to 17%) increase in lung weight, which was exacerbated by co-administration of treprostinil as the lung weights of PRINT-Tre groups were increased compared to the lung weights of the PRINT Placebo group.

There was a histopathologic finding in the lungs that might have accounted for the greater lung weight; specifically, increased alveolar macrophages with basophilic vacuolated cytoplasm in the lungs of all rats given PRINT Placebo or PRINT-Tre at ≥0.68 mg/kg/day. However, neither the distribution of this histopathologic finding across groups nor the grade of the finding correlated well with the differences in mean lung weight, suggesting that some other factor was responsible. Because lungs were weighed before fixation, it is possible that some material responsible for the greater weight was removed during tissue fixation and processing.

Lung weight data are summarized in the table below, with differences potentially related to PRINT Placebo and PRINT-Tre in bold.

Mean Lung Weight Data

| | Test Material = | | | | |
|---|---|---|---|---|---|
| | Air | PRINT Placebo | PRINT-Tre | | |
| | Treprostinial Dose Level (mg/kg/day) = | | | | |
| | 0 | 0 | 0.17 | 0.68 | 1.37 |
| | Trehalose Dose Level (mg/kg/day) = | | | | |
| | 0 | 281 | 33 | 134 | 267 |
| Males | | | | | |
| Absolute weight (g) | 1.39 | 1.60 | 1.70 | 1.78* | 1.90* |
| Relative to Air Control | — | +15% | +22% | +28% | +37% |
| Relative weight (% body weight) | 0.46 | 0.53 | 0.55 | 0.59* | 0.64* |
| Relative to Air Control | — | +15% | +20% | +28% | +39% |
| Females | | | | | |
| Absolute weight (g) | 1.09 | 1.27 | 1.31* | 1.48* | 1.44* |
| Relative to Air Control | — | +17% | +20% | +36% | +32% |
| Relative weight (% body weight) | 0.53 | 0.61 | 0.64 | 0.70* | 0.68* |
| Relative to Air Control | — | +15% | +21% | +32% | +28% |

*Statistically significant compared to air control; Dunnett's 2-sided, $p < 0.05$ Thymus Mean thymus weights (absolute and relative to body weight) were slightly lower in both sexes given PRINT-Tre at 0.68 mg/kg/day and in both sexes given to PRINT-Tre at 1.37 mg/kg/day, relative to the air control group (though not statistically significantly different). The pattern of differences implicates the active ingredient treprostinil, not one of the excipients in PRINT-Tre as differences were also seen between PRINT-Tre groups and PRINT Placebo group. Lower thymus weight was not associated with lower lymphocyte count or with any histopathologic findings.

Lower thymus weight is one common manifestation of nonspecific physiological or psychological stress (Everds et al., 2013). Because this finding was associated with reduced weight gain (growth) and sometimes also with greater adrenal glands weight, it was most likely secondary to stress and not a direct effect of treprostinil.

Thymus weight data are summarized in the table below, with differences potentially related to treprostinil in bold.

Mean Thymus Weight Data

|  | Test Material = | | | | |
| --- | --- | --- | --- | --- | --- |
|  | Air | PRINT Placebo | PRINT-Tre | | |
|  | Treprostinial Dose Level (mg/kg/day) = | | | | |
|  | 0 | 0 | 0.17 | 0.68 | 1.37 |
|  | Trehalose Dose Level (mg/kg/day) = | | | | |
|  | 0 | 281 | 33 | 134 | 267 |
| Males | | | | | |
| Absolute weight (mg) | 504 | 593 | 537 | 388 | 429 |
| Relative to Air Control | — | +18% | +7% | −23% | −15% |
| Relative weight (% body weight) | 0.168 | 0.198 | 0.173 | 0.128 | 0.143 |
| Relative to Air Control | — | +18% | +3% | −24% | −15% |
| Females | | | | | |
| Absolute weight (mg) | 469 | 437 | 465 | 428 | 352 |
| Relative to Air Control | — | −7% | −1% | −9% | −25% |
| Relative weight (% body weight) | 0.229 | 0.210 | 0.228 | 0.202 | 0.166 |
| Relative to Air Control | — | −8% | ±0% | −12% | −28% |

Adrenal Glands

Mean adrenal glands weight (absolute and relative to body weight) was greater in males given PRINT-Tre at 0.17 mg/kg/day and in both sexes given to PRINT-Tre at 1.37 mg/kg/day, relative to the air control group (though not statistically significantly different). While the differences may have been due to chance and a consequence of the small group sizes (3/sex), the pattern of differences raises the possibility that they are related to administration of treprostinil, at least at the high-dose level as differences were also seen between the high dose PRINT-Tre group and the PRINT Placebo group. Greater adrenal glands weight was not associated with any histopathologic findings.

Greater adrenal glands weight is one common manifestation of nonspecific physiological or psychological stress (Everds et al., 2013). Because this finding was associated with reduced weight gain (growth) and lower thymus weight at the high-dose level, it was most likely secondary to stress and not a direct effect of treprostinil.

Adrenal glands weight data are summarized in the table below, with differences potentially related to treprostinil in bold.

Mean Adrenal Glands Weight Data

|  | Test Material = | | | | |
| --- | --- | --- | --- | --- | --- |
|  | Air | PRINT Placebo | PRINT-Tre | | |
|  | Treprostinial Dose Level (mg/kg/day) = | | | | |
|  | 0 | 0 | 0.17 | 0.68 | 1.37 |
|  | Trehalose Dose Level (mg/kg/day) = | | | | |
|  | 0 | 281 | 33 | 134 | 267 |
| Males | | | | | |
| Absolute weight (mg) | 62 | 71 | 76 | 68 | 78 |
| Relative to Air Control | — | +15% | +23% | +10% | +26% |
| Relative weight (% body weight) | 0.021 | 0.023 | 0.025 | 0.023 | 0.027 |
| Relative to Air Control | — | +10% | +19% | +10% | +29% |
| Females | | | | | |
| Absolute weight (mg) | 74 | 73 | 70 | 76 | 89 |
| Relative to Air Control | — | −1% | −5% | +3% | +20% |
| Relative weight (% body weight) | 0.036 | 0.035 | 0.035 | 0.036 | 0.042 |
| Relative to Air Control | — | −3% | −3% | ±0% | +17% |

Testes

There was a trend toward slightly lower mean testes weight (absolute and relative to body weight) in groups given PRINT-Tre at ≥0.68 mg/kg/day, relative to the air control group. While the differences may have been due to chance and a consequence of the small group sizes (3/sex), the pattern of differences raises the possibility that they are related to administration of treprostinil as differences were also seen between the mid and high dose PRINT-Tre groups and the PRINT Placebo group. Slightly lower testes weight was not associated with any histopathologic findings.

Testes weight data are summarized in the table below, with differences potentially related to treprostinil in bold.

Mean Testes Weight Data

|  | Test Material = | | | | |
| --- | --- | --- | --- | --- | --- |
|  | Air | PRINT Placebo | PRINT-Tre | | |
|  | Treprostinial Dose Level (mg/kg/day) = | | | | |
|  | 0 | 0 | 0.17 | 0.68 | 1.37 |
|  | Trehalose Dose Level (mg/kg/day) = | | | | |
|  | 0 | 281 | 33 | 134 | 267 |
| Absolute weight (g) | 3.51 | 3.40 | 3.39 | 3.25 | 3.15 |
| Relative to Air Control | — | −3% | −3% | −7% | −10% |
| Relative weight (% body weight) | 1.17 | 1.13 | 1.10 | 1.08 | 1.06 |
| Relative to Air Control | — | −3% | −6% | −8% | −9% |

Macroscopic Findings

There was no evidence of test item-related macroscopic findings at necropsy.

All findings were considered to be incidental as they were not dose-related, of low incidence, or occurred in the air control, placebo control and treated animals.

Microscopic Findings

Treatment-related findings were observed in the lungs, anterior nasal cavity, and nasopharynx. All other microscopic findings were considered to be incidental or procedure-related.

Lungs

In the lungs, minimal to mild increased alveolar macrophages with basophilic vacuolated cytoplasm were observed in all rats given PRINT Placebo or PRINT-Tre at ≥0.68 mg/kg/day. The pattern of this finding across groups indicates that it is a response to the excipients (likely trehalose). There were no associated inflammatory changes in the lungs. Increased alveolar macrophages are a common finding in inhalation toxicity studies with powders. It reflects normal pulmonary clearance of inhaled particles and is not considered to be adverse.

These data are summarized in the table below, with differences potentially related to test or control item in bold.

Incidence and Grade of Increased Alveolar Macrophages

| | Test Material = | | | | |
|---|---|---|---|---|---|
| | Air | PRINT Placebo | PRINT-Tre | | |
| | Treprostinial Dose Level (mg/kg/day) = | | | | |
| | 0 | 0 | 0.17 | 0.68 | 1.37 |
| | Trehalose Dose Level (mg/kg/day) = | | | | |
| | 0 | 281 | 33 | 134 | 267 |
| Males | | | | | |
| Incidence | 0/3 | 3/3 | 0/3 | 3/3 | 3/3 |
| Mean grade | — | 1.7 | — | 1.0 | 1.7 |
| Females | | | | | |
| Incidence | 0/3 | 3/3 | 0/3 | 3/3 | 3/3 |
| Mean grade | — | 2.0 | — | 1.0 | 1.7 |

Nasal Cavity and Nasopharynx

Goblet-cell hypertrophy/hyperplasia was seen in the cranial portion of the nasal cavity and in the nasopharynx of at least one rat in all groups given PRINT Placebo or PRINT-Tre, but the incidence was greater in groups given PRINT-Tre at ≥0.68 mg/kg/day, and the mean grade was greater in the group given PRINT-Tre at 1.37 mg/kg/day. This pattern suggests that administration of the excipients (likely trehalose) resulted in occasional goblet-cell changes, which were exacerbated by co-administration of treprostinil at higher dose levels.

Goblet cell hypertrophy/hyperplasia in the anterior nasal cavity and nasopharynx is one of the most frequently observed lesions in rodents exposed to irritant compounds. This finding generally is considered a nonspecific protective or adaptive response and not adverse.

These data are summarized in the table below, with differences potentially related to test or control item in bold.

Incidence and Grade of Goblet-Cell Hypertrophy/Hyperplasia

| | Test Material = | | | | |
|---|---|---|---|---|---|
| | Air | PRINT Placebo | PRINT-Tre | | |
| | Treprostinial Dose Level (mg/kg/day) = | | | | |
| | 0 | 0 | 0.17 | 0.68 | 1.37 |
| | Trehalose Dose Level (mg/kg/day) = | | | | |
| | 0 | 281 | 33 | 134 | 267 |
| Nasal Cavity | | | | | |
| Males | | | | | |
| Incidence | 0/3 | 1/3 | 1/3 | 3/3 | 3/3 |
| Mean grade | — | 1.0 | 1.0 | 1.0 | 1.3 |

*-continued*

| | Test Material = | | | | |
|---|---|---|---|---|---|
| | Air | PRINT Placebo | PRINT-Tre | | |
| | Treprostinial Dose Level (mg/kg/day) = | | | | |
| | 0 | 0 | 0.17 | 0.68 | 1.37 |
| | Trehalose Dose Level (mg/kg/day) = | | | | |
| | 0 | 281 | 33 | 134 | 267 |
| Females | | | | | |
| Incidence | 0/3 | 0/3 | 0/3 | 1/3 | 2/3 |
| Mean grade | — | — | — | 1.0 | 1.5 |
| Nasopharynx | | | | | |
| Males | | | | | |
| Incidence (all graded minimal) | 0/3 | 0/3 | 0/3 | 3/3 | 3/3 |
| Females | | | | | |
| Incidence(all graded minimal) | 0/3 | 1/3 | 0/3 | 3/3 | 3/3 |

Discussion and Conclusions

Rats tolerated daily administration of PRINT Placebo or PRINT-Tre at up to 1.37 mg/kg/day by 4-hour inhalation for 7 days.

The only findings potentially related to administration of excipients (likely trehalose) were:

Increased alveolar macrophages with basophilic vacuolated cytoplasm in all rats given PRINT Placebo or PRINT-Tre at ≥0.68 mg/kg/day; i.e., in rats given trehalose at ≥134 mg/kg/day. The mean grade of this finding increased with trehalose dose level. This finding was not associated with inflammatory changes in the lungs and was considered to reflect normal pulmonary clearance of inhaled particles. It was not considered to be adverse.

Greater mean lung weight in groups given PRINT Placebo or PRINT-Tre. The weight differences were unrelated to trehalose dose level. Instead, they were greater with PRINT-Tre than with PRINT Placebo and were dose-related for PRINT-Tre. This pattern suggests that administration of the excipients (likely trehalose) resulted in a slight (15% to 17%) increase in lung weight, which was exacerbated by co-administration of treprostinil. Of note, the pattern of differences in lung weight across groups is distinct from the pattern of increased alveolar macrophages across groups, indicating that the weight differences were not a consequence of increased macrophages. There were no histopathologic findings in the lungs that might have accounted for the greater lung weight. Because lungs were weighed before fixation, it is possible that some material responsible for the greater weight was removed during tissue fixation and processing.

Minimal goblet-cell hypertrophy/hyperplasia in the cranial portion of the nasal cavity of at least one rat in all groups given PRINT Placebo or PRINT-Tre. The incidence of this finding was unrelated to trehalose dose level. Instead, the incidence was greater with PRINT-Tre at ≥0.68 mg/kg/day, and the mean grade was greater with PRINT-Tre at 1.37 mg/kg/day. This pattern suggests that administration of the excipients (likely trehalose) resulted in occasional goblet-cell changes, which were exacerbated by co-administration of treprostinil at higher dose levels. Goblet-cell hypertrophy/hyperplasia was considered a nonspecific protective or adaptive response and not adverse.

Besides exacerbating lung weight differences and goblet-cell hypertrophy/hyperplasia in the nasal cavity and nasopharynx, the following other findings were potentially related to administration of treprostinil as PRINT-Tre:

Slightly less growth (weight gain) in males at 0.68 mg/kg/day and in both sexes at 1.37 mg/kg/day.

Greater mean reticulocyte counts at all dose levels, with the magnitude of difference increasing with dose level. This was not considered adverse in and of itself; however, it likely reflected an appropriate adaptive response to an increased rate of RBC loss or turnover.

Greater mean adrenal glands weight in males at 0.17 mg/kg/day, lower mean thymus weight in both sexes at 0.68 mg/kg/day, and greater mean adrenal glands weight and lower mean thymus weight in both sexes at 1.37 mg/kg/day. There were no associated differences in lymphocyte count or histopathologic findings in either organ. These organ weight differences most likely reflected stress and were not a direct effect of treprostinil.

Based on these results, it is recommended that an upcoming 14-day GLP inhalation toxicology study in rats target similar dose levels as used in the current study.

Clinical Study: LIQ861

Randomized, Placebo-Controlled, Single-Ascending Dose Study Evaluating Pharmacokinetics (PK) and Safety in Healthy Male and Female Volunteers A clinical study was conducted to (1) determine the single-dose safety and tolerability and (2) evaluate the single-dose pharmacokinetics of particles of the invention upon administration to healthy male and female subjects.

Six cohorts were evaluated: dose levels of 25, 50, 75, 100, 125 and 150 μg of treprostinil respectively. In each cohort, eight subjects were randomly assigned in a 3:1 blinded ratio and received a single dose of either particles of the invention (N=6) or placebo particles (N=2).

Blood was collected for PK evaluation at T=0, 5, 10, 15, 20, 25, 30, 45, 60, 90, and 120 minutes and 3, 4, 6, and 8 hours post-dose.

Cohort 1

Eight subjects were enrolled and dosed in Cohort 1. Six subjects received active treatment and 2 received placebo. Active treatment was administered by dry powder inhalation (DPI) as a single capsule of 25 μg treprostinil strength, and placebo treatments were administered by DPI as a single capsule of the placebo formulation. All inhalations were administered using the RS00 inhaler.

Blood samples were obtained prior to dosing and at nominal times of 0.083, 0.167, 0.25, 0.33, 0.417, 0.5, 0.75, 1, 1.5, 2, 2.5, 3, 3.5, 4, 6, and 8 hours after inhalation. Analysis of plasma concentration versus time data for calculation of standard pharmacokinetic (PK) parameters following inhalation was conducted using Phoenix WinNonlin version 6.3 using scheduled blood sampling times. Plasma concentrations were provided only for subjects on active dose and random subject numbers were assigned by the bioanalytical laboratory to retain the study blind.

The table shown in FIG. 3A contains a summary of the treprostinil concentration-time data for individual subjects with descriptive statistics for the six active subjects in Cohort 1. Preliminary non-compartmental PK parameters for treprostinil are summarized in the table shown in FIG. 3B. The highest concentrations for three of the six subjects occurred at 0.33 hours post-inhalation; one subject each had a Tmax of 0.167, 0.25, and 0.417 hours post-dose. Concentrations subsequently decayed with a single-phase disposition profile, as shown in the log-linear plots. At two hours after inhalation, two of six active subjects had measurable concentrations of treprostinil and only one subject had measurable concentrations at 2.5 and 3 hours after inhalation. No subjects had quantifiable concentrations after the 3 hour timepoint.

The Cmax averaged 0.364 ng/mL and the most frequent Tmax was 0.33 hours after inhalation. AUCinf values averaged 0.301 h*ng/mL with a CV % of 30.2%. The apparent volume of distribution (Vz/F) averaged 68.1 L. Oral clearance (CL/F) averaged 91.0 L/h and ranged from 59.1 to 150. Variability in the CL/F value had a CV % of 35.8%.

Cohort 2

Nine subjects were enrolled and dosed in Cohort 2. At least six subjects received active treatment and at least 2 received placebo; 1 subject withdrew before the 2 hour PK sample and was replaced. Subjects with truncated sampling schedules have been excluded in this interim analysis. Active treatment was administered by dry powder inhalation (DPI) as a single capsule of 50 μg treprostinil strength, and placebo treatments were administered by DPI as a single capsule of the placebo formulation. All inhalations were administered using the RS00 inhaler.

Blood samples were obtained prior to dosing and at nominal times of 0.083, 0.167, 0.25, 0.33, 0.417, 0.5, 0.75, 1, 1.5, 2, 2.5, 3, 3.5, 4, 6, and 8 hours after inhalation. Analysis of plasma concentration versus time data for calculation of standard pharmacokinetic (PK) parameters following inhalation was conducted using Phoenix WinNonlin version 6.3 using scheduled blood sampling times. Plasma concentrations were provided only for subjects on active dose and random subject numbers were assigned by the bioanalytical laboratory to retain the study blind.

The table shown in FIG. 4A contains a summary of the treprostinil concentration-time data for individual subjects with descriptive statistics for the six active subjects in Cohort 2.

The highest concentrations for four of the six subjects occurred at 0.17 hours post-inhalation; of the remaining subjects, one had Tmax at 0.083 hours post-dose and one at 0.417 hours post-dose. At 2.5 hours after inhalation, 2 of 6 active subjects had measurable concentrations of treprostinil and only one subject had measurable concentrations at 3 hours after inhalation. No subjects had quantifiable concentrations after the 3 hour timepoint.

Preliminary non-compartmental PK parameters for treprostinil for Cohort 2 are summarized in the table shown in FIG. 4B. The Cmax averaged 0.572 ng/mL and the most frequent Tmax was 0.167 hours after inhalation. AUCinf values averaged 0.422 h*ng/mL with a CV % of 62.8%. The apparent volume of distribution (Vz/F) averaged 110 L. Oral clearance (CL/F) averaged 208 L/h and ranged from 67 to 624. Variability in the CL/F value had a CV % of 101.5%.

By comparison, the Cmax for Cohort 1 averaged 0.364 ng/mL and the AUCinf values averaged 0.301 h*ng/mL. Thus, a doubling of the treprostinil dose resulted in an approximate 50% increase in exposure. The Vz/F and the CL/F values were considerably higher for Cohort 2 and with greater variability.

Cohort 3

Eight subjects were enrolled and dosed in Cohort 3. Six subjects received active treatment and two received placebo. Active treatment was administered by dry powder inhalation (DPI) as a single capsule of 75 μg treprostinil strength and placebo treatments were administered by DPI as a single capsule of the placebo formulation. All inhalations were administered using the RS00 inhaler.

Blood samples were obtained prior to dosing and at nominal times of 0.083, 0.167, 0.25, 0.33, 0.417, 0.5, 0.75, 1, 1.5, 2, 2.5, 3, 3.5, 4, 6, and 8 hours after inhalation. Analysis of plasma concentration versus time data for calculation of standard pharmacokinetic (PK) parameters following inhalation was conducted using Phoenix WinNonlin version 6.3 using scheduled blood sampling times. Plasma concentrations were provided only for subjects on active dose and random subject numbers were assigned by the bioanalytical laboratory to retain the study blind.

The table shown in FIG. 5A contains a summary of the treprostinil concentration-time data for individual subjects with descriptive statistics for the 6 active subjects in Cohort 3.

The highest concentrations for three of the six subjects occurred at 0.25 hours post-inhalation; of the remaining subjects, 1 had Tmax at 0.083 hours post-dose, 1 at 0.17 hours post-dose, and 1 at 0.417 hours post-dose. At 3 hours after inhalation, two of six active subjects had measurable concentrations of treprostinil. No subjects had quantifiable concentrations after the 3 hour timepoint.

Preliminary non-compartmental PK parameters for treprostinil for Cohort 3 are summarized in the table shown in FIG. 5B. The Cmax averaged 0.728 ng/mL and the most frequent Tmax was 0.25 hours after inhalation. AUCinf values averaged 0.757 h*ng/mL with a CV % of 39.4%. The apparent volume of distribution (Vz/F) averaged 97 L. Oral clearance (CL/F) averaged 112 L/h and ranged from 58 to 161. Variability in the CL/F value had a CV % of 39.4%.

By comparison, the Cmax for Cohort 1 and Cohort 2 averaged 0.364 ng/mL and 572 ng/mL, respectively, while the AUCinf values averaged 0.301 h*ng/mL and 0.422 h*ng/mL. Thus, a tripling of the dose from Cohort 1 resulted in an approximate 100-150% increase in exposure. The CL/F values were for Cohort 3 were more consistent with Cohort 1, and with similar variability, than what was observed in Cohort 2. The results indicate that both Cmax and AUCinf may be increasing proportionately to the increase in the dose and that the CL is independent of dose over the range of 25 to 75 μg treprostinil.

Cohort 4

Eight subjects were enrolled and dosed in Cohort 4. Six subjects received active treatment and two received placebo. Active treatment of 100 μg treprostinil was administered by dry powder inhalation (DPI) as 2 capsules of 50 μg treprostinil strength and placebo treatments were administered by DPI as 2 capsules of the placebo formulation. All inhalations were administered using the RS00 inhaler.

Blood samples were obtained prior to dosing and at nominal times of 0.083, 0.167, 0.25, 0.33, 0.417, 0.5, 0.75, 1, 1.5, 2, 2.5, 3, 3.5, 4, 6, and 8 hours after inhalation. Analysis of plasma concentration versus time data for calculation of standard pharmacokinetic (PK) parameters following inhalation was conducted using Phoenix WinNonlin version 6.3 using scheduled blood sampling times. Plasma concentrations were provided only for subjects on active dose and random subject numbers were assigned by the bioanalytical laboratory to retain the study blind.

The table shown in FIG. 6A contains a summary of the treprostinil concentration-time data for individual subjects with descriptive statistics for the six active subjects in Cohort 4. The highest concentrations for 2 of the 6 subjects occurred at 0.25 hours post-inhalation; of the remaining subjects, 2 had Tmax at 0.5 hours post-dose, 1 at 0.17 hours post-dose, and 1 at 0.33 hours post-dose. At 4 hours after inhalation, 3 of 6 active subjects had measurable concentrations of treprostinil. No subjects had quantifiable concentrations at the 6 or 8 hour timepoints.

Preliminary non-compartmental PK parameters for treprostinil for Cohort 4 are summarized in FIG. 6B. The Cmax averaged 1.08 ng/mL and the most frequent Tmax values were observed at 0.25 hours and 0.5 hours after inhalation. AUCinf values averaged 1.22 h*ng/mL with a CV % of 18.4%. The apparent volume of distribution (Vz/F) averaged 96 L. Oral clearance (CL/F) averaged 84.8 L/h and ranged from 68.3 to 122. Variability (CV %) in the CL/F value was 22.8%.

By comparison, the Cmax for Cohorts 1, 2, and 3 averaged 0.364 ng/mL, 0.572 ng/mL, and 0.728 ng/mL respectively, while the AUCinf values averaged 0.301 h*ng/mL, 0.422 h*ng/mL, and 0.757 h*ng/mL. Thus, a quadrupling of the dose from Cohort 1 resulted in an approximate 200-300% increase in exposure, while a doubling of the dose from Cohort 2 resulted in an approximate 2-fold increase in exposure. The results indicate that both Cmax and AUCinf may be increasing proportionately to the increase in the dose and that the CL/F is independent of dose over the range of 25 to 100 μg treprostinil.

Cohort 5

Eight subjects were enrolled and dosed in Cohort 5. Six subjects received active treatment and two received placebo. Active treatment of 125 μg treprostinil was administered by dry powder inhalation (DPI) as 1 capsule of 75 μg and 1 capsule of 50 μg treprostinil strength and placebo treatments were administered by DPI as 2 capsules of the placebo formulation. All inhalations were administered using the RS00 inhaler.

Blood samples were obtained prior to dosing and at nominal times of 0.083, 0.167, 0.25, 0.33, 0.417, 0.5, 0.75, 1, 1.5, 2, 2.5, 3, 3.5, 4, 6, and 8 hours after inhalation. Analysis of plasma concentration versus time data for calculation of standard pharmacokinetic (PK) parameters following inhalation was conducted using Phoenix WinNonlin version 6.3 using scheduled blood sampling times. Plasma concentrations were provided only for subjects on active dose and random subject numbers were assigned by the bioanalytical laboratory to retain the study blind.

The table shown in FIG. 7A contains a summary of the treprostinil concentration-time data for individual subjects with descriptive statistics for the 6 active subjects in Cohort 5. The highest concentrations for 3 of the 6 subjects occurred at 0.17 hours post-inhalation; of the remaining subjects, 2 had Tmax at 0.33 hours post-dose, and 1 at 0.42 hours post-dose. At 3.5 and 4 hours after inhalation, only 1 of 6 active subjects had measurable concentrations of treprostinil. No subjects had quantifiable concentrations at the 6 or 8 hour timepoints.

Preliminary non-compartmental PK parameters for treprostinil for Cohort 5 are summarized in FIG. 7B. The Cmax averaged 1.19 ng/mL and the most frequent Tmax values were observed at 0.17 hours after inhalation. AUCinf values averaged 1.15 h*ng/mL with a CV % of 44.9%. The apparent volume of distribution (Vz/F) averaged 101 L. Oral clearance (CL/F) averaged 141 L/h and ranged from 65.7 to 336. Variability (CV %) in the CL/F value was 69.9%.

By comparison, the Cmax for Cohorts 1, 2, 3, and 4 averaged 0.364 ng/mL, 0.572 ng/mL, 0.728 ng/mL, and 1.08 ng/mL respectively, while the AUCinf values averaged 0.301 h*ng/mL, 0.422 h*ng/mL, 0.757 h*ng/mL, and 1.22 h*ng/mL. Thus, a quintupling of the dose from Cohort 1 resulted in an approximate 220-280% increase in exposure. The results indicate that both Cmax and AUCinf may be increasing proportionately to the increase in the dose and that the CL/F is independent of dose over the range of 25 to 125 µg treprostinil.

Cohort 6

Cohort 6 was conducted as an original and a repeat. In each Cohort 6 (original and repeat), eight subjects were enrolled and dosed. Six subjects received active treatment and two received placebo. Active treatment of 150 µg treprostinil was administered by dry powder inhalation (DPI) as 2 capsules of 75 µg treprostinil strength and placebo treatments were administered by DPI as 2 capsules of the placebo formulation. All inhalations were administered using the RS00 inhaler. Cohort 6 original included some mechanical device failures and subject non-compliance with instructions, giving rise to Cohort 6 repeat.

Blood samples were obtained prior to dosing and at nominal times of 0.083, 0.167, 0.25, 0.33, 0.417, 0.5, 0.75, 1, 1.5, 2, 2.5, 3, 3.5, 4, 6, and 8 hours after inhalation. Analysis of plasma concentration versus time data for calculation of standard pharmacokinetic (PK) parameters following inhalation was conducted using Phoenix WinNonlin version 6.3 using scheduled blood sampling times. Plasma concentrations were provided only for subjects on active dose and random subject numbers were assigned by the bioanalytical laboratory to retain the study blind.

The table shown in FIG. 8A contains a summary of the treprostinil concentration-time data for individual subjects with descriptive statistics for the six active subjects in Cohort 6-R. The highest concentrations for 2 of the 6 subjects occurred at 0.25 hours post-inhalation and at 0.33 hours post-inhalation. In the remaining 2 subjects, Tmax occurred at the 0.167 and 0.417 hours post-dose timepoints. At 4 hours after inhalation, 4 of 6 active subjects had measurable concentrations of treprostinil. No subjects had quantifiable concentrations at the 6 or 8 hour timepoints.

Figure 8D:
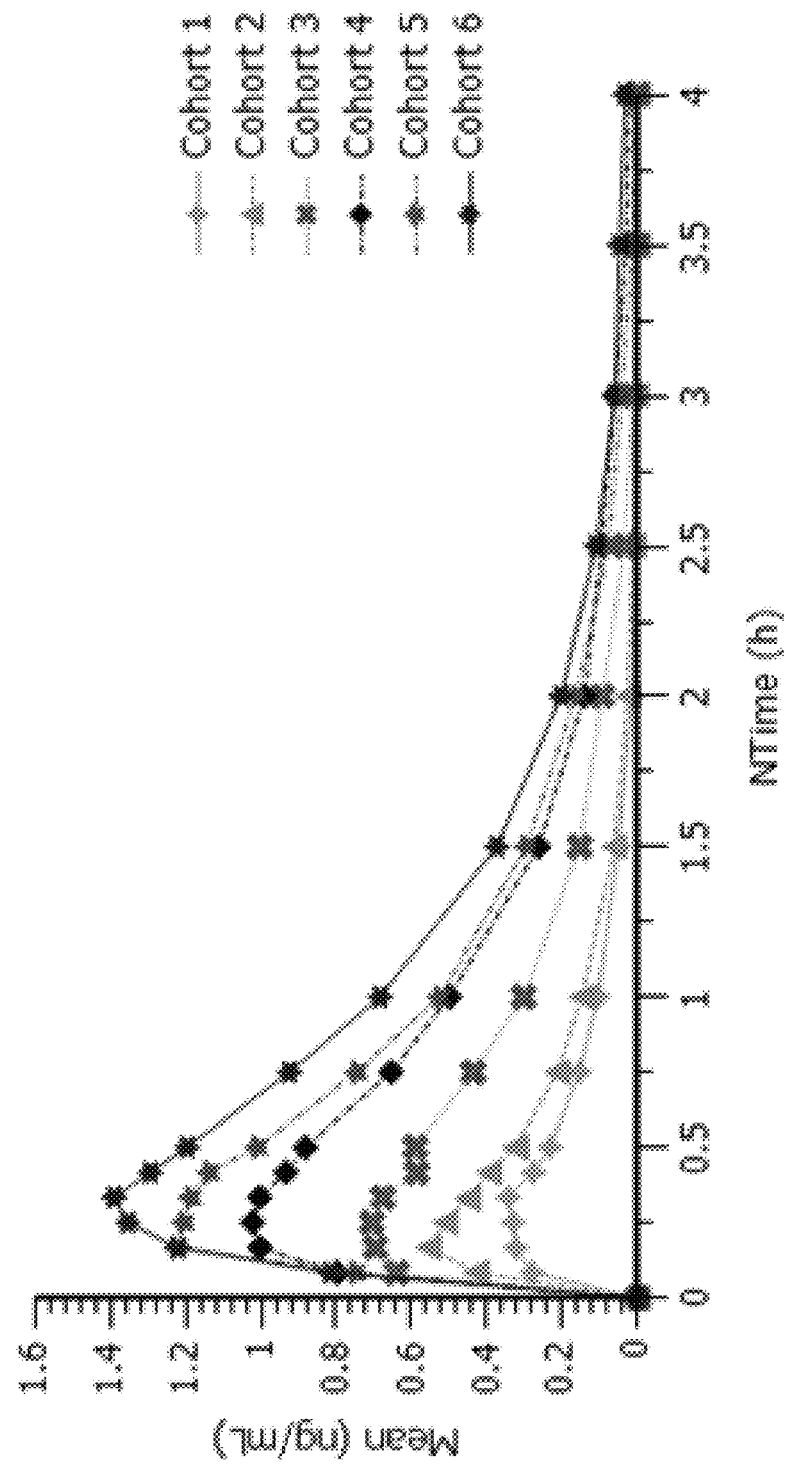
FIGS. 8D, 8E, 8F, and 8G contain data for the clinical trial. Mean concentration-time data for each of the six cohorts is displayed on a linear scale in FIG. 8D. Plots of the relationship between dose and Cmax and AUCinf are displayed in FIG. 8E and FIG. 8F, respectively. A plot of the relationship between dose and the oral clearance, CL/F, is shown in FIG. 8G.

Preliminary non-compartmental PK parameters for treprostinil for Cohort 6-R are summarized in FIG. 8B. Preliminary non-compartmental PK parameters for treprostinil for Cohort 6-Original are summarized in FIG. 8C. Mean concentration-time data for each of the six cohorts is displayed on a linear scale in FIG. 8D. The Cmax averaged 1.45 ng/mL and the most frequent Tmax values were observed at 0.25 and 0.33 hours after inhalation. AUCinf values averaged 1.62 h*ng/mL with a CV % of 68.3%. The apparent volume of distribution (Vz/F) averaged 107 L. Oral clearance (CL/F) averaged 126 L/h and ranged from 51.8 to 245. Variability (CV %) in the CL/F value was 68.3%.

Figure 8E:
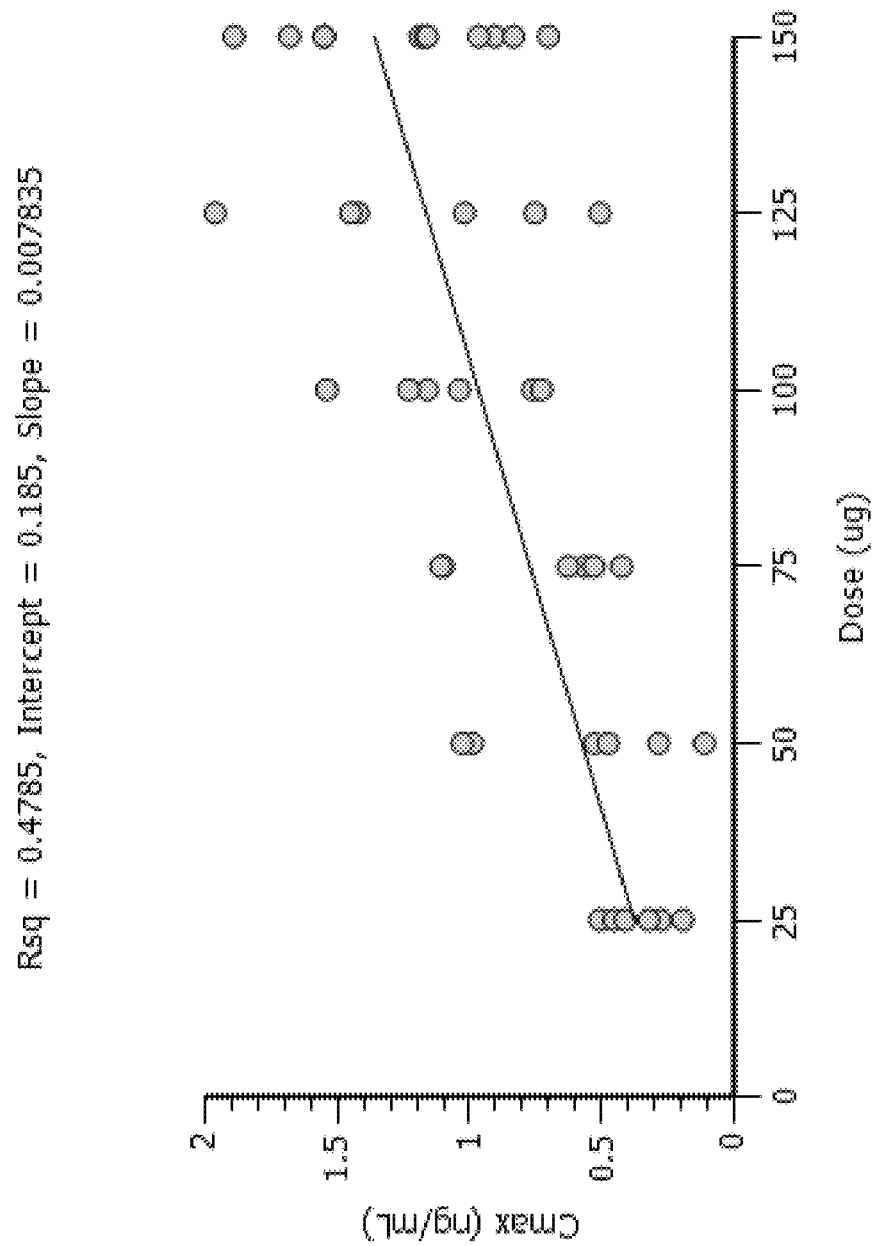
Figure 8F:
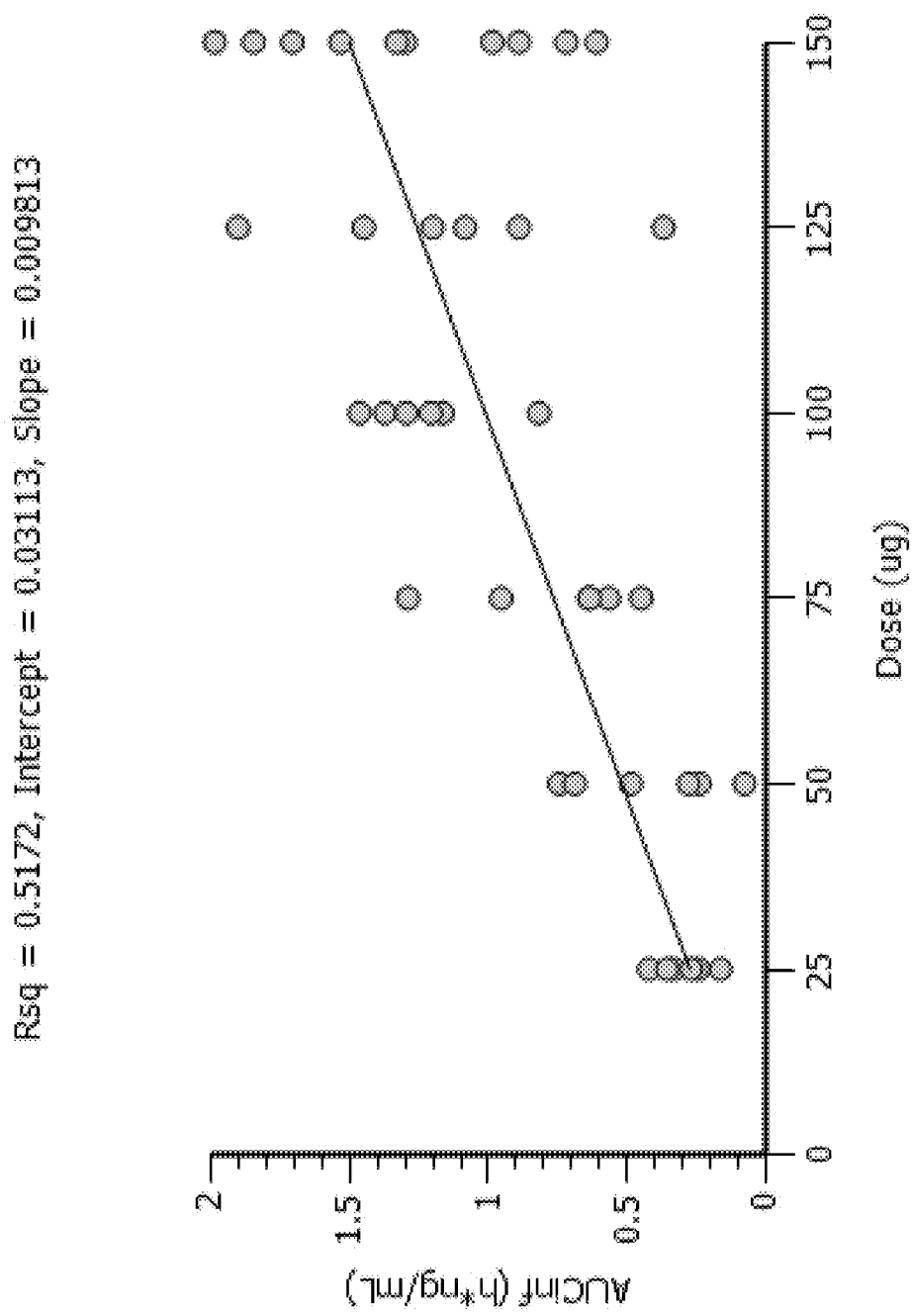
Figure 8G:
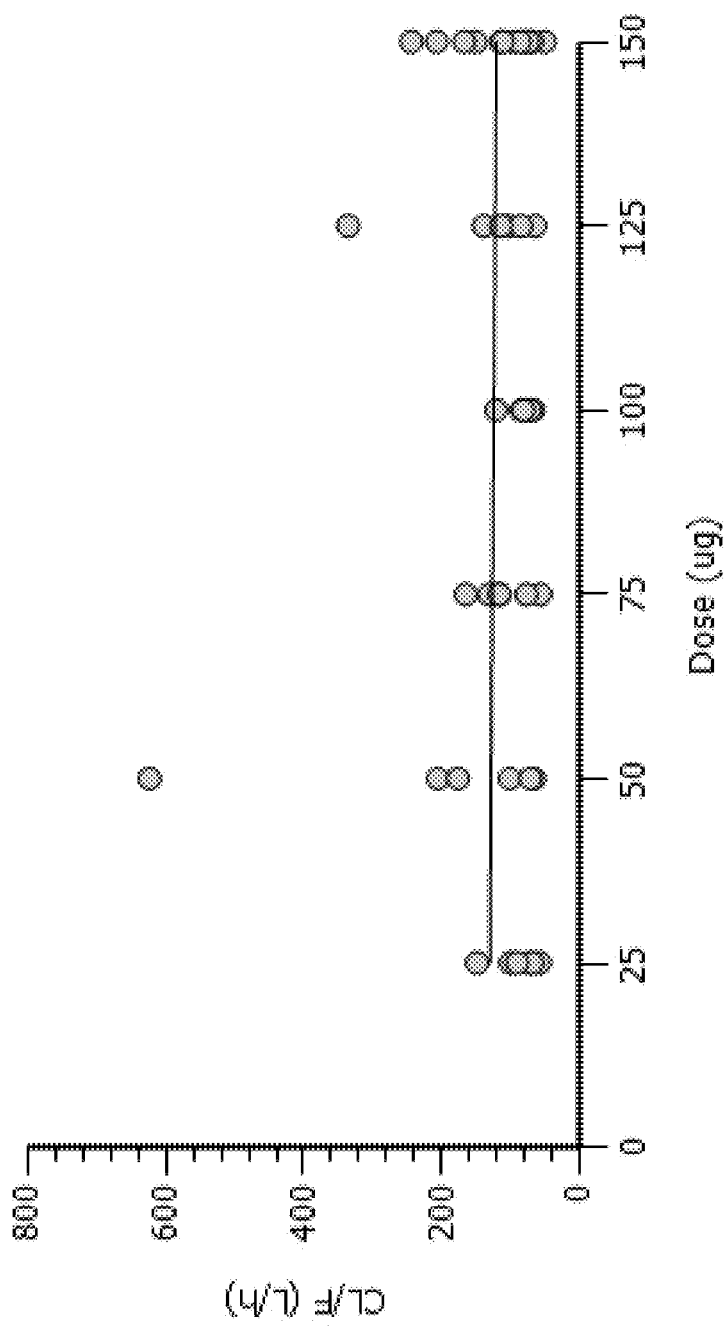

By comparison, the Cmax for Cohorts 1, 2, 3, 4, 5, and the combined Cohort 6 averaged 0.364 ng/mL, 0.572 ng/mL, 0.728 ng/mL, 1.08 ng/mL, 1.19 ng/mL, and 1.21 ng/mL, respectively (FIG. 8E), while the AUCinf values averaged 0.301 h*ng/mL, 0.422 h*ng/mL, 0.757 h*ng/mL, 1.22 h*ng/mL, 1.15 h*ng/mL, and 1.37 h*ng/mL (FIG. 8F). Thus, a 6-fold increase of the dose from Cohort 1 to the combined Cohort 6 observations resulted in an approximate 260-400% increase in exposure, while tripling from Cohort 2 and doubling from Cohort 3 resulted in approximate increases of exposure by 130-255% and 81-98%, respectively. Moreover, plots of the relationship between dose and Cmax and AUCinf are displayed in FIG. 8E and FIG. 8F, respectively. The results indicate that both Cmax and AUCinf may be increasing proportionately to the increase in the dose. It was observed at the CRU during the original 150 µg dosing, however, that there were several apparent device failures that may have resulted in incomplete and/or inefficient exposures. It should be noted that no device failures were noted during the repeat dosing and, while mean values may be higher than in the initial cohort, the variability in the repeated cohort is greater. A plot of the relationship between dose and CL/F (FIG. 8G) shows that the CL/F is independent of dose over the range of 25 to 150 µg treprostinil, which suggests that PK of treprostinil has a proportional relationship to dose over the range of 25 to 150 µg treprostinil.

Clinical Conclusions

LIQ861 was dosed at levels of 25, 50, 75, 100, 125 and 150 µg treprostinil from either a single capsule (25, 50 and 75 mcg doses) or a combination of two lower capsular strengths (for 100, 125 and 150 mcg doses), each capsule either undergoing either a single breath or two breaths. According to embodiments of the present invention, novel capsule to particle powder to active ingredient ratios, and breath per capsule and powder per breath ratios for human dosing are included in the following table.

| Patient presentation of particle powder and active agent per capsule per breath for particle formulation having 0.5 percent active agent load | | | | | | |
|---|---|---|---|---|---|---|
| Capsules | 1 | 1 | 1 | 2 | 2 | 2 |
| Particle Powder in mg | 5 | 10 | 15 | Combination of two 50 mcg capsules or one 25 mcg and one 75 mcg | Combination of, ex., 1 at 50 mcg and 1 at 75 mcg | Combination of, ex., two capsules at 75 mcg |
| Active Agent Load in mcg | 25 | 50 | 75 | Varies, see above | Varies, see above | Varies, see above |
| Breaths to Deliver | 1 to 2 | 1 to 2 | 1 to 2 | 1 to 2 per capsule | 1 to 2 per capsule | 1 to 2 per capsule |
| Particle Powder per Breath in mg | 2.5-5 | 5-10 | 7.5-15 | Varies, up to 15 | Varies, up to 15 | Varies, up to 15 |
| Active Agent per Breath in mcg | 12.5-25 | 25-50 | 37.5-75 | Varies, up to 75 | Varies, up to 75 | Varies, up to 75 |

According to such embodiments, as shown in the above table, each breath can receive from 2.5-15 mg of particle power and from 12.5-75 mcg of active agent.

For the given treprostinil delivered in the given mass of particle powder loaded into a capsule and delivered through a dry powder inhaler results in the human clinical outcomes are included in the following table for LIQ861.

| LIQ861 Clinical Outcomes | $C_{max}$ (ng/mL) | $T_{max}^{a}$ (h) | $t_{1/2}$ (h) | $AUC_{last}$ (h * ng/mL) | $AUC_{inf}$ (h * ng/mL) | CL/F (L/h) | Vz/F (L) |
|---|---|---|---|---|---|---|---|
| 25 mcg Treprostinil | 0.36 (0.12) | 0.33 (0.17, 0.42) | 0.52 (0.16) | 0.27 (0.09) | 0.3 (0.09) | 91 (32.6) | 68.1 (27.4) |
| 50 mcg Treprostinil | 0.57 (0.37) | 0.17 (0.08, 0.42) | 0.45 (0.12) | 0.4 (0.26) | 0.42 (0.27) | 208 (211) | 110 (66.6) |
| 75 mcg Treprostinil | 0.73 (0.3) | 0.25 (0.08, 0.42) | 0.62 (0.18) | 0.72 (0.31) | 0.76 (0.31) | 112 (38.5) | 97 (29.1) |
| 100 mcg Treprostinil | 1.08 (0.31) | 0.29 (0.17, 0.5) | 0.78 (0.13) | 1.18 (0.22) | 1.22 (0.23) | 84.8 (19.3) | 95.5 (28.2) |
| 125 mcg Treprostinil | 1.19 (0.53) | 0.25 (0.17, 0.42) | 0.53 (0.07) | 1.12 (0.51) | 1.15 (0.52) | 141 (98.8) | 101 (58.7) |
| 150 mcg Treprostinil | 1.21 (0.3) | 0.29 (0.08, 0.42) | 0.66 (0.15) | 1.33 (0.44) | 1.37 (0.42) | 119 (35.8) | 115 (51.4) |
| 150 mcg Treprostinil | 1.45 (0.63) | 0.29 (0.17, 0.42) | 0.64 (0.11) | 1.58 (0.85) | 1.62 (0.87) | 126 (80.3) | 107 (54) |

Abbreviations:
SD = standard deviation;
$C_{max}$ = maximum observed plasma concentration;
$T_{max}$ = time to $C_{max}$;
$t_{1/2}$ = half-life;
AUC = area under the curve;
CL/F = apparent clearance;
Vz/F = apparent volume of distribution
All values except for $T_{max}$ are reported as arithmetic means with SD in parentheses.
$^{a}T_{max}$ reports median values with minimum and maximum values in parentheses For comparison, TYVASO (United Therapeutics, Inc.) provides the current standard of treatment for inhaled treprostinil. Such treprostinil is delivered through a nebulizer for the treatment of PAH and is limited to deliver 6 mcg of treprostinil per breath, utilizing 9 breaths to reach a 54 mcg dose. The current standard of inhaled treatment has shown to be dose limited to a maximum tolerated dose of 84 mcg of treprostinil, which required 14 breaths to reach such dose. See, Channick, R. et al., Inhaled Treprostinil: a therapeutic review, Drug Design, Development and Therapy 2012:6 19-28; and Nelsen A C, et al., Pharmacokinetics Of Inhaled Treprostinil Sodium In Healthy Volunteers. Am J Respir Crit Care Med. 2010; 181:A3348; both of which are incorporated herein by reference in their entirety.

In alternative embodiments, particles of the present invention may include 1% treprostinil load, as compared to 0.5% treprostinil load of the LIQ861 particles. According to an embodiment of the present invention, a plurality of 1% treprostinil particles were fabricated from a solution comprising, weight percent solids in water, of: 1.06% treprostinil sodium, 92.44% trehalose dihydrate, 2% polysorbate 80, 4% L leucine, 0.27% sodium citrate dihydrate, and 0.23% sodium chloride.

According to a 1 percent treprostinil particle formulation of the present invention, particle powder mass and active agent presented to a patient comprise the following novel capsule to particle powder to active ingredient ratios, and breath per capsule and powder per breath ratios for human dosing.

| Patient presentation of particle powder and active agent per capsule per breath for particle formulation having 1 percent active agent load | | | | | | |
|---|---|---|---|---|---|---|
| Capsules | 1 | 1 | 1 | 1 | 1 | 1 |
| Particle Powder in mg | 2.5 | 5 | 7.5 | 10 | 12.5 | 15 |
| Active Agent Load in mcg | 25 | 50 | 75 | 100 | 125 | 150 |

-continued

Patient presentation of particle powder and active agent per capsule per breath for particle formulation having 1 percent active agent load

| Capsules | 1 | 1 | 1 | 1 | 1 | 1 |
|---|---|---|---|---|---|---|
| Breaths to Deliver | 1 to 2 | 1 to 2 | 1 to 2 | 1 to 2 | 1 to 2 | 1 to 2 |
| Particle Powder per Breath in mg | 1.25-2.5 | 2.5-5 | 3.75-7.5 | 5-10 | 6.25-12.5 | 7.5-15 |
| Active Agent per Breath in mcg | 12.5-25 | 25-50 | 37.5-75 | 50-100 | 62.5-125 | 75-150 |

According to such embodiments, as shown in the above table, each breath can receive from 1.25-15 mg of particle power and from 12.5-150 mcg of active agent.

For the powder mass found acceptable in LIQ861 initial clinical trial associated with delivery of the 150 mcg dose, at a 1% active drug particle a dose of 300 mcg of active drug can be administered in a safe and acceptable powder mass and excipient quantity.

Kits

According to embodiments of the present invention the dry powder inhaler device can be combined into a kit with capsules for use therein. The capsules can be packaged in blister packs with or without desiccant to ensure controlled environment for the LIQ861 particle powder while the traveling with a user. The blister packs can include capsules for a single dosing or multiple capsules for a day, week or month of doses. Typically a patient will treat 4 times per day for the PAH indication. The kit can include capsules comprising dosage strengths of 25, 50, 75, 100, 125, 150, 200, 250, 300 mcg or beyond for the treatment of PAH. The particles of the powder in the capsules of the kits can be particles comprising 0.5% treprostinil or 1% treprostinil.

| Abbreviations and Nomenclature Cross-references | |
|---|---|
| 6MWD | 6 Minute Walk Distance |
| AE | Adverse Event |
| AUC | Area Under the Curve |
| AUCinf | Area Under the Concentration-Time Curve Extrapolated to Time Infinity |
| AUClast | Area Under the Concentration-Time Curve to the Last Measured Timepoint |
| AUCext | Percentage of Area Under the Curve Extrapolated Beyond Last Measureable Concentration |
| AVT | Acute Pulmonary Vasodilator Testing |
| BA | Bioavailability |
| BDI | Borg Dyspnea Index |
| BLQ | Below the Limit of Quantitation |
| BMPR2 | Bone Morphogenic Protein Receptor Type II Gene |
| BP | British Pharmacopoeia |
| BTO | Benzidine Triol |
| CAS | Chemical Abstracts Service |
| CFR | Code of Federal Regulations |
| CFU | Colony Forming Unit |
| cGMP | Current Good Manufacturing Practice |
| CI | Cardiac Index |
| CL | Clearance |
| Cmax | Maximum Concentration |
| CMC | Chemistry Manufacturing and Controls |
| CO | Cardiac Output |
| COPD | Chronic Obstructive Pulmonary Disease |
| Css | Concentration at Steady State |
| CTEPH | Chronic Thromboembolic Pulmonary Hypertension |
| CYP | Cytochrome P450 |
| DMF | Drug Master File |
| DP | Drug Product |

-continued

| Abbreviations and Nomenclature Cross-references | |
|---|---|
| DPI | Dry Powder Inhaler |
| DPPA | Diphenylphosphinic Acid |
| DRF | Dose Range Finding |
| DS | Drug Substance |
| DUSA | Dosage Unit Sampling Apparatus |
| eCMH | Extended Cochran-Mantel-Haenszel Test |
| ECG | Electrocardiogram |
| ED | Emitted Dose |
| Emax | Maximum Effect |
| EP | European Pharmacopoeia |
| ERA | Endothelin Receptor Agonists |
| ET3 | Polyethylene Terephthalate Cyclic Trimer |
| EU | Endotoxin Unit |
| ESRD | End-Stage Renal Disease |
| F | Bioavailability |
| FCR | Fluorocur ® |
| FDA | Food and Drug Administration |
| FPF | Fine Particle Fraction |
| Frel | Relative Bioavailability |
| FT-IR | Fourier Transform Infrared Spectroscopy |
| GC | Gas Chromatography |
| GLP | Good Laboratory Practice |
| GMP | Good Manufacturing Practice |
| GSD | Geometric Standard Deviation |
| HIAC | High Accuracy Particle Counter |
| HIV | Human Immunodeficiency Virus |
| H-L | Hodges-Lehmann |
| HPLC | High Performance Liquid Chromatography |
| HPMC | Hydroxypropyl Methylcellulose |
| HR | Heart Rate |
| ICH | International Conference on Harmonisation |
| IM | Intramuscular |
| IND | Investigational New Drug |
| INR | International Normalized Ratio |
| IR | Infrared |
| ISO | International Organization for Standardization |
| IV | Intravenous |
| JP | Japanese Pharmacopoeia |
| KF | Karl Fischer Titration |
| LC | Liquid Chromatography |
| LC-MS | Liquid Chromatography with Mass Spectrometry |
| LV | Left Ventricular |
| LVdP/dt | Left Ventricular Contractility |
| mcg | Micrograms, μg or ug |
| MDI | Metered Dose Inhaler |
| MeOH | Methanol |
| MLWHF | Minnesota Living With Heart Failure Questionaire |
| MMAD | Mass Median Aerodynamic Diameter |
| MTD | Maximum Tolerated Dose |
| PAPm | Mean Pulmonary Arterial Pressure |
| NDA | New Drug Application |
| NF | National Formulary |
| NGI | Next Generation Impactor ™ |
| NMR | Nuclear Magnetic Resonance |
| NMT | Not More Than |
| NO | Nitric Oxide |
| NOAEL | No Observed Adverse Effect Level |
| NRF | Normal Renal Function |
| NT | Not Tested |
| NT-proBNP | N-Terminal of the Prohormone Brain Natriuretic Peptide |
| NYHA | New York Heart Association |

| Abbreviations and Nomenclature Cross-references | |
|---|---|
| OHSAS | Occupational Health and Safety Advisory Services |
| OPP | Oriented Polypropylene |
| PAH | Pulmonary Arterial Hypertension |
| PAP | Pulmonary Arterial Pressure |
| PCW | Pulmonary Capillary Wedge pressure |
| PD | Pharmacodynamics |
| PDE5 | Phosphodiesterase Type 5 Inhibitors |
| PE | Polyethylene |
| PET | Polyethylene Terephthalate |
| PGI$_2$ | Prostaglandin I2 (Prostacyclin) |
| PH | Pulmonary Hypertension |
| PK | Pharmacokinetics |
| PPM | Parts Per Million |
| PRINT | Particle Replication In Nonwetting Templates |
| PTFE | Polytetrafluoroethylene |
| PVR | Pulmonary Vascular Resistance |
| QID | Quarter in Die (Four Times Daily) |
| (Q)SAR | Quantitative Structure-Activity Relationship |
| QTc | Corrected QT Interval |
| RH | Relative Humidity |
| RLD | Reference Listed Drug |
| SAC | Single Actuation Content |
| SAE | Serious Adverse Event |
| SAP | Systemic Arterial Pressure |
| SC | Subcutaneous |
| SEM | Standard Error of the Mean |
| SOP | Standard Operating Procedure |
| SVR | Systemic Vascular Resistance |
| t½ | Half-life |
| TBD | To Be Determined |
| TK | Toxicokinetics |
| Tmax | Time of Maximal Concentration |
| TMB acid | Trimethylbenzoic Acid |
| TMB-Ald | Trimethylbenzaldehyde |
| TMP | Trimethylbenzoyl Diphenylphosphine Oxide |
| TRIUMPH | Treprostinil Sodium Inhalation Used in the Management of Pulmonary Arterial Hypertension (clinical trial) |
| TTC | Threshold for Toxicological Concern |
| IUPAC | International Union of Pure and Applied Chemistry |
| μg or ug | Micrograms or mcg |
| US | United States |
| USP | United States Pharmacopeia |
| WHO | World Health Organization |
| WRS | Wilcoxon Rank Sum Test |
| WT | Weight |
| XRD | X-ray Diffractometer |

| Product Nomenclature and Reference Table | | |
|---|---|---|
| Term | Designation | Exemplary Embodiment |
| Drug Substance | DS or treprostinil | Treprostinil, supplied as treprostinil sodium for manufacture of the LIQ861 drug product-intermediate |
| Drug Product-Intermediate | DP-intermediate or LIQ861 DP-intermediate | Dry powder particles of precise size and shape containing an integrated matrix of treprostinil and excipients that is produced using Liquidia's PRINT ® Technology manufacturing process (bulk dry powder prior to capsule filling) |
| Placebo Drug Product-Intermediate | Placebo DP-intermediate | Identical formulation as the DP-Intermediate, but treprostinil is replaced with an equal mass of trehalose |
| Inhalation Powder Drug Product | DP or LIQ861 Drug Product or LIQ861 | LIQ861 DP-intermediate filled into Size 3 HPMC capsules for oral inhalation, but prior to integration with Inhalation Device |
| Placebo Drug Product | Placebo | Placebo DP-intermediate filled into Size 3 hydroxypropyl methylcellulose (HPMC) capsules, but prior to integration with the Inhalation Device |
| Drug Product Strength or Dose | Treprostinil in LIQ861 | Amount of treprostinil in drug product |
| Packaged Drug Product | None | Drug Product in the Primary Packaging |
| Inhalation Device | Device | Device that is used to deliver the Drug Product |
| Premetered Dry Powder Inhaler | DPI | Drug Product integrated with the Inhalation Device; i.e., the final product for patient use |

We claim:

1. A method for treating a patient having pulmonary arterial hypertension, comprising:
   administration of a dry powder composition comprising from about 100 micrograms to about 300 micrograms treprostinil or a pharmaceutically acceptable salt thereof to a patient by inhalation using a dry powder inhaler over one to four breaths to treat pulmonary arterial hypertension.

2. The method of claim 1, wherein the patient receives greater than about 50 micrograms treprostinil per breath.

3. The method of claim 1, wherein the dry powder composition comprises less than or equal to about 30 mg of dry powder per breath.

4. The method of claim 1, wherein the dry powder composition comprises molded dry particles comprising a non-reducing sugar, a wetting agent, a hydrophobicity modifying agent, a pH modifying agent and a buffer.

5. The method of claim 1, wherein the dry powder composition comprises molded dry particles comprising by percent solids about 0.581 percent treprostinil sodium, about 92.32 percent trehalose, about 2.19 percent polysorbate 80, about 4.39 percent L-leucine, about 0.26 percent sodium citrate, and about 0.25 percent sodium chloride.

6. The method of claim 1, wherein the patient inhales the dry powder composition four times a day.

7. The method of claim 6, wherein the patient inhales a fifth dose of the dry powder composition per day.

8. The method of claim 6, wherein the patient inhales between 100 micrograms and 300 micrograms treprostinil or a pharmaceutically acceptable salt thereof through four breaths over a day.

9. The method of claim 6, wherein the patient inhales between 100 micrograms and 600 micrograms treprostinil or a pharmaceutically acceptable salt thereof through four to sixteen breaths per day.

10. A method of treating a patient having pulmonary arterial hypertension, comprising:
    providing a patient a dry powder inhaler;
    providing the patient at least one capsule for use in the dry powder inhaler, wherein the at least one capsule contains a dry powder composition comprising at least 100 micrograms of treprostinil, a non-reducing sugar, a wetting agent, a hydrophobicity modifying agent, a pH modifying agent and a buffer; and
    instructing the patient to utilize the dry powder inhaler to inhale the dry powder composition from each capsule in one to two breaths.

11. The method of claim 10, wherein the capsule comprises at least 150 micrograms of treprostinil.

12. A method of treating a patient having pulmonary arterial hypertension, comprising:
    dosing the patient having pulmonary arterial hypertension with a dry powder dose of treprostinil, wherein the dose of treprostinil is from about 100 micrograms to about 300 micrograms and delivered over one to four breaths,
    wherein the dry powder dose is configured into particles, wherein each particle comprises the treprostinil, a non-reducing sugar, a wetting agent, a hydrophobicity modifying agent, a pH modifying agent and a buffer.

13. A method for treating a patient having pulmonary arterial hypertension, comprising:
    administering a dry powder composition comprising between about 400 micrograms treprostinil and about 1200 micrograms treprostinil to a patient over a day through four to sixteen breaths to treat pulmonary arterial hypertension,
    wherein the dry powder composition is configured as uniform particles.

14. The method of claim 13, wherein the about 400 micrograms treprostinil is inhaled by the patient in eight breaths or less per day.

15. The method of claim 13, wherein about 800 micrograms treprostinil is inhaled by the patient in eight breaths or less per day.

16. The method of claim 13, wherein about 1200 micrograms treprostinil is inhaled by the patient in sixteen breaths or less per day.

17. The method of claim 1, wherein the dry powder composition induces fewer side effects than a nebulized dose of 54 micrograms of treprostinil.

18. The method of claim 10, wherein the dry powder composition induces fewer side effects than a nebulized dose of 54 micrograms of treprostinil.

19. The method of claim 13, wherein the dry powder dose of treprostinil induces fewer side effects than a nebulized dose of 54 micrograms of treprostinil.

* * * * *